United States Patent
Durrant et al.

(10) Patent No.: US 8,343,490 B2
(45) Date of Patent: *Jan. 1, 2013

(54) MONOCLONAL ANTIBODY SC104 AND DERIVATIVE THEREOF SPECIFICALLY BINDING TO A SIALYLTETRAOSYL CARBOHYDRATE AS A POTENTIAL ANTI-TUMOR THERAPEUTIC AGENT

(75) Inventors: Linda Gillian Durrant, Bilasby Notis (GB); Tina Parsons, Nottingham (GB)

(73) Assignee: Cephalon Australia Pty Ltd (AU)

( * ) Notice: Subject to any disclaimer, the term of this patent is extended or adjusted under 35 U.S.C. 154(b) by 0 days.

This patent is subject to a terminal disclaimer.

(21) Appl. No.: 13/020,387

(22) Filed: Feb. 3, 2011

(65) Prior Publication Data

US 2011/0212113 A1 Sep. 1, 2011

Related U.S. Application Data

(63) Continuation of application No. 11/596,501, filed as application No. PCT/GB2005/001805 on May 11, 2005, now Pat. No. 7,915,387.

(30) Foreign Application Priority Data

May 12, 2004 (GB) .................................. 0410627.4

(51) Int. Cl.
   *A61K 39/395* (2006.01)

(52) U.S. Cl. ................................. 424/133.1; 530/387.1
(58) Field of Classification Search ........................ None
See application file for complete search history.

(56) References Cited

OTHER PUBLICATIONS

Rudikoff et al. (Proc Natl Acad Sci USA 1982 vol. 79 p. 1979).*
MacCallum et al. J. Mol. Biol. (1996) 262, 732-745.*
Pascalis et al. (The Journal of Immunology (2002) 169, 3076-3084).*
Casset et al. (BBRC 2003, 307:198-205).*
Vajdos et al. (J. Mol. Biol. (2002) 320, 415-428).*
Chen et al. (J. Mol. Bio. (1999) 293, 865-881).*
Wu et al. (J. Mol. Biol. (1999) 294, 151-162).*
Padlan et al. (PNAS 1989, 86:5938-5942).*
Lamminmaki et al. (JBC 2001, 276:36687-36694).*

* cited by examiner

*Primary Examiner* — Laura B Goddard
*Assistant Examiner* — Meera Natarajan
(74) *Attorney, Agent, or Firm* — Elmore Patent Law Group, P.C.; Darlene A. Vanstone, Esq.; Carolyn S. Elmore, Esq.

(57) ABSTRACT

The present invention provides an isolated specific binding member capable of binding a sialyltetraosyl carbohydrate and directly inducing cell death without the need for immune effector cells. Such a binding member may be an antibody or a part thereof. Also provided are the use of such binding members in medicine and nucleic acids encoding such binding members.

6 Claims, 35 Drawing Sheets

Figure 1D:
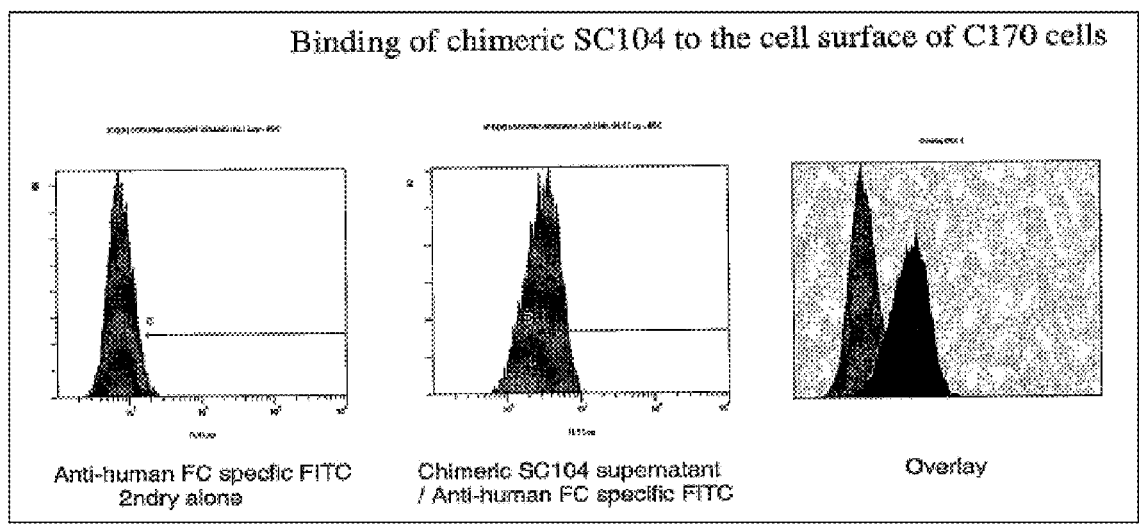

Sequence of SC104 Variable Domain IGg1 Heavy Chain

```
     Forward Heavy Chain Primer                                      FR1
     ──────────────────────────────▶                                 ┌──
  1: M  R  V  L  I  L  L  C  L  F  T  A  F  P  G  I  L  S │ D  V
     ATGAGAGTGCTGATTCTTTTGTGCCTGTTCACAGCCTTTCCTGGTATCCTGTCT GATGTG
  1  ────────!────────!────────!────────!────────!────────!  60
     TACTCTCACGACTAAGAAAACACGGACAAGTGTCGGAAAGGACCATAGGACAGA CTACAC
     ◀────────────────────────────────────────────────────┘
                    Signal Leader Sequence 1: Q  L  Q  E  S  G  P  D  L  V  K  P  S  Q  S  L  S  L  T  C
     CAGCTTCAGGAGTCAGGACCTGACCTGGTGAAACCTTCTCAGTCACTTTCACTCACCTGC
  61 ────────!────────!────────!────────!────────!────────! 120
     GTCGAAGTCCTCAGTCCTGGACTGGACCACTTTGGAAGAGTCAGTGAAAGTGAGTGGACG CDR1                        FR2
                           ┌─────                      ──┐┌──
  1: T  V  T │ G  Y  S  I  T  S  G  Y  S  W  H │ W  V  R  Q  F  P
     ACTGTCACT GGCTACTCCATCACGAGTGGTTATAGTTGGCAC TGGGTCCGGCAGTTTCCA
 121 ────────!────────!────────!────────!────────!────────! 180
     TGACAGTGA CCGATGAGGTAGTGCTCACCAATATCAACCGTG ACCCAGGCCGTCAAAGGT ──────────────────────────────▶               CDR2
                                                 ┌─────
  1: G  N  K  M  E  W  M  G │ H  I  H  F  S  G  R  F  T  Y  N  P
     GGAAACAAAATGGAATGGATGGGC CACATTCACTTCAGTGGTAGACCTACTTACAATCCA
 181 ────────!────────!────────!────────!────────!────────! 240
     CCTTTGTTTTACCTTACCTACCCG GTGTAAGTGAAGTCACCATCTGGATGAATGTTAGGT FR3
                                                  ◀──────────────────
  1: S  L  S  S │ R  I  S  I  T  R  D  T  S  K  N  Q  F  L  L  Q
     TCTCTCAGCAGT CGAATCTCGATCACTCGAGACACATCCAAGAACCAGTTCCTCCTGCAA
 241 ────────!────────!────────!────────!────────!────────! 300
     AGAGAGTCGTCA GCTTAGAGCTAGTGAGCTCTGTGTAGGTTCTTGGTCAAGGAGGACGTT 1: L  K  F  V  T  T  E  D  T  S  T  Y  F  C  A  R │ K  G  K  G
     TTGAAATTTGTGACTACTGAAGACACATCCACATATTTTTGTGCAAGG AAGGGAAAAGGT
 301 ────────!────────!────────!────────!────────!────────! 360
     AACTTTAAACACTGATGACTTCTGTGTAGGTGTATAAAAACACGTTCC TTCCCTTTTCCA CDR3                            FR4                 CH1
       ┌─────                  ◀──────────────────────────┐ ┌──
  1: S  D  D  G  L  N  Y │ W  G  Q  G  I  S  V  T  V  S │ A  K
     TCCGACGATGGTTTGAACTAC TGGGGTCAAGGAATCTCAGTCACCGTCTCTTCA GCCAAA
 361 ────────!────────!────────!────────!────────!────────! 420
     AGGCTGCTACCAAACTTGATG ACCCCAGTTCCTTAGAGTCAGTGGCAGAGAAGT CGGTTT Constant domain
  1: T  T  P  P  P  V  Y  P  L  V  P  G  S  L
     ACGACACCCCCACCCGTTTATCCCTTGGTCCCTGGAAGCTTGG
 421 ────────!────────!────────!────────!──── 463
     TGCTGTGGGGGTGGGCAAATAGGGAACCAGGGACCTTCGAACC
     ◀──────────────────────────────
         Reverse Heavy Chain CH1 Primer
```

FIG. 1A

FIG. 1B

Sequence of SC104 Variable Domain Kappa Light Chain

```
     Forward Kappa Chain Primer           Signal Leader Sequence
1:   M  D  L  Q  V  Q  I  F  S  F  L  L  I  S  A  S  V  I  M  S
     ATGGATTTACAGGTGCAGATTTTCAGCTTCCTGCTAATCAGTGCCTCAGTCATAATGTCC
1    ------------|------------|------------|------------|------------|------------|   60
     TACCTAAATGTCCACGTCTAAAAGTCGAAGGACGATTAGTCACGGAGTCAGTATTACAGG FR1
1:   R  G  E  N  V  L  T  Q  S  P  V  I  M  S  A  S  P  G  E  K
     AGAGGAGAAAATGTTCTCACCCAGTCTCCAGTAATCATGTCTGCATCTCCAGGGGAAAAG
61   ------------|------------|------------|------------|------------|------------|  120
     TCTCCTCTTTTACAAGAGTGGGTCAGAGGTCATTAGTACAGACGTAGAGGTCCCCTTTTC CDR1                              FR2
1:   V  T  M  T  C  S  A  S  S  S  L  S  Y  I  H  W  Y  Q  Q  K
     GTCACCATGACCTGCAGTGCCAGCTCAAGTTTAAGTTACATACACTGGTACCAGCAGAAG
121  ------------|------------|------------|------------|------------|------------|  180
     CAGTGGTACTGGACGTCACGGTCGAGTTCAAATTCAATGTATGTGACCATGGTCGTCTTC CDR2                       FR3
1:   S  R  T  S  P  K  L  W  I  Y  D  T  S  N  L  A  S  G  V  P
     TCAAGAACCTCCCCCAAACTCTGGATTTATGACACATCCAACCTGGCTTCTGGAGTCCCA
181  ------------|------------|------------|------------|------------|------------|  240
     AGTTCTTGGAGGGGGTTTGAGACCTAAATACTGTGTAGGTTGGACCGAAGACCTCAGGGT 1:   G  R  F  S  G  S  G  S  G  N  S  Y  S  L  T  I  S  S  M  E
     GGTCGCTTCAGTGGCAGTGGGTCTGGAAACTCTTATTCTCTCACGATCAGCAGCATGGAG
241  ------------|------------|------------|------------|------------|------------|  300
     CCAGCGAAGTCACCGTCACCCAGACCTTTGAGAATAAGAGAGTGCTAGTCGTCGTACCTC CDR3                       FR4
1:   A  E  D  V  A  T  Y  Y  C  F  Q  G  S  E  Y  P  L  T  F  G
     GCTGAAGATGTTGCCACTTATTACTGTTTTCAGGGGAGTGAGTATCCACTCACGTTCGGG
301  ------------|------------|------------|------------|------------|------------|  360
     CGACTTCTACAACGGTGAATAATGACAAAGTCCCCTCACTCATAGGTGAGTGCAAGCCC CH1 Constant Domain
1:   G  G  T  K  L  E  M  T  R  A  D  A  A  P  T  V  S  I  F  P
     GGGGGGACCAAGCTGGAAATGACACGGGCTGATGCTGCACCAACTGTATCCATCTTCCCA
361  ------------|------------|------------|------------|------------|------------|  420
     CCCCCCTGGTTCGACCTTTACTGTGCCCGACTACGACGTGGTTGACATAGGTAGAAGGGT
                                                            Reverse Kappa
1:   P  S  S  K  L  G  K
     CCATCCAGTAAGCTTGGGAAGGG
421  ------------|------------|----  443
     GGTAGGTCATTCGAACCCTTCCC
     Chain CH1 Primer
```

FIG. 1C

Silver stained gel showing SC104 immuno-purified antigen using the SC104-Protein A sepharose column M= BioRad markers, 1 = sputum; 2 = unbound from column; 3 = 0.1M Tris pH 7.6 0.5% NP40; 4 = 0.1M Tris pH 7.6 0.2% NP40 1M NaCl; 5 = 0.1 M Tris pH 7.6 0.1% NP40; 6= 0.1M Tris pH7.6; 7 = Diethanol amine pH 11.5 eluted pooled fraction This data was obtained from the CSU749a study. SC104 plus 5-FU/leucovorin exhibited a significant reduction in final weight/time and inhibited tumour growth with enhanced survival in the C170 subcutaneous xenograft model.

the isolated specific binding member may additionally comprise one or both, preferably both, of the binding domains substantially as set out as residues 44 or 49 to 54 and residues 69 to 84 of the amino acid sequence shown in FIG. 1a (SEQ ID NO: 23).

SEQUENCE LISTING

```
<160> NUMBER OF SEQ ID NOS: 28

<210> SEQ ID NO 1
<211> LENGTH: 23
<212> TYPE: DNA
<213> ORGANISM: Artificial Sequence
<220> FEATURE:
<223> OTHER INFORMATION: Forward Primer (Heavy Chain)

<400> SEQUENCE: 1
dtgagagtgc tgattctttt gtg                                              23

<210> SEQ ID NO 2
<211> LENGTH: 30
<212> TYPE: DNA
<213> ORGANISM: Artificial Sequence
<220> FEATURE:
<223> OTHER INFORMATION: Forward Primer (Kappa Chain)

<400> SEQUENCE: 2
dtggatttwc argtgcagat twtcagcttc                                       30

<210> SEQ ID NO 3
<211> LENGTH: 35
<212> TYPE: DNA
<213> ORGANISM: Artificial Sequence
<220> FEATURE:
<223> OTHER INFORMATION: Reverse Primer (Heavy Chain)

<400> SEQUENCE: 3
dccaagcttc cagggrccar kggataracg grtgg                                 35

<210> SEQ ID NO 4
<211> LENGTH: 30
<212> TYPE: DNA
<213> ORGANISM: Artificial Sequence
<220> FEATURE:
<223> OTHER INFORMATION: Reverse Primer (Kappa Chain)

<400> SEQUENCE: 4
dccaagctta ctggatggtg ggaagatgga                                       30
```

<210> SEQ ID NO 5
<211> LENGTH: 11
<212> TYPE: PRT
<213> ORGANISM: Mus Musculus

<400> SEQUENCE: 5

Gly Tyr Ser Ile Thr Ser Gly Tyr Ser Trp His
 1               5                  10

<210> SEQ ID NO 6
<211> LENGTH: 33
<212> TYPE: DNA
<213> ORGANISM: Mus Musculus

<400> SEQUENCE: 6
ggctactcca tcacgagtgg ttatagttgg cac                          33

<210> SEQ ID NO 7
<211> LENGTH: 6
<212> TYPE: PRT
<213> ORGANISM: Mus Musculus

<400> SEQUENCE: 7

Ser Gly Tyr Ser Trp His
 1               5

<210> SEQ ID NO 8
<211> LENGTH: 18
<212> TYPE: DNA
<213> ORGANISM: Mus Musculus

<400> SEQUENCE: 8
agtggttata gttggcac                                           18

<210> SEQ ID NO 9
<211> LENGTH: 16
<212> TYPE: PRT
<213> ORGANISM: Mus Musculus

<400> SEQUENCE: 9

His Ile His Phe Ser Gly Arg Pro Thr Tyr Asn Pro Ser Leu Ser Ser
 1               5                  10                  15

<210> SEQ ID NO 10
<211> LENGTH: 48
<212> TYPE: DNA
<213> ORGANISM: Mus Musculus

<400> SEQUENCE: 10
cacattcact tcagtggtag acctacttac aatccatctc tcagcagt          48

<210> SEQ ID NO 11
<211> LENGTH: 11
<212> TYPE: PRT
<213> ORGANISM: Mus Musculus

<400> SEQUENCE: 11

Lys Gly Lys Gly Ser Asp Asp Gly Leu Asn Tyr
 1               5                  10

<210> SEQ ID NO 12
<211> LENGTH: 33
<212> TYPE: DNA
<213> ORGANISM: Mus Musculus

<400> SEQUENCE: 12
aagggaaaag gttccgacga tggtttgaac tac                          33

<210> SEQ ID NO 13
<211> LENGTH: 10
<212> TYPE: PRT
<213> ORGANISM: Mus Musculus

<400> SEQUENCE: 13

Ser Ala Ser Ser Ser Leu Ser Tyr Ile His
 1               5                  10

<210> SEQ ID NO 14
<211> LENGTH: 30
<212> TYPE: DNA
<213> ORGANISM: Mus Musculus

<400> SEQUENCE: 14
agtgccagct caagtttaag ttacatacac                              30

<210> SEQ ID NO 15
<211> LENGTH: 7
<212> TYPE: PRT
<213> ORGANISM: Mus Musculus

<400> SEQUENCE: 15

Asp Thr Ser Asn Leu Ala Ser
 1               5

<210> SEQ ID NO 16
<211> LENGTH: 21
<212> TYPE: DNA
<213> ORGANISM: Mus Musculus

<400> SEQUENCE: 16
gacacatcca acctggcttc t                                       21

<210> SEQ ID NO 17
<211> LENGTH: 9
<212> TYPE: PRT
<213> ORGANISM: Mus Musculus

<400> SEQUENCE: 17

Phe Gln Gly Ser Glu Tyr Pro Leu Thr
 1               5

<210> SEQ ID NO 18
<211> LENGTH: 27
<212> TYPE: DNA
<213> ORGANISM: Mus Musculus

<400> SEQUENCE: 18
tttcagggga gtgagtatcc actcacg                                 27

<210> SEQ ID NO 19
<211> LENGTH: 39
<212> TYPE: DNA
<213> ORGANISM: Mus Musculus

<400> SEQUENCE: 19
ctcagtcacc gtctctagcg ctaaaacgac accccacc                     39

<210> SEQ ID NO 20
<211> LENGTH: 39

```
<212> TYPE: DNA
<213> ORGANISM: Mus Musculus

<400> SEQUENCE: 20
ggtgggggtg tcgttttagc gctagagacg gtgactgag                          39

<210> SEQ ID NO 21
<211> LENGTH: 39
<212> TYPE: DNA
<213> ORGANISM: Mus Musculus

<400> SEQUENCE: 21
ccaagctgga aatgacacgt acggatgctg caccaactg                          39

<210> SEQ ID NO 22
<211> LENGTH: 39
<212> TYPE: DNA
<213> ORGANISM: Mus Musculus

<400> SEQUENCE: 22
cagttggtgc agcatccgta cgtgtcattt ccagcttgg                          39

<210> SEQ ID NO 23
<211> LENGTH: 154
<212> TYPE: PRT
<213> ORGANISM: Mus Musculus

<400> SEQUENCE: 23

Met Arg Val Leu Ile Leu Leu Cys Leu Phe Thr Ala Phe Pro Gly Ile
  1               5                  10                  15

Leu Ser Asp Val Gln Leu Gln Glu Ser Gly Pro Asp Leu Val Lys Pro
                 20                  25                  30

Ser Gln Ser Leu Ser Leu Thr Cys Thr Val Thr Gly Tyr Ser Ile Thr
             35                  40                  45

Ser Gly Tyr Ser Trp His Trp Val Arg Gln Phe Pro Gly Asn Lys Met
         50                  55                  60

Glu Trp Met Gly His Ile His Phe Ser Gly Arg Pro Thr Tyr Asn Pro
 65                  70                  75                  80

Ser Leu Ser Ser Arg Ile Ser Ile Thr Arg Asp Thr Ser Lys Asn Gln
                 85                  90                  95

Phe Leu Leu Gln Leu Lys Phe Val Thr Thr Glu Asp Thr Ser Thr Tyr
            100                 105                 110

Phe Cys Ala Arg Lys Gly Lys Gly Ser Asp Asp Gly Leu Asn Tyr Trp
        115                 120                 125

Gly Gln Gly Ile Ser Val Thr Val Ser Ser Ala Lys Thr Thr Pro Pro
    130                 135                 140

Pro Val Tyr Pro Leu Val Pro Gly Ser Leu
145                 150

<210> SEQ ID NO 24
<211> LENGTH: 463
<212> TYPE: DNA
<213> ORGANISM: Mus Musculus

<400> SEQUENCE: 24
atgagagtgc tgattctttt tgtgcctgtt cacagccttt ctggtatcct gtctgatgtg    60
cagcttcagg agtcaggacc tgacctggtg aaaccttctc agtcactttc actcacctgc   120
actgtcactg gctactccat cacgagtggt tatagttggc actgggtccg gcagtttcca   180
ggaaacaaaa tggaatggat gggccacatt cacttcagtg gtagacctac ttacaatcca   240
```

```
tctctcagca gtcgaatctc gatcactcga gacacatcca agaaccagtt cctcctgcaa      300
ttgaaatttg tgactactga agacacatcc acatattttt gtgcaaggaa gggaaaaggt      360
tccgacgatg gtttgaacta ctggggtcaa ggaatctcag tcaccgtctc ttcagccaaa      420
acgacacccc cacccgttta tcccttggtc cctggaagct tgg                       463

<210> SEQ ID NO 25
<211> LENGTH: 154
<212> TYPE: PRT
<213> ORGANISM: Mus Musculus

<400> SEQUENCE: 25

Met Arg Val Leu Ile Leu Leu Cys Leu Phe Thr Ala Phe Pro Gly Ile
 1               5                  10                  15

Leu Ser Asp Val Gln Leu Gln Glu Ser Gly Pro Asp Leu Val Lys Pro
                20                  25                  30

Ser Gln Ser Leu Ser Leu Thr Cys Thr Val Thr Gly Tyr Ser Ile Thr
            35                  40                  45

Ser Gly Tyr Ser Trp His Trp Val Arg Gln Phe Pro Gly Asn Lys Met
        50                  55                  60

Glu Trp Met Gly His Ile His Phe Ser Gly Arg Pro Thr Tyr Asn Pro
 65                 70                  75                  80

Ser Leu Ser Ser Arg Ile Ser Ile Thr Arg Asp Thr Ser Lys Asn Gln
                85                  90                  95

Phe Leu Leu Gln Leu Lys Phe Val Thr Thr Glu Asp Thr Ser Thr Tyr
               100                 105                 110

Phe Cys Ala Arg Lys Gly Lys Gly Ser Asp Asp Gly Leu Asn Tyr Trp
           115                 120                 125

Gly Gln Gly Ile Ser Val Thr Val Ser Ser Ala Lys Thr Thr Pro Pro
       130                 135                 140

Pro Val Tyr Pro Leu Val Pro Gly Ser Leu
145                 150

<210> SEQ ID NO 26
<211> LENGTH: 463
<212> TYPE: DNA
<213> ORGANISM: Mus Musculus

<400> SEQUENCE: 26
atgagagtgc tgattctttt gtgcctgttc acagcctttc ctggtatcct gtctgatgtg       60
cagcttcagg agtcaggacc tgacctggtg aaaccttctc agtcactttc actcacctgc      120
actgtcactg gctactccat cacgagtggt tatagttggc actgggtccg gcagtttcca      180
ggaaacaaaa tggaatggat gggccacatt cacttcagtg gtagacctac ttacaatcca      240
tctctcagca gtcgaatctc gatcactcga gacacatcca agaaccagtt cctcctgcaa      300
ttgaaatttg tgactactga agacacatcc acatattttt gtgcaaggaa gggaaaaggt      360
tccgacgatg gtttgaacta ctggggtcaa ggaatctcag tcaccgtctc ttcagccaaa      420
acgacacccc cacccgttta tcccttggtc cctggaagct tgg                       463

<210> SEQ ID NO 27
<211> LENGTH: 147
<212> TYPE: PRT
<213> ORGANISM: Mus Musculus

<400> SEQUENCE: 27

Met Asp Leu Gln Val Gln Ile Phe Ser Phe Leu Leu Ile Ser Ala Ser
```

```
                1               5                   10                  15
Val Ile Met Ser Arg Gly Glu Asn Val Leu Thr Gln Ser Pro Val Ile
                20                  25                  30

Met Ser Ala Ser Pro Gly Glu Lys Val Thr Met Thr Cys Ser Ala Ser
                35                  40                  45

Ser Ser Leu Ser Tyr Ile His Trp Tyr Gln Gln Lys Ser Arg Thr Ser
                50                  55                  60

Pro Lys Leu Trp Ile Tyr Asp Thr Ser Asn Leu Ala Ser Gly Val Pro
65                              70                  75                  80

Gly Arg Phe Ser Gly Ser Gly Ser Gly Asn Ser Tyr Ser Leu Thr Ile
                85                  90                  95

Ser Ser Met Glu Ala Glu Asp Val Ala Thr Tyr Tyr Cys Phe Gln Gly
                100                 105                 110

Ser Glu Tyr Pro Leu Thr Phe Gly Gly Gly Thr Lys Leu Glu Met Thr
                115                 120                 125

Arg Ala Asp Ala Ala Pro Thr Val Ser Ile Phe Pro Pro Ser Ser Lys
                130                 135                 140

Leu Gly Lys
145

<210> SEQ ID NO 28
<211> LENGTH: 443
<212> TYPE: DNA
<213> ORGANISM: Mus Musculus

<400> SEQUENCE: 28
atggatttac aggtgcagat tttcagcttc ctgctaatca gtgcctcagt cataatgtcc      60
agaggagaaa atgttctcac ccagtctcca gtaatcatgt ctgcatctcc aggggaaaag    120
gtcaccatga cctgcagtgc cagctcaagt ttaagttaca tacactggta ccagcagaag    180
tcaagaacct cccccaaact ctggatttat gacacatcca acctggcttc tggagtccca    240
ggtcgcttca gtggcagtgg gtctggaaac tcttattctc tcacgatcag cagcatggag    300
gctgaagatg ttgccactta ttactgtttt caggggagtg agtatccact cacgttcggg    360
ggggggacca agctggaaat gacacgggct gatgctgcac caactgtatc catcttccca    420
ccatccagta agcttgggaa ggg                                             443
```

MONOCLONAL ANTIBODY SC104 AND DERIVATIVE THEREOF SPECIFICALLY BINDING TO A SIALYLTETRAOSYL CARBOHYDRATE AS A POTENTIAL ANTI-TUMOR THERAPEUTIC AGENT

RELATED APPLICATIONS

This application is a continuation of U.S. application Ser. No. 11/596,501, filed Aug. 13, 2007, which is a US National stage entry of International Application No. PCT/GB2005/001805, which designated the United States and was filed on May 11, 2005, published in English. This application claims priority under 35 U.S.C. §119 or 365 to United Kingdom, Application No. 0410627.4, filed Dec. 5, 2004. The entire teachings of the above applications are incorporated herein by reference.

The present invention relates to specific binding members, particularly antibodies and fragments thereof, which bind to an epitope relevant to cancer and endometriosis. Such members are useful for the diagnosis and treatment of tumours.

Antibodies which bind to GM2, GD3 and GM3 gangliosides are known, but an antibody that binds a sialyltetraosylceramide, but which does not bind to GM1, GD1a, GT1b or sialyl Lewis antigens has not previously been described. A mouse monoclonal antibody (mab), known herein as "SC104", was raised to sequential immunisation with 4 colorectal cancer cell lines and binds to 71% of colorectal tumours. SC104 is specific for a sialyltetraosyl carbohydrate, which may be present on a lipid (ceramide) or protein backbone, and recognises oesophageal, colorectal, gastric, breast, parotid and endometrial tumours. SC104 is unusual as it is an IgG1 antibody. One of the immunological characteristics of carbohydrate antigens is that they usually elicit a T-cell independent response, resulting in the production of an IgM antibody. SC104 was shown by immunostaining HPLTC plates of lipid extracts from the colorectal cell line C170, to bind to a sialyltetraosylceramide. SC104 was also shown to bind to a protein moiety which has the sialyltetraosyl carbohydrate. Recognition of normal tissue was minimal and restricted to moderate staining of the large intestine, salivary gland, small intestine, thymus, tonsils and uterine cervix. The present inventors also, surprisingly, found that the antibody induced cell death.

According to a first aspect of the present invention, there is provided an isolated specific binding member capable of binding a sialyltetraosyl carbohydrate and of directly inducing cell death without the need for immune effector cells.

A second aspect of the invention provides an isolated specific binding member capable of binding a sialyltetraosyl carbohydrate, which sialyltetraosyl carbohydrate is capable of being bound by a member comprising one or more binding domains selected from domains comprising an amino acid sequence substantially as set out as residues 44 or 49 to 54, 69 to 84 and 117 to 127 of the amino acid sequence of FIG. 1a.

The binding domain may comprise an amino acid sequence substantially as set out as residues 117 to 127 of FIG. 1a.

In one embodiment, the isolated specific binding member of the second aspect of the present invention comprises one or more binding domains selected from domains which comprise an amino acid sequence substantially as set out as residues 44 or 49 to 54, 69 to 84 or 117 to 127 of the amino acid sequence of FIG. 1a (SEQ ID NO: 23).

In one embodiment, the member comprises a binding domain which comprises an amino acid sequence substantially as set out as residues 117 to 127 of the amino acid sequence of FIG. 1a (SEQ ID NO: 23). In this embodiment, the isolated specific binding member may additionally comprise one or both, preferably both, of the binding domains substantially as set out as residues 44 or 49 to 54 and residues 69 to 84 of the amino acid sequence shown in FIG. 1a (SEQ ID NO: 23).

One isolated specific binding member of the second aspect of the invention comprises the amino acid sequence substantially as set out as residues 19 to 138 of the amino acid sequence shown in FIG. 1a (SEQ ID NO: 23).

In a third aspect, the present invention provides an isolated specific binding member capable of binding a sialyltetraosyl carbohydrate, which sialyltetraosyl carbohydrate is capable of being bound by a member comprising one or more binding domains selected from domains comprising an amino acid sequence substantially as set out as residues 46 to 55, 71 to 77 and 110 to 118 of the amino acid sequence of FIG. 1c (SEQ ID NO: 27).

The binding domain may comprise an amino acid sequence substantially as set out as residues 110 to 118 of the amino acid sequence of FIG. 1c (SEQ ID NO: 27).

In one embodiment, the isolated specific binding member of the third aspect of the present invention comprises one or more binding domains selected from domains which comprise an amino acid sequence substantially as set out as residues 46 to 55, 71 to 77 and 110 to 118 of the amino acid sequence of FIG. 1c (SEQ ID NO: 27).

In one embodiment, the member comprises a binding domain which comprises an amino acid sequence substantially as set out as residues 110 to 118 of the amino acid sequence of FIG. 1c. In this embodiment, the isolated specific binding member may additionally comprise one or both, preferably both, of the binding domains substantially as set out as residues 46 to 55 and residues 71 to 77 of the amino acid sequence shown in FIG. 1c (SEQ ID NO: 27).

Specific binding members which comprise a plurality of binding domains of the same or different sequence, or combinations thereof, are included within the present invention. The or each binding domain may be carried by a human antibody framework. For example, one or more binding regions may be substituted for the CDRs of a whole human antibody or of the variable region thereof.

One isolated specific binding member of the third aspect of the invention comprises the sequence substantially as set out as residues 23 to 128 of the amino acid sequence shown in FIG. 1c (SEQ ID NO: 27).

In a fourth aspect, the invention provides a specific binding member which comprises a binding member of the second aspect in combination or association with a binding member of the third aspect. Such a binding member may be in the form of a $F_v$, $(Fab')_2$, or scFV antibody fragment.

Specific binding members of the invention may carry a detectable or functional label.

In further aspects, the invention provides an isolated nucleic acid which comprises a sequence encoding a specific binding member of the first, second, third or fourth aspects of the invention, and methods of preparing specific binding members of the invention which comprise expressing said nucleic acids under conditions to bring about expression of said binding member, and recovering the binding member.

Specific binding members according to the invention may be used in a method of treatment or diagnosis of the human or animal body, such as a method of treatment of a tumour in a patient (preferably human) which comprises administering to said patient an effective amount of a specific binding member of the invention. The invention also provides a specific binding member of the present invention for use in medicine, as well as the use of a specific binding member of the present invention in the manufacture of a medicament for the diagnosis or treatment of a tumour.

The invention also provides the antigen to which the specific binding members of the present invention bind. In one embodiment, a sialyltetraosyl carbohydrate which is capable of being bound, preferably specifically, by a specific binding member of the present invention is provided. The sialyltetraosyl carbohydrate may be provided in isolated form, and may be used in a screen to develop further specific binding members therefor. For example, a library of compounds may be screened for members of the library which bind specifically to the sialyltetraosyl carbohydrate. The sialyltetraosyl carbohydrate may on a lipid backbone (i.e. a sialyltetraosylceramide) or on a protein backbone. When on a protein backbone, it may have a molecular weight of about 50-75 kDa, as determined by SDS-PAGE.

These and other aspects of the invention are described in further detail below.

As used herein, a "specific binding member" is a member of a pair of molecules which have binding specificity for one another. The members of a specific binding pair may be naturally derived or wholly or partially synthetically produced. One member of the pair of molecules has an area on its surface, which may be a protrusion or a cavity, which specifically binds to and is therefore complementary to a particular spatial and polar organisation of the other member of the pair of molecules. Thus, the members of the pair have the property of binding specifically to each other. Examples of types of specific binding pairs are antigen-antibody, biotin-avidin, hormone-hormone receptor, receptor-ligand, enzyme-substrate. The present invention is generally concerned with antigen-antibody type reactions, although it also concerns small molecules which bind to the antigen defined herein.

As used herein, "treatment" includes any regime that can benefit a human or non-human animal, preferably mammal. The treatment may be in respect of an existing condition or may be prophylactic (preventative treatment).

As used herein, a "tumour" is an abnormal growth of tissue. It may be localised (benign) or invade nearby tissues (malignant) or distant tissues (metastatic). Tumours include neoplastic growths which cause cancer and include oesophageal, colorectal, gastric, breast and endometrial tumours, as well as cancerous tissues or cell lines including, but not limited to, leukaemic cells. As used herein, "tumour" also includes within its scope endometriosis.

The term "antibody" as used herein refers to immunoglobulin molecules and immunologically active portions of immunoglobulin molecules, i.e., molecules that contain an antigen binding site that specifically binds an antigen, whether natural or partly or wholly synthetically produced. The term also covers any polypeptide or protein having a binding domain which is, or is homologous to, an antibody binding domain. These can be derived from natural sources, or they may be partly or wholly synthetically produced. Examples of antibodies are the immunoglobulin isotypes (e.g., IgG, IgE, IgM, IgD and IgA) and their isotypic subclasses; fragments which comprise an antigen binding domain such as Fab, scFv, Fv, dAb, Fd; and diabodies. Antibodies may be polyclonal or monoclonal. A monoclonal antibody may be referred to herein as "mab".

It is possible to take monoclonal and other antibodies and use techniques of recombinant DNA technology to produce other antibodies or chimeric molecules which retain the specificity of the original antibody. Such techniques may involve introducing DNA encoding the immunoglobulin variable region, or the complementary determining regions (CDRs), of an antibody to the constant regions, or constant regions plus framework regions, of a different immunoglobulin. See, for instance, EP-A-184187, GB 2188638A or EP-A-239400. A hybridoma or other cell producing an antibody may be subject to genetic mutation or other changes, which may or may not alter the binding specificity of antibodies produced.

As antibodies can be modified in a number of ways, the term "antibody" should be construed as covering any specific binding member or substance having a binding domain with the required specificity. Thus, this term covers antibody fragments, derivatives, functional equivalents and homologues of antibodies, humanised antibodies, including any polypeptide comprising an immunoglobulin binding domain, whether natural or wholly or partially synthetic. Chimeric molecules comprising an immunoglobulin binding domain, or equivalent, fused to another polypeptide are therefore included. Cloning and expression of chimeric antibodies are described in EP-A-0120694 and EP-A-0125023. A humanised antibody may be a modified antibody having the variable regions of a non-human, e.g. murine, antibody and the constant region of a human antibody. Methods for making humanised antibodies are described in, for example, U.S. Pat. No. 5,225,539.

It has been shown that fragments of a whole antibody can perform the function of binding antigens. Examples of binding fragments are: (i) the Fab fragment consisting of VL, VH, CL and CH1 domains; (ii) the Fd fragment consisting of the VH and CH1 domains; (iii) the Fv fragment consisting of the VL and VH domains of a single antibody; (iv) the dAb fragment (Ward, E. S. et al., *Nature* 341:544-546 (1989)) which consists of a VH domain; (v) isolated CDR regions; (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site (Bird et al., *Science* 242:423-426 (1988); Huston et al., *PNAS USA* 85:5879-5883 (1988)); (viii) bispecific single chain Fv dimers (PCT/US92/09965) and (ix) "diabodies", multivalent or multispecific fragments constructed by gene fusion (WO94/13804; P. Hollinger et al., *Proc. Natl. Acad. Sci. USA* 90: 6444-6448 (1993)).

Diabodies are multimers of polypeptides, each polypeptide comprising a first domain comprising a binding region of an immunoglobulin light chain and a second domain comprising a binding region of an immunoglobulin heavy chain, the two domains being linked (e.g. by a peptide linker) but unable to associated with each other to form an antigen binding site: antigen binding sites are formed by the association of the first domain of one polypeptide within the multimer with the second domain of another polypeptide within the multimer (WO94/13804).

Where bispecific antibodies are to be used, these may be conventional bispecific antibodies, which can be manufactured in a variety of ways (Hollinger & Winter, *Current Opinion Biotechnol.* 4:446-449 (1993)), e.g. prepared chemically or from hybrid hybridomas, or may be any of the bispecific antibody fragments mentioned above. It may be preferable to use scFv dimers or diabodies rather than whole antibodies. Diabodies and scFv can be constructed without an Fc region, using only variable domains, potentially reducing the effects of anti-idiotypic reaction. Other forms of bispecific antibodies include the single chain "Janusins" described in Traunecker et al., *EMBO Journal* 10:3655-3659 (1991).

Bispecific diabodies, as opposed to bispecific whole antibodies, may also be useful because they can be readily constructed and expressed in *E. coli*. Diabodies (and many other polypeptides such as antibody fragments) of appropriate binding specificities can be readily selected using phage display (WO94/13804) from libraries. If one arm of the diabody is to be kept constant, for instance, with a specificity directed against antigen X, then a library can be made where the other arm is varied and an antibody of appropriate specificity selected.

An "antigen binding domain" is the part of an antibody which comprises the area which specifically binds to and is complementary to part or all of an antigen. Where an antigen is large, an antibody may only bind to a particular part of the antigen, which part is termed an epitope. An antigen binding domain may be provided by one or more antibody variable domains. An antigen binding domain may comprise an antibody light chain variable region (VL) and an antibody heavy chain variable region (VH).

"Specific" is generally used to refer to the situation in which one member of a specific binding pair will not show any significant binding to molecules other than its specific binding partner(s), and, e.g., has less than about 30%, preferably 20%, 10%, or 1% cross-reactivity with any other molecule. The term is also applicable where e.g. an antigen binding domain is specific for a particular epitope which is carried by a number of antigens, in which case, the specific binding member carrying the antigen binding domain will be able to bind to the various antigens carrying the epitope.

"Isolated" refers to the state in which specific binding members of the invention or nucleic acid encoding such binding members will preferably be, in accordance with the present invention. Members and nucleic acid will generally be free or substantially free of material with which they are naturally associated such as other polypeptides or nucleic acids with which they are found in their natural environment, or the environment in which they are prepared (e.g. cell culture) when such preparation is by recombinant DNA technology practised in vitro or in vivo. Specific binding members and nucleic acid may be formulated with diluents or adjuvants and still for practical purposes be isolated—for example, the members will normally be mixed with gelatin or other carriers if used to coat microtitre plates for use in immunoassays, or will be mixed with pharmaceutically acceptable carriers or diluents when used in diagnosis or therapy. Specific binding members may be glycosylated, either naturally or by systems of heterologous eukaryotic cells, or they may be (for example if produced by expression in a prokaryotic cell) unglycosylated.

By "substantially as set out" it is meant that the CDR regions of the invention will be either identical or highly homologous to the specified regions of FIGS. 1a and 1c. By "highly homologous" it is contemplated that from 1 to 5, from 1 to 4, from 1 to 3, 2 or 1 substitutions may be made in the CDRs.

The invention also includes within its scope polypeptides having the amino acid sequence as set out in FIG. 1a or 1c, polynucleotides having the nucleic acid sequences as set out in FIG. 1a or 1c and sequences having substantial identity thereto, for example, 70%, 80%, 85%, 90%, 95% or 99% identity thereto. The percent identity of two amino acid sequences or of two nucleic acid sequences is generally determined by aligning the sequences for optimal comparison purposes (e.g., gaps can be introduced in the first sequence for best alignment with the second sequence) and comparing the amino acid residues or nucleotides at corresponding positions. The "best alignment" is an alignment of two sequences that results in the highest percent identity. The percent identity is determined by comparing the number of identical amino acid residues or nucleotides within the sequences (i.e., % identity=number of identical positions/total number of positions×100).

The determination of percent identity between two sequences can be accomplished using a mathematical algorithm known to those of skill in the art. An example of a mathematical algorithm for comparing two sequences is the algorithm of Karlin and Altschul (1990) Proc. Natl. Acad. Sci. USA 87:2264-2268, modified as in Karlin and Altschul (1993) Proc. Natl. Acad. Sci. USA 90:5873-5877. The NBLAST and XBLAST programs of Altschul, et al. (1990) J. Mol. Biol. 215:403-410 have incorporated such an algorithm. BLAST nucleotide searches can be performed with the NBLAST program, score=100, wordlength=12 to obtain nucleotide sequences homologous to a nucleic acid molecules of the invention. BLAST protein searches can be performed with the XBLAST program, score=50, wordlength=3 to obtain amino acid sequences homologous to a protein molecules of the invention. To obtain gapped alignments for comparison purposes, Gapped BLAST can be utilized as described in Altschul et al. (1997) Nucleic Acids Res. 25:3389-3402. Alternatively, PSI-Blast can be used to perform an iterated search that detects distant relationships between molecules (Id.). When utilizing BLAST, Gapped BLAST, and PSI-Blast programs, the default parameters of the respective programs (e.g., XBLAST and NBLAST) can be used. See http://www.ncbi.nlm.nih.gov. Another example of a mathematical algorithm utilized for the comparison of sequences is the algorithm of Myers and Miller, CABIOS (1989). The ALIGN program (version 2.0) which is part of the GCG sequence alignment software package has incorporated such an algorithm. Other algorithms for sequence analysis known in the art include ADVANCE and ADAM as described in Torellis and Robotti (1994) Comput. Appl. Biosci., 10:3-5; and FASTA described in Pearson and Lipman (1988) Proc. Natl. Acad. Sci. 85:2444-8. Within FASTA, ktup is a control option that sets the sensitivity and speed of the search.

Isolated specific binding members of the present invention are capable of binding to a sialyltetraosyl carbohydrate, which may be a sialyltetraosylceramide or may be on a protein moiety. In one embodiment, the CDR3 regions, comprising the amino acid sequences substantially as set out as residues 117 to 127 of FIG. 1a (SEQ ID NO: 23) and 110 to 118 of FIG. 1c (SEQ ID NO: 27), are carried in a structure which allows the binding of these regions to a sialyltetraosyl carbohydrate.

The structure for carrying the CDR3s of the invention will generally be of an antibody heavy or light chain sequence or substantial portion thereof in which the CDR3 regions are located at locations corresponding to the CDR3 region of naturally-occurring VH and VL antibody variable domains encoded by rearranged immunoglobulin genes. The structures and locations of immunoglobulin variable domains may be determined by reference to Kabat, E. A., et al., *Sequences of Proteins of Immunological Interest*, 4$^{th}$ Edition, US Department of Health and Human Services, (1987), and updates thereof, now available on the Internet (http://immuno.bme.nwu/edu)).

The amino acid sequence substantially as set out as residues 117 to 127 of FIG. 1a (SEQ ID NO: 23) may be carried as the CDR3 in a human heavy chain variable domain or a substantial portion thereof, and the amino acid sequence substantially as set out as residues and 110 to 118 of FIG. 1c (SEQ ID NO: 27) may be carried as the CDR3 in a human light chain variable domain or a substantial portion thereof.

The variable domains may be derived from any germline or rearranged human variable domain, or may be a synthetic variable domain based on consensus sequences of known human variable domains. The CDR3-derived sequences of the invention may be introduced into a repertoire of variable domains lacking CDR3 regions, using recombinant DNA technology.

For example, Marks et al (*Bio/Technology* 10:779-783 (1992)) describe methods of producing repertoires of antibody variable domains in which consensus primers directed at or adjacent to the 5' end of the variable domain area are used in conjunction with consensus primers to the third framework region of human VH genes to provide a repertoire of VH variable domains lacking a CDR3. Marks et al further describe how this repertoire may be combined with a CDR3 of a particular antibody. Using analogous techniques, the CDR3-derived sequences of the present invention may be shuffled with repertoires of VH or VL domains lacking a CDR3, and the shuffled complete VH or VL domains combined with a cognate VL or VH domain to provide specific binding members of the invention. The repertoire may then be displayed in a suitable host system such as the phage display system of WO92/01047 so that suitable specific binding members may be selected. A repertoire may consist of from anything from $10^4$ individual members upwards, for example from $10^6$ to $10^8$ or $10^{10}$ members.

Analogous shuffling or combinatorial techniques are also disclosed by Stemmer (*Nature* 370:389-391 (1994)) who describes the technique in relation to a β-lactamase gene but observes that the approach may be used for the generation of antibodies.

A further alternative is to generate novel VH or VL regions carrying the CDR3-derived sequences of the invention using random mutagenesis of, for example, the SC104 VH or VL genes to generate mutations within the entire variable domain. Such a technique is described by Gram et al (*Proc. Natl. Acad. Sci. USA* 89:3576-3580 (1992)), who used error-prone PCR.

Another method which may be used is to direct mutagenesis to CDR regions of VH or VL genes. Such techniques are disclosed by Barbas et al (*Proc. Natl. Acad. Sci. USA* 91:3809-3813 (1994)) and Schier et al (*J. Mol. Biol.* 263:551-567 (1996)).

A substantial portion of an immunoglobulin variable domain will generally comprise at least the three CDR regions, together with their intervening framework regions. The portion may also include at least about 50% of either or both of the first and fourth framework regions, the 50% being the C-terminal 50% of the first framework region and the N-terminal 50% of the fourth framework region. Additional residues at the N-terminal or C-terminal end of the substantial part of the variable domain may be those not normally associated with naturally occurring variable domain regions. For example, construction of specific binding members of the present invention made by recombinant DNA techniques may result in the introduction of N- or C-terminal residues encoded by linkers introduced to facilitate cloning or other manipulation steps, including the introduction of linkers to join variable domains of the invention to further protein sequences including immunoglobulin heavy chains, other variable domains (for example in the production of diabodies) or protein labels as discussed in more detail below.

One embodiment of the invention provides specific binding members comprising a pair of binding domains based on the amino acid sequences for the VL and VH regions substantially as set out in FIGS. 1*a* (SEQ ID NO: 23) and 1*c* (SEQ ID NO: 27), i.e. amino acids 19 to 138 of FIG. 1*a* (SEQ ID NO: 23) and amino acids 23 to 128 of FIG. 1*c* (SEQ ID NO: 27). Single binding domains based on either of these sequences form further aspects of the invention. In the case of the binding domains based on the amino acid sequence for the VH region substantially set out in FIG. 1*a*, such binding domains may be used as targeting agents since it is known that immunoglobulin VH domains are capable of binding target antigens in a specific manner.

In the case of either of the single chain specific binding domains, these domains may be used to screen for complementary domains capable of forming a two-domain specific binding member which has in vivo properties as good as or equal to the SC104 antibody disclosed herein.

This may be achieved by phage display screening methods using the so-called hierarchical dual combinatorial approach as disclosed in WO92/01047 in which an individual colony containing either an H or L chain clone is used to infect a complete library of clones encoding the other chain (L or H) and the resulting two-chain specific binding member is selected in accordance with phage display techniques such as those described in that reference. This technique is also disclosed in Marks et al. ibid.

Specific binding members of the present invention may further comprise antibody constant regions or parts thereof. For example, specific binding members based on the VL region shown in FIG. 1*c* may be attached at their C-terminal end to antibody light chain constant domains including human Cκ or Cλ chains. Similarly, specific binding members based on VH region shown in FIG. 1*a* or 1*b* may be attached at their C-terminal end to all or part of an immunoglobulin heavy chain derived from any antibody isotype, e.g. IgG, IgA, IgE and IgM and any of the isotype sub-classes, particularly IgG1 and IgG4.

SC104 has been demonstrated to cause the death of tumour cell-lines in suspension, and to cause the specific onset of apoptosis or programmed cell-death in colorectal tumours and cells derived from disaggregated tumour tissue. Thus, specific binding members of the present invention can be used as therapeutics to inhibit the growth of, or induce apoptosis in, tumours. Apoptosis is the process by which a cell actively commits suicide. It is now well recognised that apoptosis is essential in many aspects of normal development and is required for maintaining tissue homeostasis. However, cell death by suicide, sometimes referred to as programmed cell death, is needed to destroy cells that represent a threat to the integrity of the organism. There are two different mechanisms by which a cell commits suicide by apoptosis. One is triggered by signals arising from within the cell, the other by external signals (e.g. molecules) which bind to receptors at the cell surface.

Specific binding members of the present invention can be used in methods of diagnosis and treatment of tumours in human or animal subjects.

When used in diagnosis, specific binding members of the invention may be labelled with a detectable label, for example a radiolabel such as $^{131}$I or $^{99}$Tc, which may be attached to specific binding members of the invention using conventional chemistry known in the art of antibody imaging. Labels also include enzyme labels such as horseradish peroxidase. Labels further include chemical moieties such as biotin which may be detected via binding to a specific cognate detectable moiety, e.g. labelled avidin.

Although specific binding members of the invention have in themselves been shown to be effective in killing cancer cells, they may additionally be labelled with a functional label. Functional labels include substances which are designed to be targeted to the site of cancer to cause destruction thereof. Such functional labels include toxins such as ricin and enzymes such as bacterial carboxypeptidase or nitroreductase, which are capable of converting prodrugs into active drugs. In addition, the specific binding members may be attached or otherwise associated with chemotherapeutic or cytotoxic agents, such as calicheamicin, or radiolabels, such as $^{90}$Y or $^{131}$I.

Furthermore, the specific binding members of the present invention may be administered alone or in combination with other treatments, either simultaneously or sequentially, dependent upon the condition to be treated. Thus, the present invention further provides products containing a specific binding member of the present invention and an active agent as a combined preparation for simultaneous, separate or sequential use in the treatment of a tumour. Active agents may include chemotherapeutic or cytotoxic agents including, 5-Fluorouracil, cisplatin, Mitomycin C, oxaliplatin and tamoxifen, which may operate synergistically with the binding members of the present invention. Other active agents may include suitable doses of pain relief drugs such as non-steroidal anti-inflammatory drugs (e.g. aspirin, paracetamol, ibuprofen or ketoprofen) or opitates such as morphine, or anti-emetics.

Whilst not wishing to be bound by theory, the ability of the binding members of the invention to synergise with an active agent to enhance tumour killing may not be due to immune effector mechanisms but rather may be a direct consequence of the binding member binding to cell surface bound sialyltetraosyl carbohydrate.

Specific binding members of the present invention will usually be administered in the form of a pharmaceutical composition, which may comprise at least one component in addition to the specific binding member. The pharmaceutical composition may comprise, in addition to active ingredient, a pharmaceutically acceptable excipient, diluent, carrier, buffer, stabiliser or other materials well known to those skilled in the art. Such materials should be non-toxic and should not interfere with the efficacy of the active ingredient. The precise nature of the carrier or other material will depend on the route of administration, which may be oral, or by injection, e.g. intravenous.

It is envisaged that injections will be the primary route for therapeutic administration of the compositions although delivery through a catheter or other surgical tubing is also used. Some suitable routes of administration include intravenous, subcutaneous and intramuscular administration. Liquid formulations may be utilised after reconstitution from powder formulations.

For intravenous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

Pharmaceutical compositions for oral administration may be in tablet, capsule, powder or liquid form. A tablet may comprise a solid carrier such as gelatin or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included. Where the formulation is a liquid it may be, for example, a physiologic salt solution containing non-phosphate buffer at pH 6.8-7.6, or a lyophilised powder.

The composition may also be administered via microspheres, liposomes, other microparticulate delivery systems or sustained release formulations placed in certain tissues including blood. Suitable examples of sustained release carriers include semi-permeable polymer matrices in the form of shared articles, e.g. suppositories or microcapsules. Implantable or microcapsular sustained release matrices include polylactides (U.S. Pat. No. 3,773,919; EP-A-0058481) copolymers of L-glutamic acid and gamma ethyl-L-glutamate (Sidman et al, Biopolymers 22(1): 547-556, 1985), poly (2-hydroxyethyl-methacrylate) or ethylene vinyl acetate (Langer et al, J. Biomed. Mater. Res. 15: 167-277, 1981, and Langer, Chem. Tech. 12:98-105, 1982). Liposomes containing the polypeptides are prepared by well-known methods: DE 3,218,121A; Epstein et al, PNAS USA, 82: 3688-3692, 1985; Hwang et al, PNAS USA, 77: 4030-4034, 1980; EP-A-0052522; E-A-0036676; EP-A-0088046; EP-A-0143949; EP-A-0142541; JP-A-83-11808; U.S. Pat. Nos. 4,485,045 and 4,544,545. Ordinarily, the liposomes are of the small (about 200-800 Angstroms) unilamellar type in which the lipid content is greater than about 30 mol. % cholesterol, the selected proportion being adjusted for the optimal rate of the polypeptide leakage.

The composition may be administered in a localised manner to a tumour site or other desired site or may be delivered in a manner in which it targets tumour or other cells.

The compositions are preferably administered to an individual in a "therapeutically effective amount", this being sufficient to show benefit to the individual. The actual amount administered, and rate and time-course of administration, will depend on the nature and severity of what is being treated. Prescription of treatment, e.g. decisions on dosage etc, is within the responsibility of general practitioners and other medical doctors, and typically takes account of the disorder to be treated, the condition of the individual patient, the site of delivery, the method of administration and other factors known to practitioners. The compositions of the invention are particularly relevant to the treatment of existing tumours, especially cancer, and in the prevention of the recurrence of such conditions after initial treatment or surgery. Examples of the techniques and protocols mentioned above can be found in Remington's Pharmaceutical Sciences, 16$^{th}$ edition, Oslo, A. (ed), 1980.

The optimal dose can be determined by physicians based on a number of parameters including, for example, age, sex, weight, severity of the condition being treated, the active ingredient being administered and the route of administration. In general, a serum concentration of polypeptides and antibodies that permits saturation of receptors is desirable. A concentration in excess of approximately 0.1 nM is normally sufficient. For example, a dose of 100 mg/m$^2$ of antibody provides a serum concentration of approximately 20 nM for approximately eight days.

As a rough guideline, doses of antibodies may be given weekly in amounts of 10-300 mg/m$^2$. Equivalent doses of antibody fragments should be used at more frequent intervals in order to maintain a serum level in excess of the concentration that permits saturation of the sialyltetraosyl carbohydrate.

The dose of the composition will be dependent upon the properties of the binding member, e.g. its binding activity and in vivo plasma half-life, the concentration of the polypeptide in the formulation, the administration route, the site and rate of dosage, the clinical tolerance of the patient involved, the pathological condition afflicting the patient and the like, as is well within the skill of the physician. For example, doses of 300 µg of antibody per patient per administration are preferred, although dosages may range from about 10 µg to 6 mg per dose. Different dosages are utilised during a series of sequential inoculations; the practitioner may administer an initial inoculation and then boost with relatively smaller doses of antibody.

This invention is also directed to optimise immunisation schedules for enhancing a protective immune response against cancer.

The binding members of the present invention may be generated wholly or partly by chemical synthesis. The binding members can be readily prepared according to well-established, standard liquid or, preferably, solid-phase peptide synthesis methods, general descriptions of which are broadly available (see, for example, in J. M. Stewart and J. D. Young, Solid Phase Peptide Synthesis, $2^{nd}$ edition, Pierce Chemical Company, Rockford, Ill. (1984), in M. Bodanzsky and A. Bodanzsky, The Practice of Peptide Synthesis, Springer Verlag, New York (1984); and Applied Biosystems 430A Users Manual, ABI Inc., Foster City, Calif.), or they may be prepared in solution, by the liquid phase method or by any combination of solid-phase, liquid phase and solution chemistry, e.g. by first completing the respective peptide portion and then, if desired and appropriate, after removal of any protecting groups being present, by introduction of the residue X by reaction of the respective carbonic or sulfonic acid or a reactive derivative thereof.

Another convenient way of producing a binding member according to the present invention is to express the nucleic acid encoding it, by use of nucleic acid in an expression system.

The present invention further provides an isolated nucleic acid encoding a specific binding member of the present invention. Nucleic acid includes DNA and RNA. In a preferred aspect, the present invention provides a nucleic acid which codes for a specific binding member of the invention as defined above. Examples of such nucleic acid are shown in FIGS. 1a, 1b and 1c. The skilled person will be able to determine substitutions, deletions and/or additions to such nucleic acids which will still provide a specific binding member of the present invention.

The present invention also provides constructs in the form of plasmids, vectors, transcription or expression cassettes which comprise at least one nucleic acid as described above. The present invention also provides a recombinant host cell which comprises one or more constructs as above. As mentioned, a nucleic acid encoding a specific binding member of the invention forms an aspect of the present invention, as does a method of production of the specific binding member which method comprises expression from encoding nucleic acid therefor. Expression may conveniently be achieved by culturing under appropriate conditions recombinant host cells containing the nucleic acid. Following production by expression, a specific binding member may be isolated and/or purified using any suitable technique, then used as appropriate.

Systems for cloning and expression of a polypeptide in a variety of different host cells are well known. Suitable host cells include bacteria, mammalian cells, yeast and baculovirus systems. Mammalian cell lines available in the art for expression of a heterologous polypeptide include Chinese hamster ovary cells, HeLa cells, baby hamster kidney cells, NSO mouse melanoma cells and many others. A common, preferred bacterial host is E. coli. The expression of antibodies and antibody fragments in prokaryotic cells such as E. coli is well established in the art. For a review, see for example Plückthun, Bio/Technology 9:545-551 (1991). Expression in eukaryotic cells in culture is also available to those skilled in the art as an option for production of a specific binding member, see for recent review, for example Reff, Curr. Opinion Biotech. 4:573-576 (1993); Trill et al., Curr. Opinion Biotech. 6:553-560 (1995).

Suitable vectors can be chosen or constructed, containing appropriate regulatory sequences, including promoter sequences, terminator sequences, polyadenylation sequences, enhancer sequences, marker genes and other sequences as appropriate. Vectors may be plasmids, viral e.g. 'phage, or phagemid, as appropriate. For further details see, for example, Sambrook et al., Molecular Cloning: A Laboratory Manual: $2^{nd}$ Edition, Cold Spring Harbor Laboratory Press (1989). Many known techniques and protocols for manipulation of nucleic acid, for example in preparation of nucleic acid constructs, mutagenesis, sequencing, introduction of DNA into cells and gene expression, and analysis of proteins, are described in detail in Ausubel et al. eds., Short Protocols in Molecular Biology, $2^{nd}$ Edition, John Wiley & Sons (1992).

Thus, a further aspect of the present invention provides a host cell containing nucleic acid as disclosed herein. A still further aspect provides a method comprising introducing such nucleic acid into a host cell. The introduction may employ any available technique. For eukaryotic cells, suitable techniques may include calcium phosphate transfection, DEAE-Dextran, electroporation, liposome-mediated transfection and transduction using retrovirus or other virus, e.g. vaccinia or, for insect cells, baculovirus. For bacterial cells, suitable techniques may include calcium chloride transformation, electroporation and transfection using bacteriophage. The introduction may be followed by causing or allowing expression from the nucleic acid, e.g. by culturing host cells under conditions for expression of the gene.

In one embodiment, the nucleic acid of the invention is integrated into the genome (e.g. chromosome) of the host cell. Integration may be promoted by inclusion of sequences which promote recombination with the genome, in accordance with standard techniques.

The present invention also provides a method which comprises using a construct as stated above in an expression system in order to express a specific binding member or polypeptide as above.

Preferred features of each aspect of the invention are as for each of the other aspects mutatis mutandis. The prior art documents mentioned herein are incorporated to the fullest extent permitted by law.

The invention will now be described further in the following non-limiting examples. Reference is made to the accompanying drawings in which:

FIG. 1a shows the nucleic acid and amino acid sequences of the SC104 antibody heavy chain variable domain and a part of the constant region, FIG. 1b shows the identical sequence to that outlined in FIG. 1a but the Kabat numbering system has been employed, and FIG. 1c shows the nucleic acid and amino acid sequences of the SC104 antibody light chain variable domain and a part of the constant region. FIG. 1d demonstrates that the chimeric version of the SC104 antibody, produced by a transfected cell line, binds the target cell line.

Figure 2A:
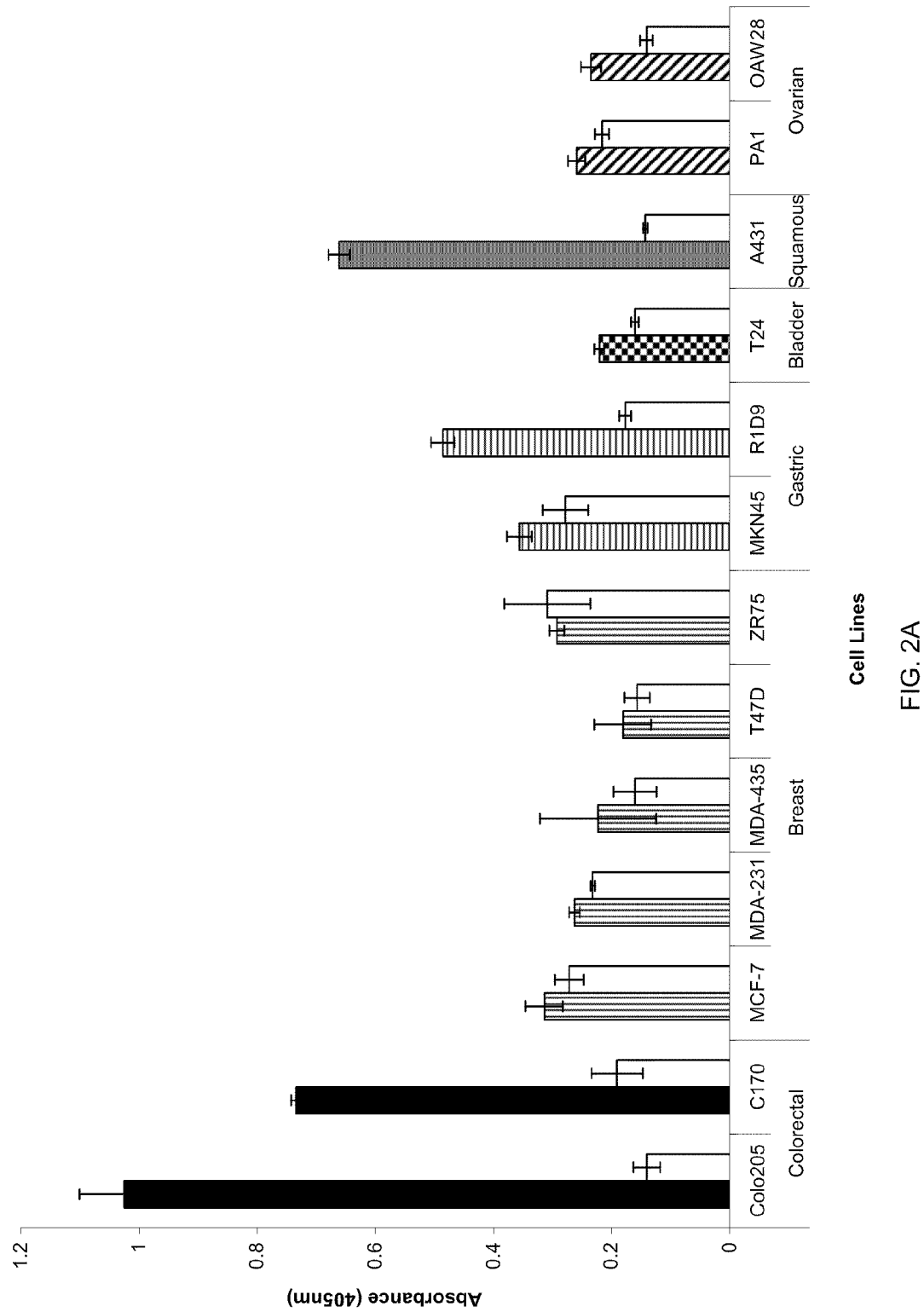
Figure 2B:
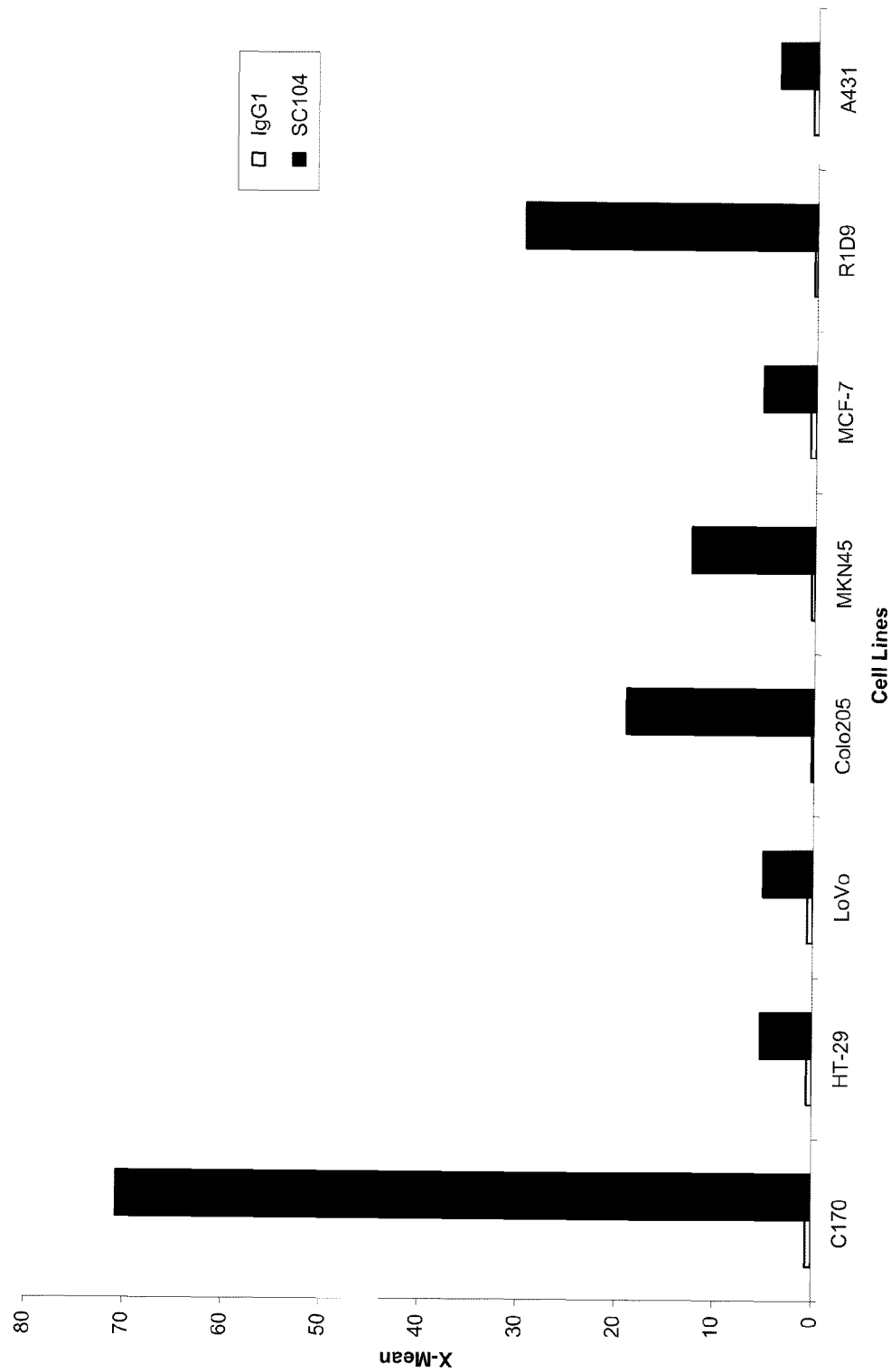

FIG. 2a is a graph demonstrating binding of SC104 to a panel of cell lines (Colo205, C170, MCF-7, MDA-231, MDA-435, T47D, ZR75, MKN45, RID9, T24, A431, PA1 and OAW28 (obtained from ECACC)). Cells were stained by ELISA and results are expressed as absorbance (405 nm) for each cell line. FIG. 2b is a graph demonstrating binding of SC104 to the following cell lines: C170, HT-29, LoVo, Colo205, MKN45, RID9 and A431. Cells were stained by indirect immunofluorescence and analysed by flow cytometry. Results are expressed as X-mean for each cell line. SC101/29 is supplied by Scancell as a positive control and recognises Lewis$^{y/b}$. An isotyped matched antibody is used as a negative control.

Figure 3:
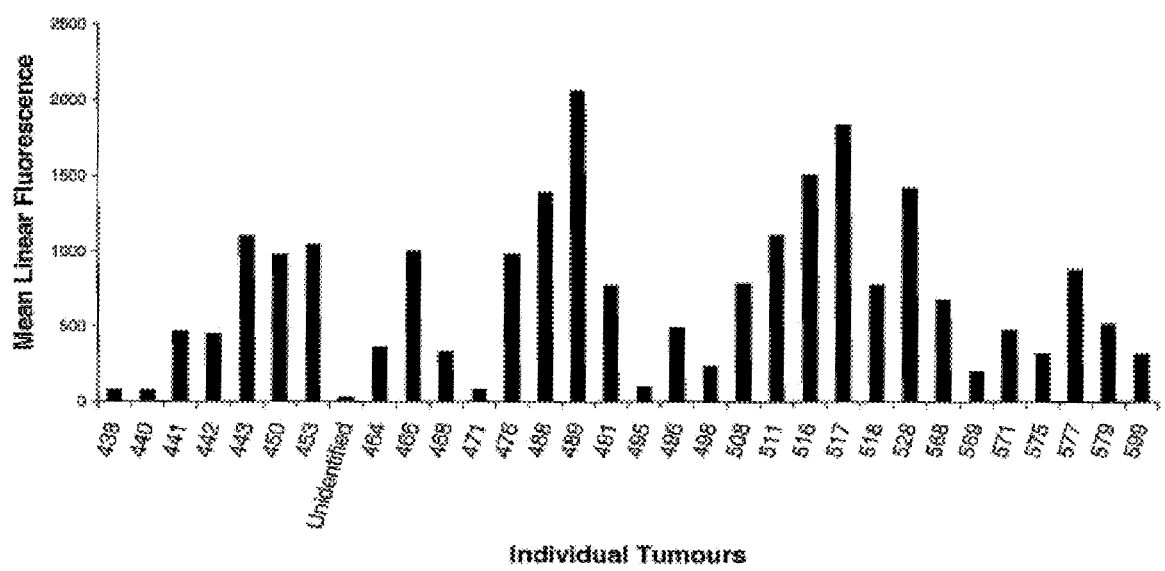

FIG. 3 is a graph demonstrating binding of monoclonal antibodies to freshly disaggregated colorectal tumour cells, as assayed by indirect immunofluorescence and analysed by flow cytometry. Each point refers to the mean fluorescence for an individual tumour.

Figure 4:
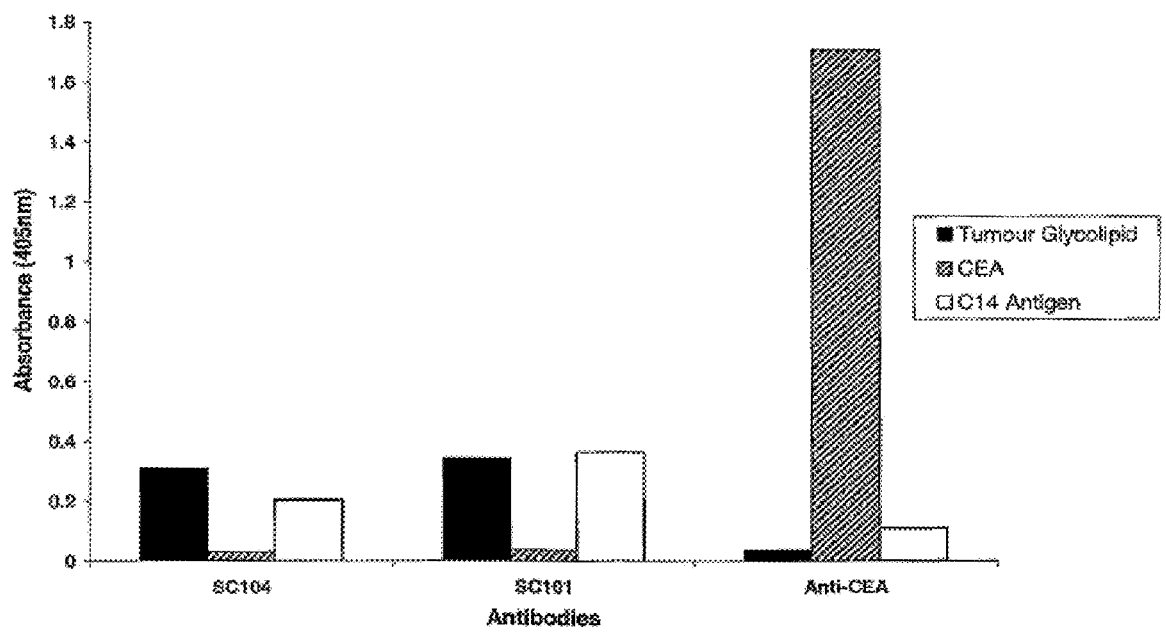

FIG. 4 is a graph demonstrating binding of SC104 mab to purified CEA, C14 antigen and tumour glycolipid extract. The C14 antigen (90 KDa glycoprotein purified from saliva by affinity chromatography on C14 monoclonal), CEA (180 KDa glycoprotein purified from colorectal tumour live metastases by affinity chromatography with 365 mab) and glycolipid extract (glycolipid extracted in 3:1 methanol chloroform w/v from colorectal tumours) were dried onto microtitre plates by overnight incubation at 37° C. Binding of SC104 mab was assayed by ELISA and results expressed as absorbance 405 nm. SC101 and anti-CEA antibodies are included as positive controls.

Figure 5:
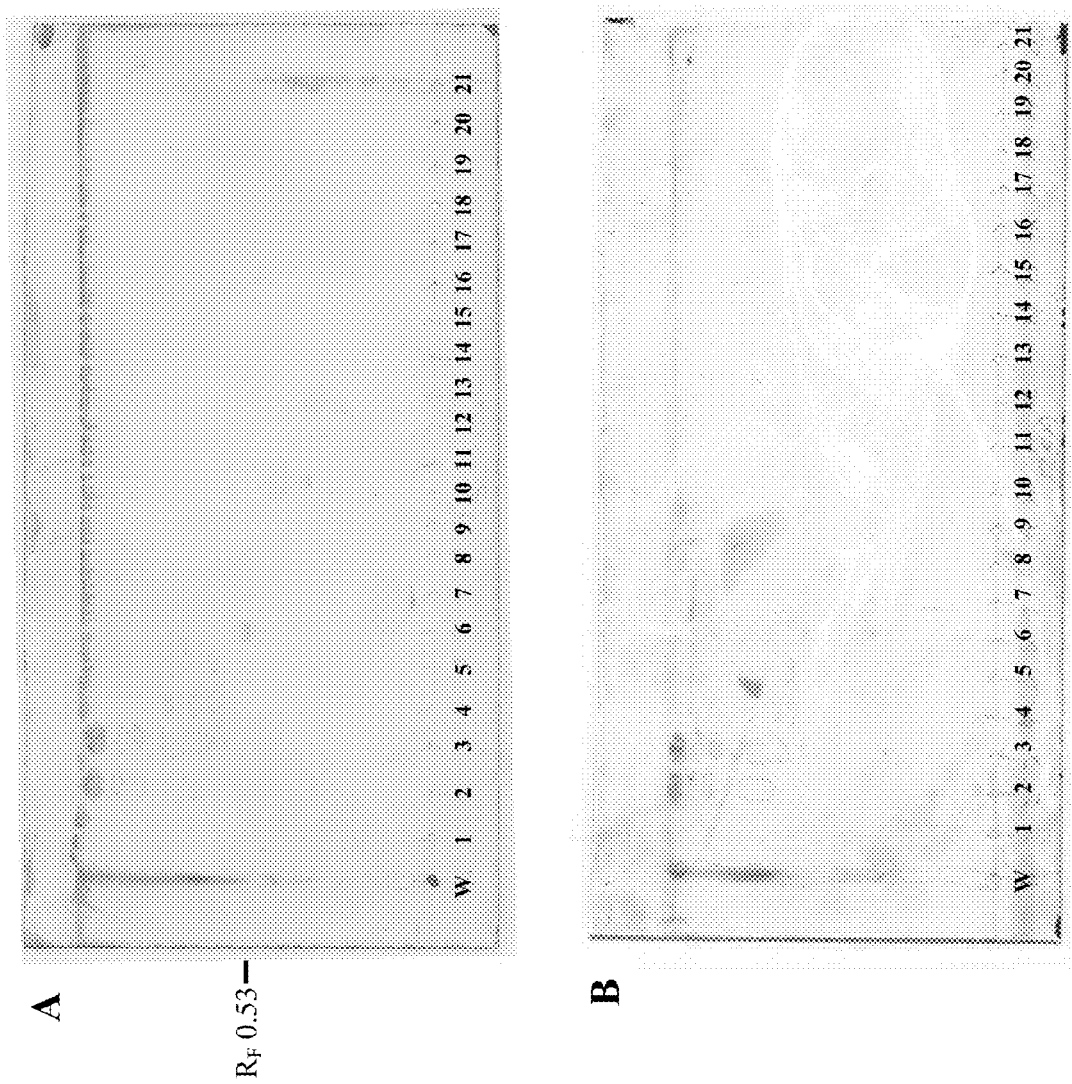

FIG. 5 shows HPTLC plates showing A. SC104 immunostaining of fractions collected from 36 ml bed volume column. Lane W is the whole C170 extract prior to fractionation. The first 6×10 ml fractions collected are spotted in lanes 1 to 6 while the last 14 lanes represent the next 14×3 ml fractions collected. The SC104 antigen can be located in fraction 6, with $R_F$ 0.53. B. Secondary antibody only shows no band indicating that binding is specific to SC104.

Figure 6:
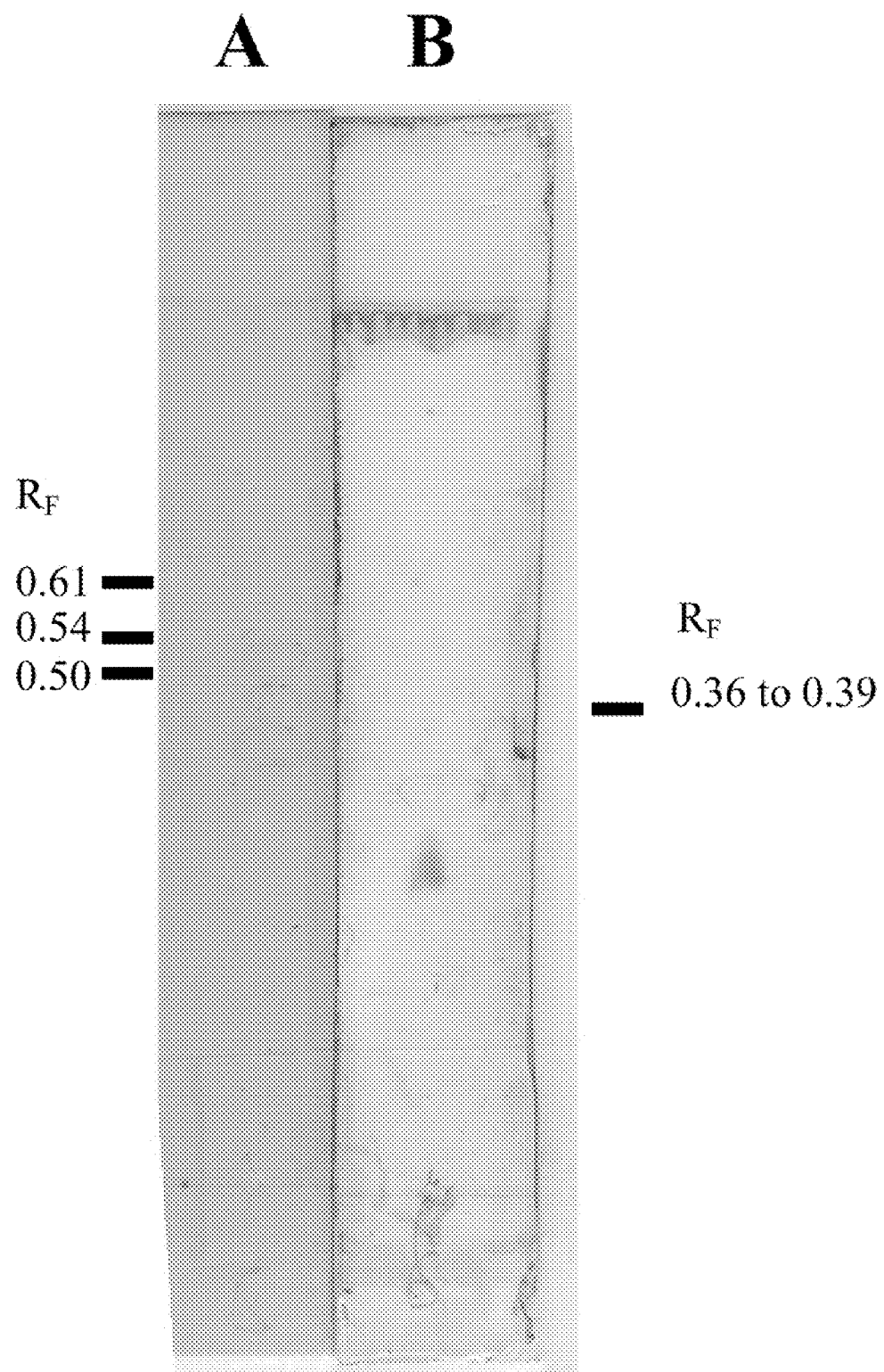

FIG. 6 is a HPTLC plate showing (A) orcinol staining of fraction 6 revealing three bands with RF values between $R_F$ 0.50 and 0.61. (B) SC104 immunostaining of the same fraction gave three tight bands between $R_F$ 0.36 and 0.39.

Figure 7:
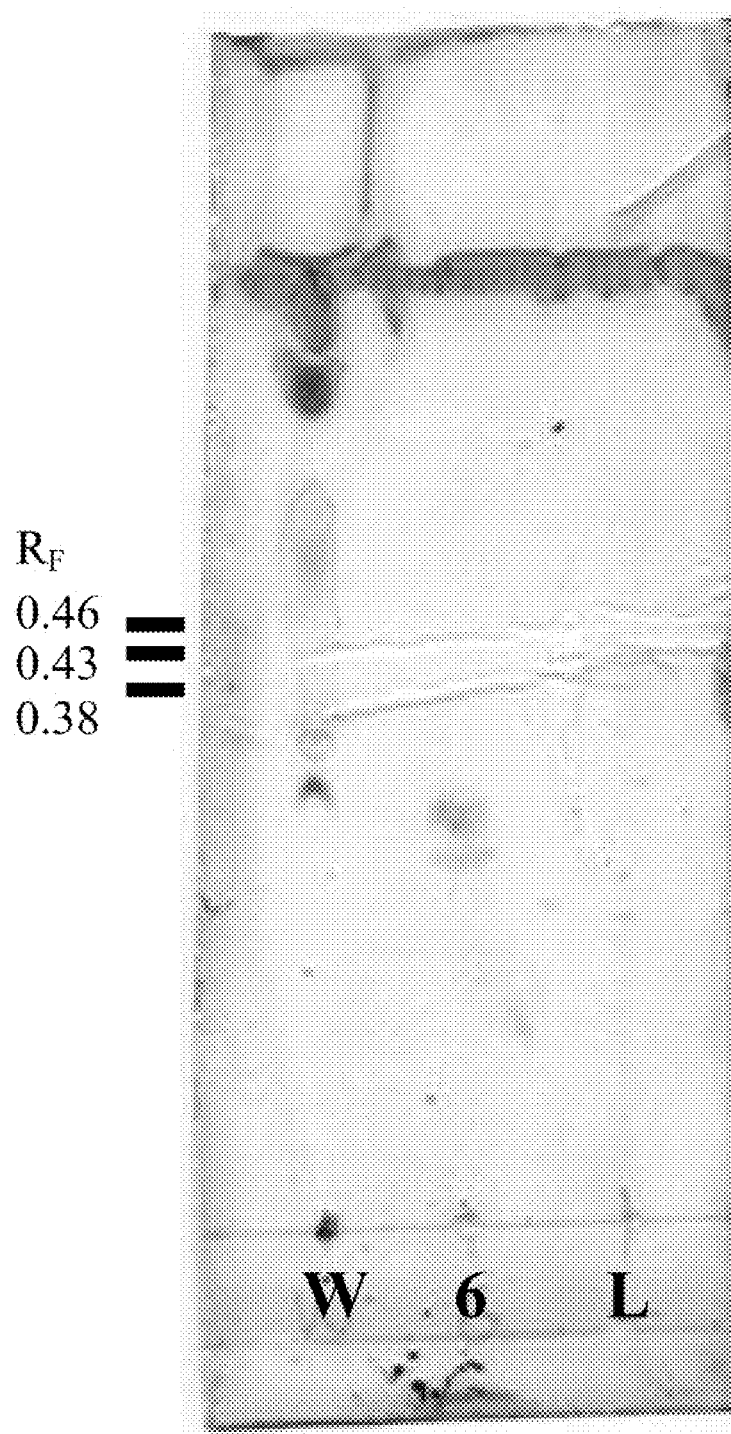

FIG. 7 is a HPTLC plate showing SC104 immunostaining of whole C170 extract (lane W), fraction 6 (lane 6) and de-glycosylated lipid (lane L). Antigen was observed in the whole extract and fraction 6 ($R_F$ 0.38 to 0.46), but no longer detected in the lipid fraction following de-glycosylation by ceramide glycanase.

Figure 8:
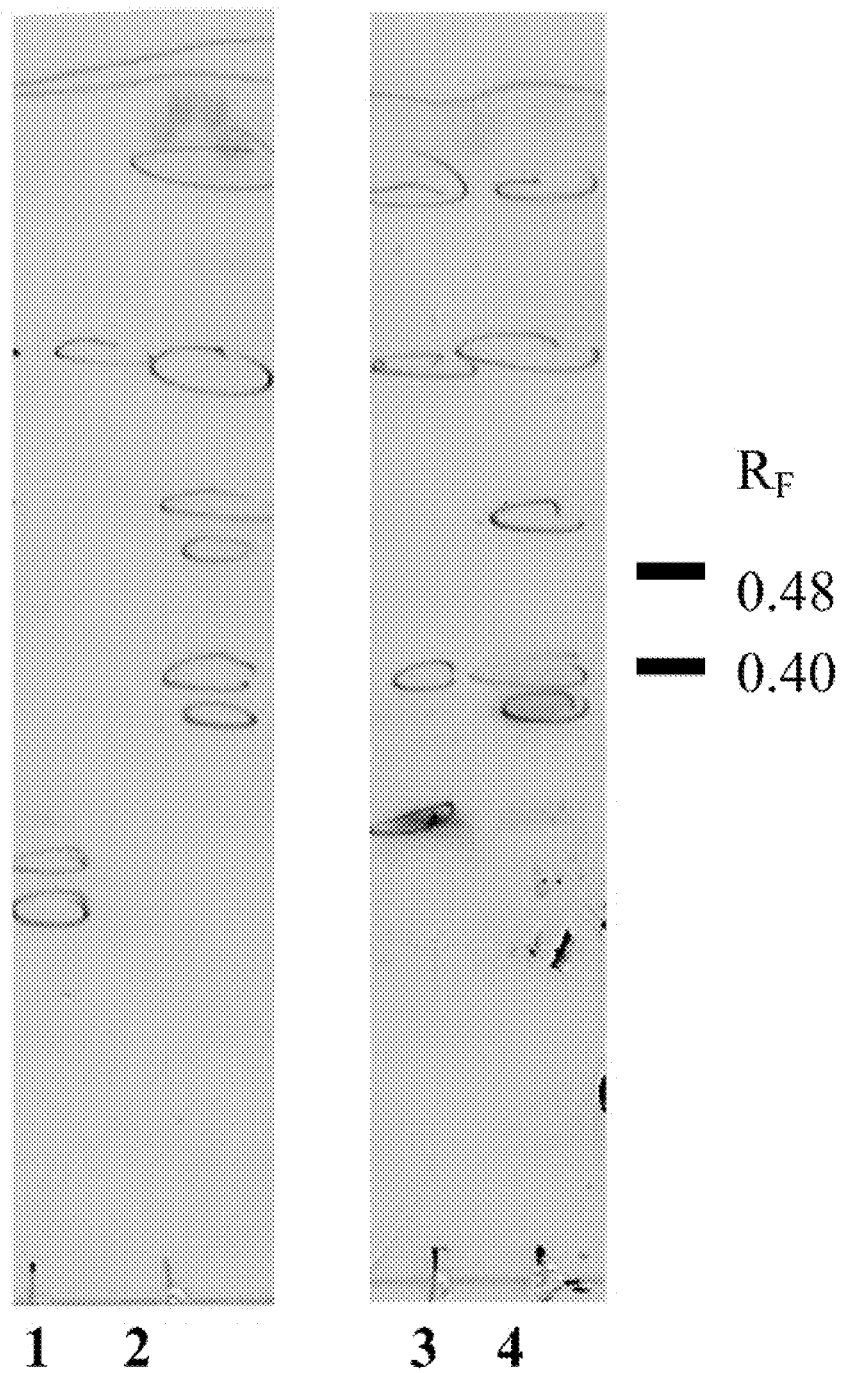

FIG. 8 is a HPTLC plate showing SC104 immunostaining of partially purified antigen. Pencil marks indicate the location of lipid detected by iodine vapour staining Lanes 1 and 2 contain the ceramide glycanase treated antigen following separation into the aqueous and organic phases respectively. Released oligosaccharides partition into the aqueous phase and free lipids into the organic phase. Any undigested glycolipids will partition into either phase depending on overall polarity. Lanes 3 and 4 are the same aqueous and organic partitioned fractions in the absence of ceramide glycanase. Antigen is detected ($R_F$ 0.48 and 0.40) prior to de-glycosylation but not following oligosaccharide removal.

Figure 9:
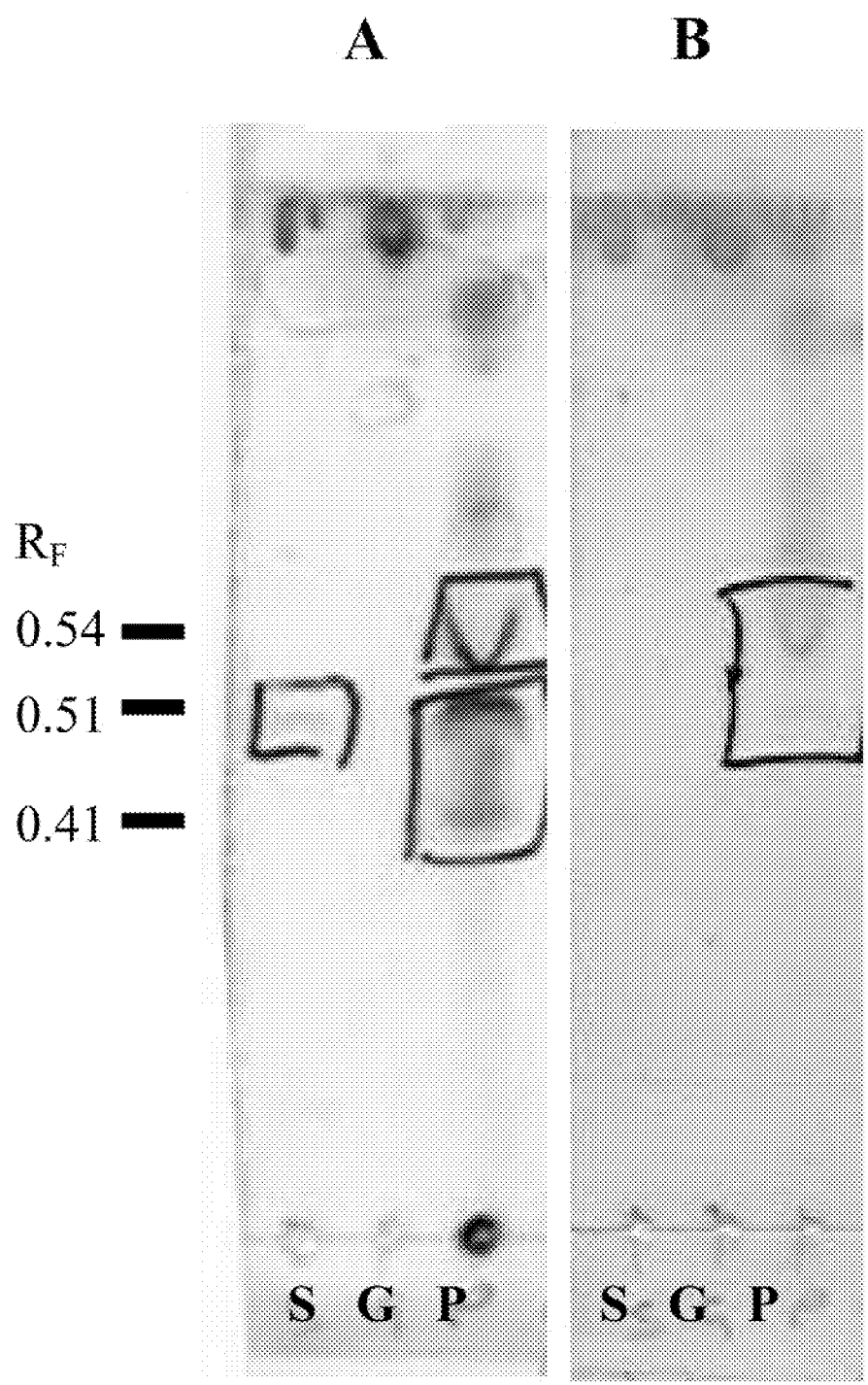

FIG. 9 is a HPTLC plate showing SC104 immunostaining (A) and orcinol staining of (B) of simple (lane S), glycolipid (lane G) and phospholipid (lane P) fractions from C170 cells. Antigen is detected in the simple and phospholipid fractions ($R_F$ 0.54, 0.51 and 0.41) but not the neutral glycolipid portion. Orcinol staining reveals two distinct bands in the phospholipid fraction ($R_F$ 0.54 and 0.51) that co-migrate with the antigen.

Figure 10:
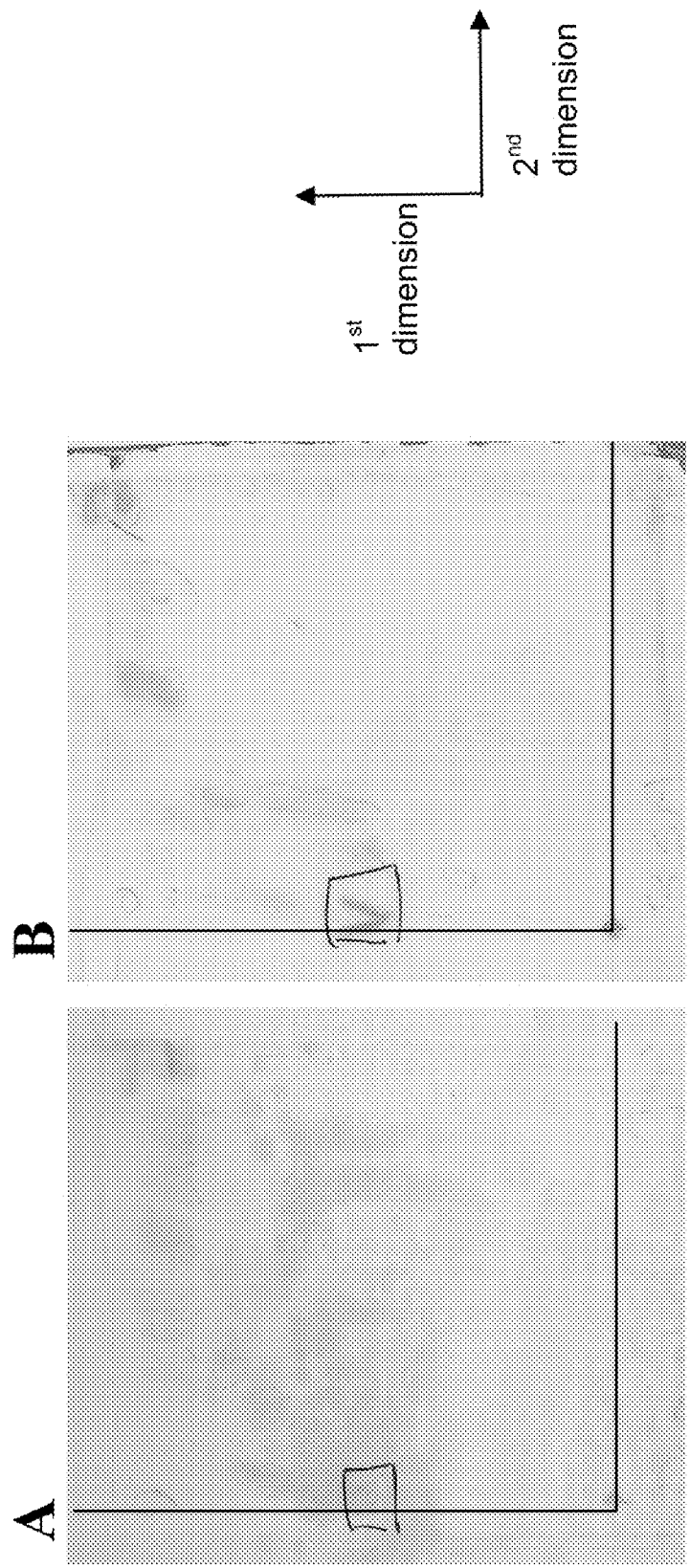

FIG. 10 shows 2-dimensional HPTLC plates of C170 whole lipid extract followed by orcinol (A) or SC104 immunostaining (B). The first dimension was developed in 50:40:10 chloroform:methanol:CaCl$_2$ (0.5% w/v) and the second dimension in 10:4:2:2:1 chloroform:acetone:methanol:acetic acid:water. The antigen migrates with RF 0.48 in the 1$^{st}$ dimension and does not migrate in the 2$^{nd}$. An orcinol stained band is again seen to co-migrate with the antigen.

Figure 11:
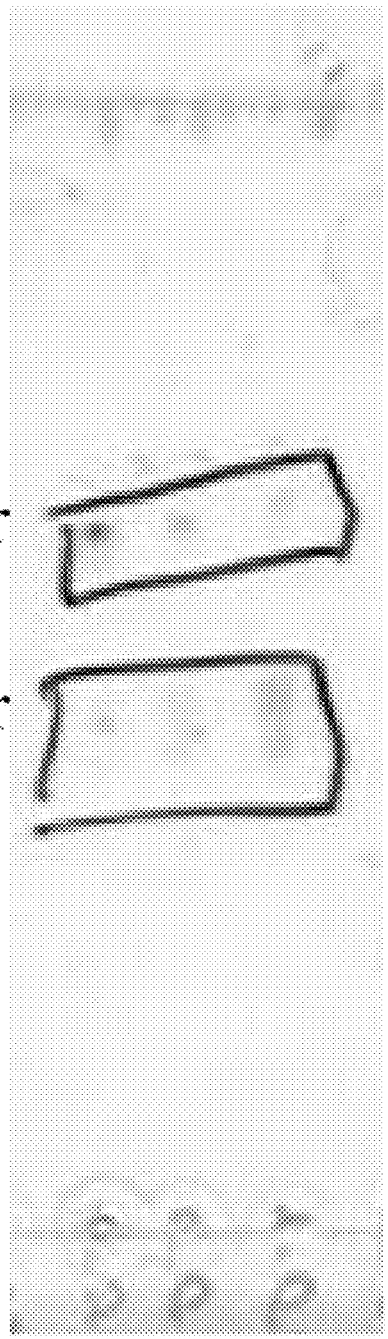

FIG. 11 is a HPTLC plate showing SC104 immunostaining of antigen with (lanes 1 and 2) and without (lane 3) de-sialylation by neuraminidase digestion. De-sialylation resulted in more intense staining of the less polar ($R_F$ 0.46) cluster and a decrease in staining of the more polar ($R_F$ 0.62) cluster.

Figure 12:
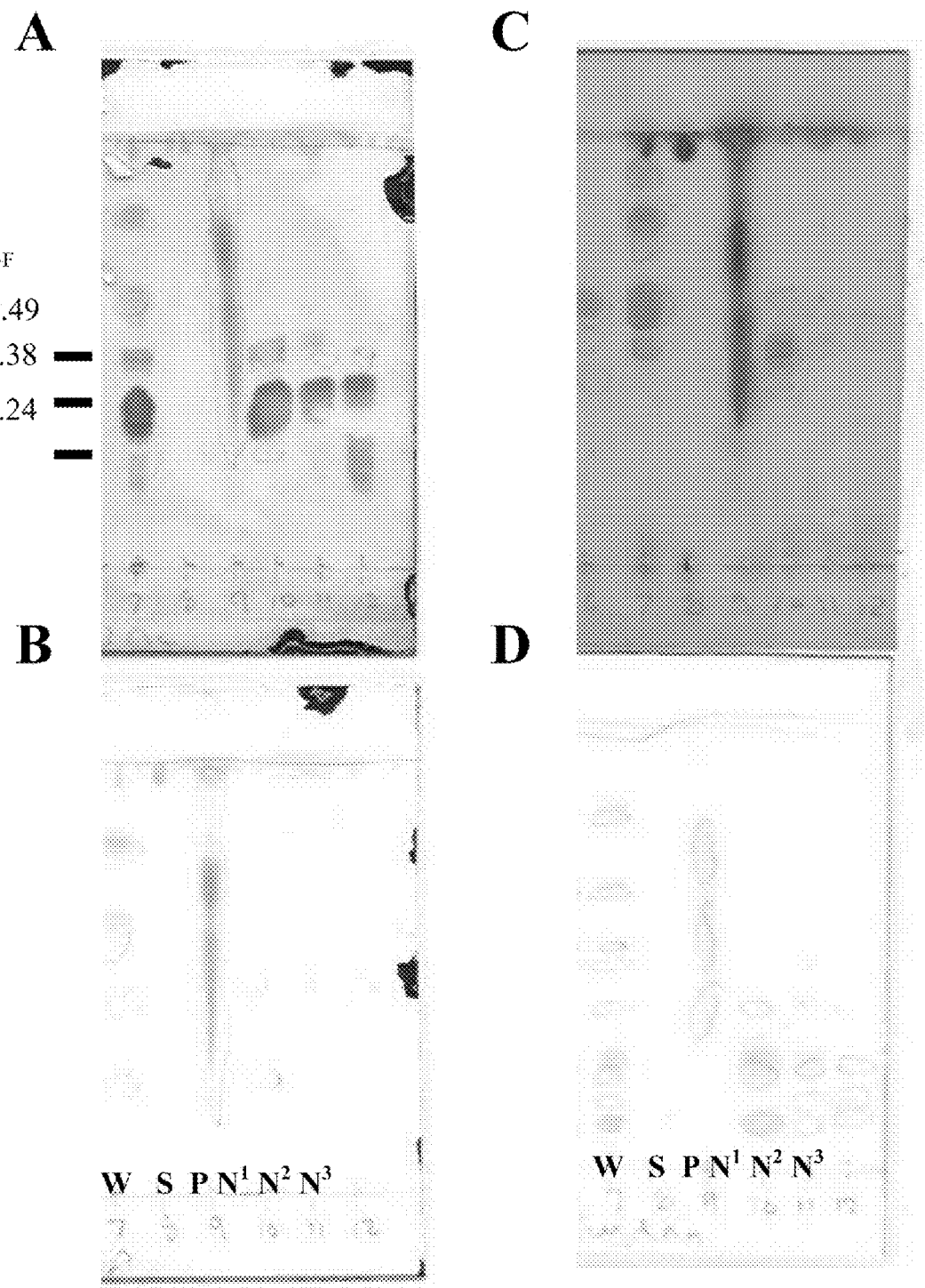

FIG. 12 shows a HPTLC plate of C170 lipid fractions from silica column. Plates were probed with SC104 (A), secondary antibody only (B) or stained with orcinol (C) or ninhydrin (D). Antigen was detected in the whole extract (lane W), and the sialylated glycolipid fractions (lanes $N^1$, $N^2$ and $N^3$). No antigen was observed in either the simple (lane S) or phospholipid/neutral glycolipid fraction (lane P).

Figure 13:
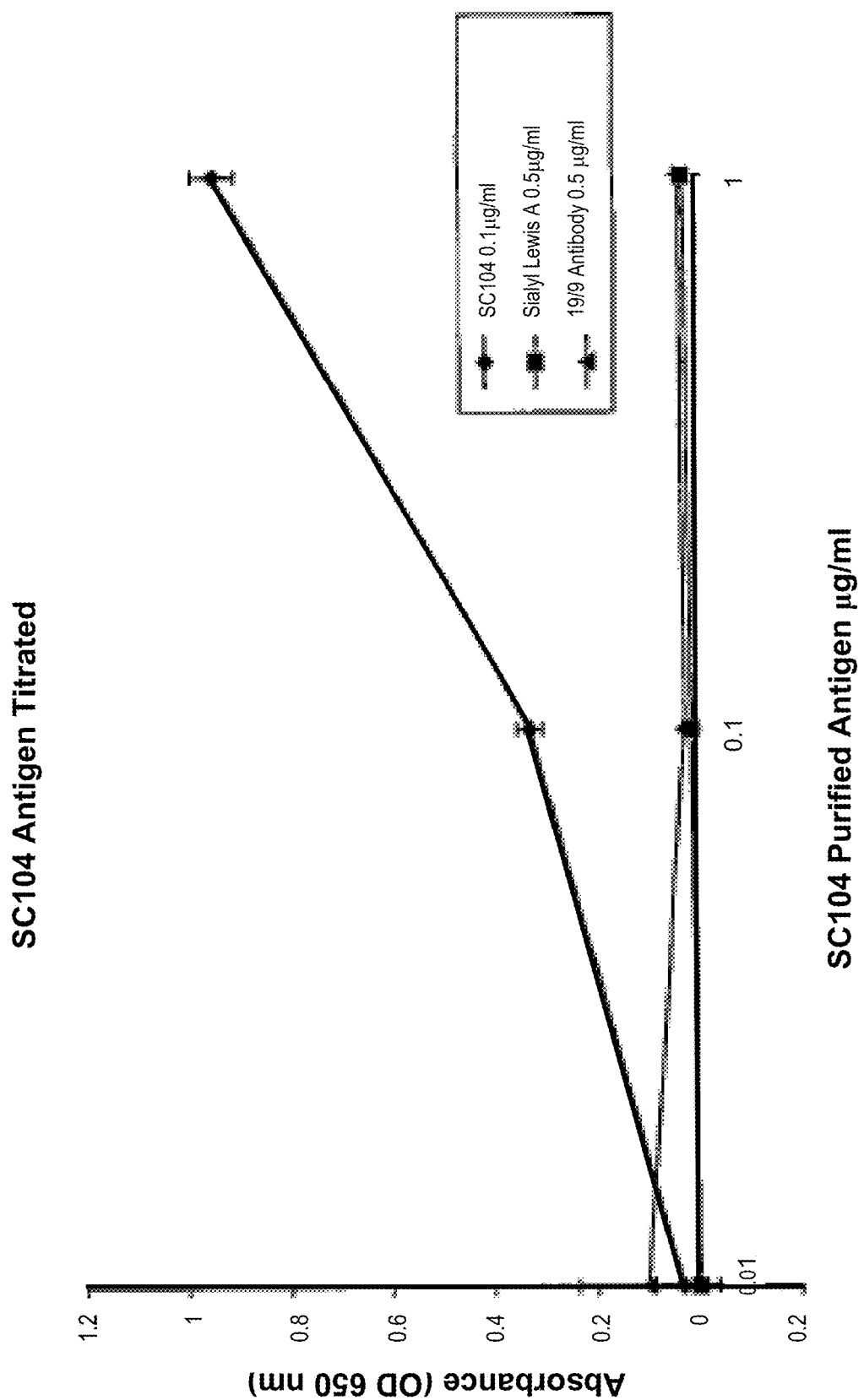

FIG. 13 is a graph demonstrating that whilst the SC104 antigen was seen to cross-react with SC104 it did not cross-react with an anti-sialyl Lewis $^a$ (a biomolecule previously evaluated for clinical potential) or 19/9 antibody.

Figure 14:
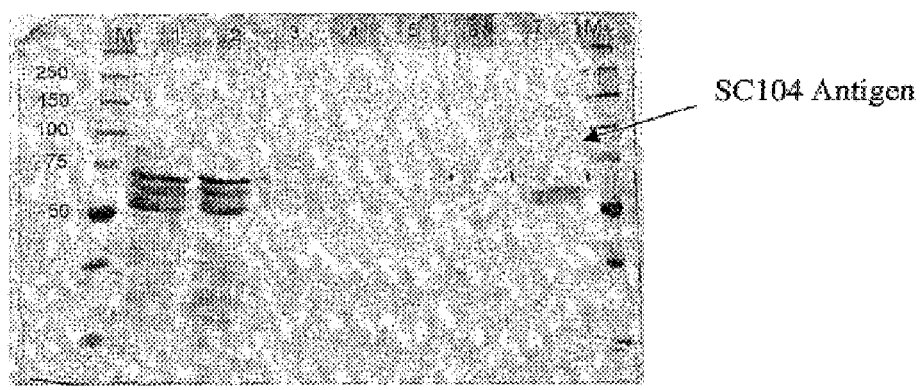

FIG. 14 demonstrates, using an SC104-Protein A sepharose column, a band for the SC104 immuno-purified antigen at between 50-75 KDa as identified on a Silver stained gel.

Figure 15:
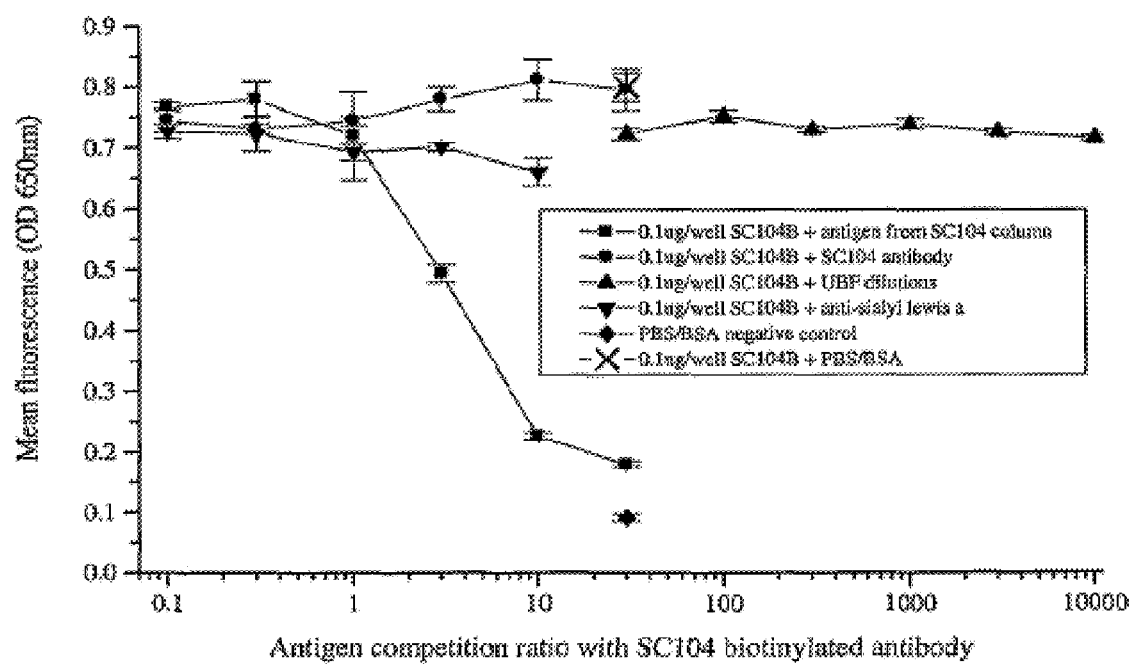

FIG. 15 shows the purified SC104 fraction from sputum competing with SC104 biotin for binding to C170 cells.

Figure 16:
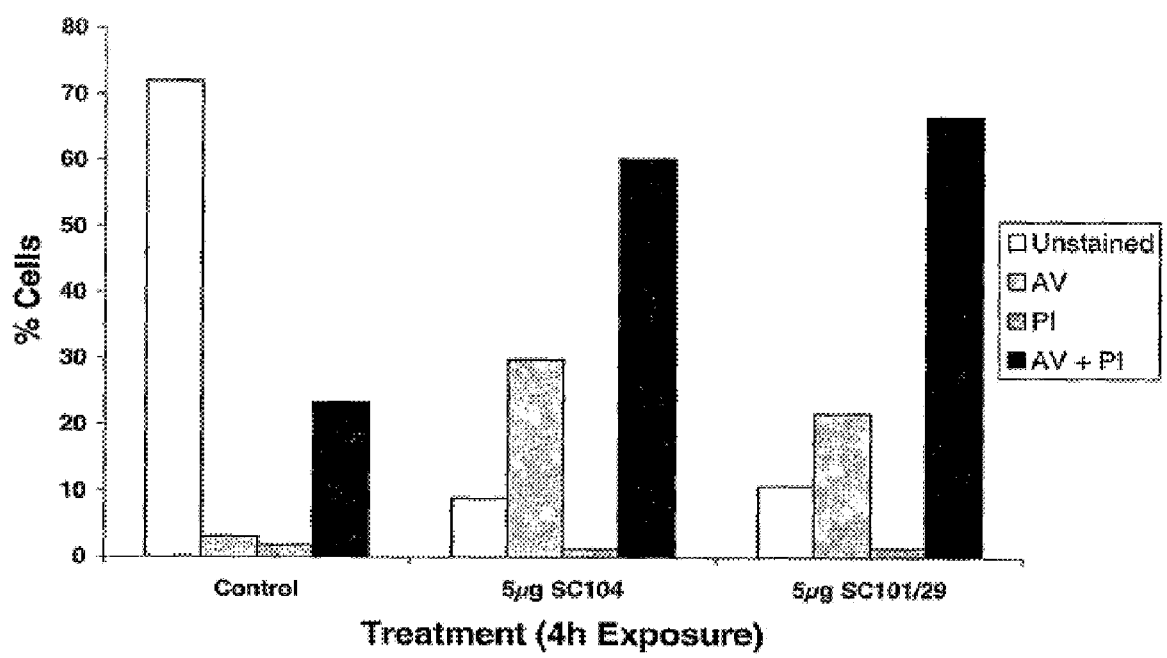

FIG. 16 is a histogram demonstrating the effect of SC104, or control 791T/36 antibody, on C170 tumour cells. Cells were stained with FITC labelled Annexin and propidium iodide and then analysed by dual colour flow cytometry. Results are expressed as the % of cells staining with annexin, PI or both. SC101/29 is included as a positive control.

Figure 17:
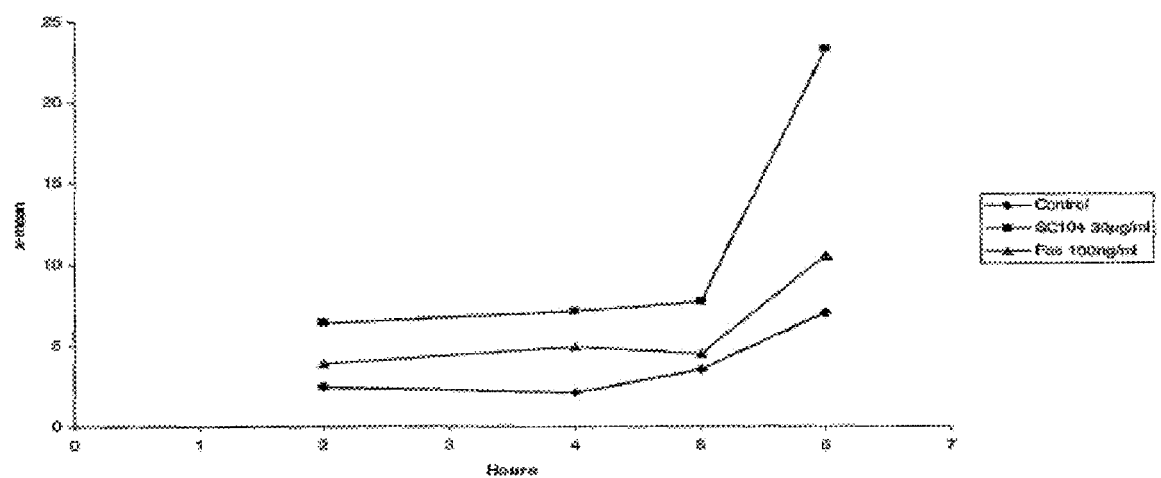

FIG. 17 is a graph to show FITC-z-FMK-vad activation of pan caspase after 6 hr exposure to adherent C170 cells. The results are expressed as X-mean.

Figure 18:
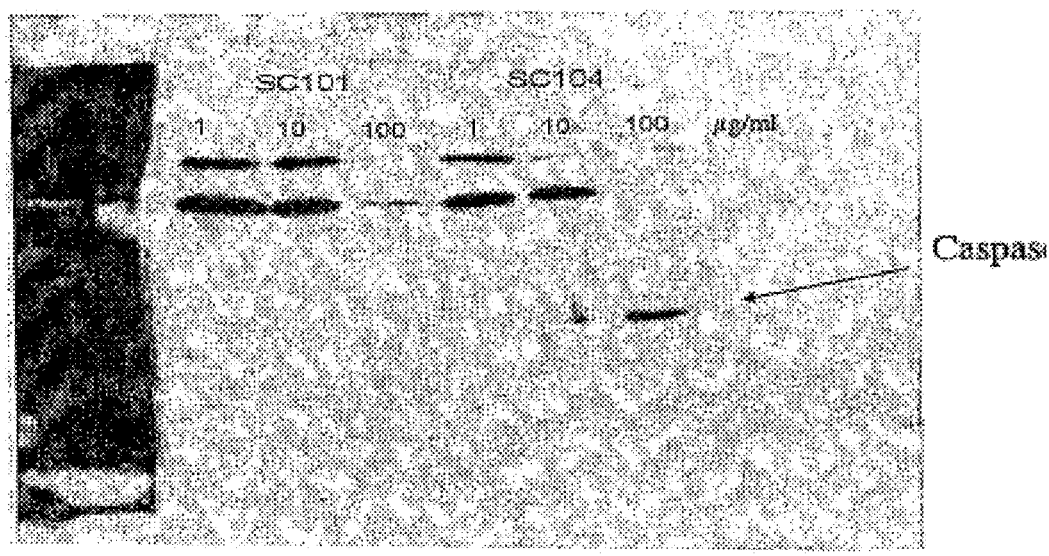

FIG. 18 demonstrates caspase 6 activation on adherent cells treated with the SC104 antibody. SC101 antibody treated cells are included as a negative control.

Figure 19:
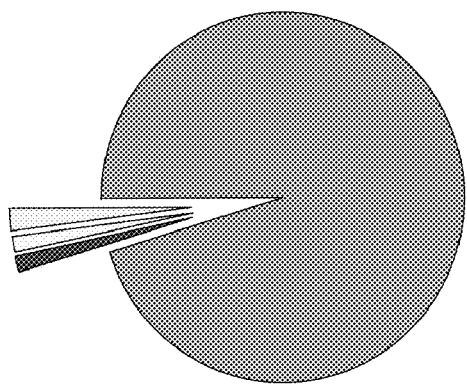
Figure 19:
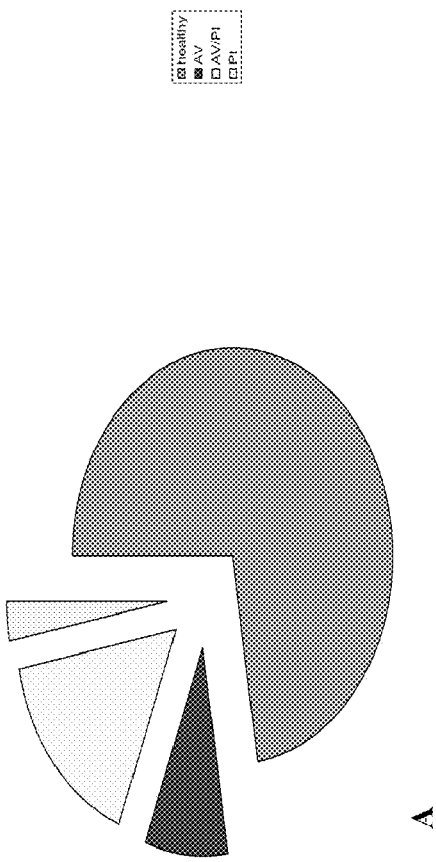

FIG. 19 demonstrates that if SC104 treated cells (A) are also exposed to 3 uM z-FMK-vad inhibitor (B) cell death can be significantly reduced as assayed using annexin V FITC and propidium iodide.

Figure 20:
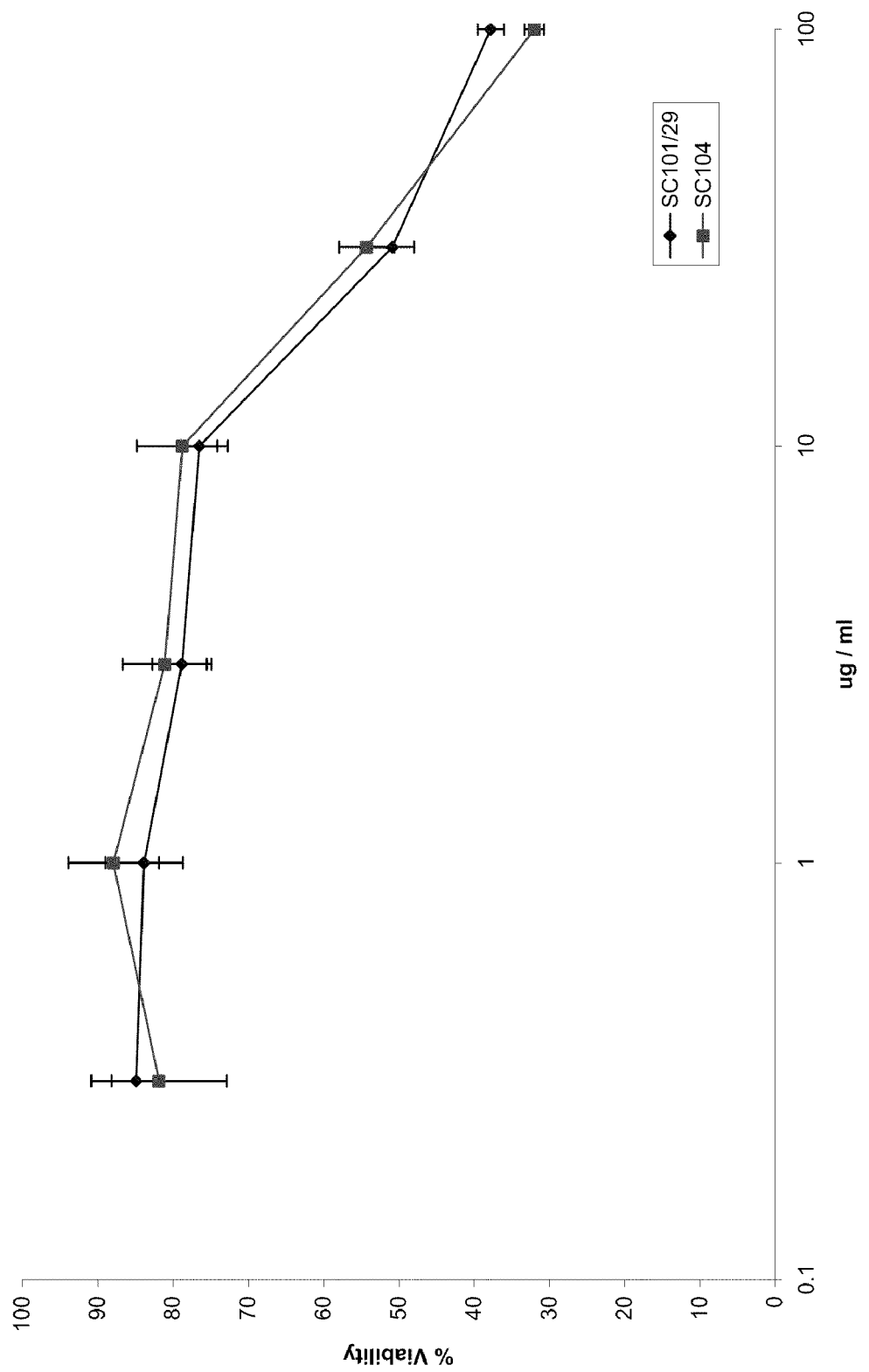
Figure 20:
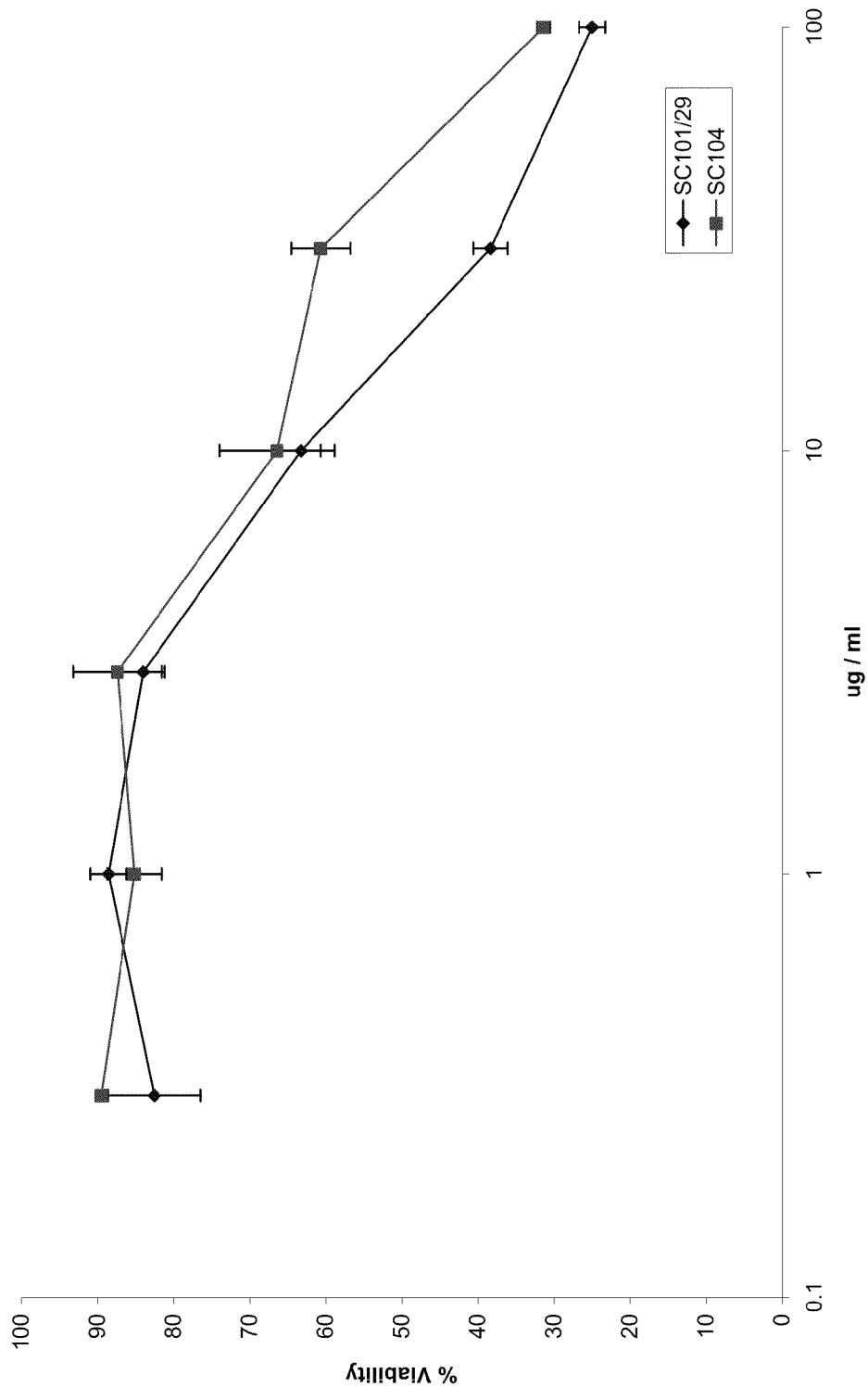
Figure 20:
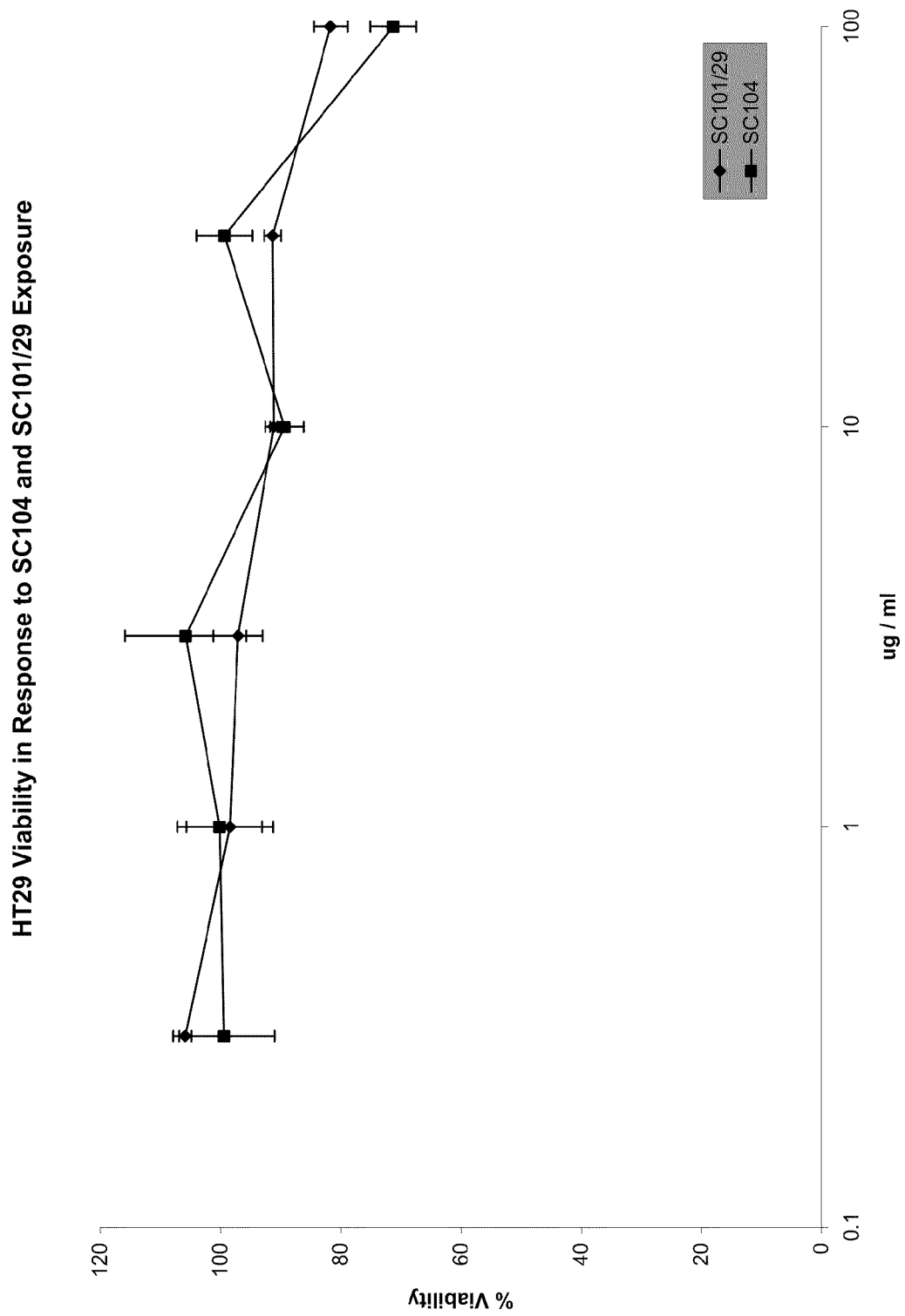
Figure 20:
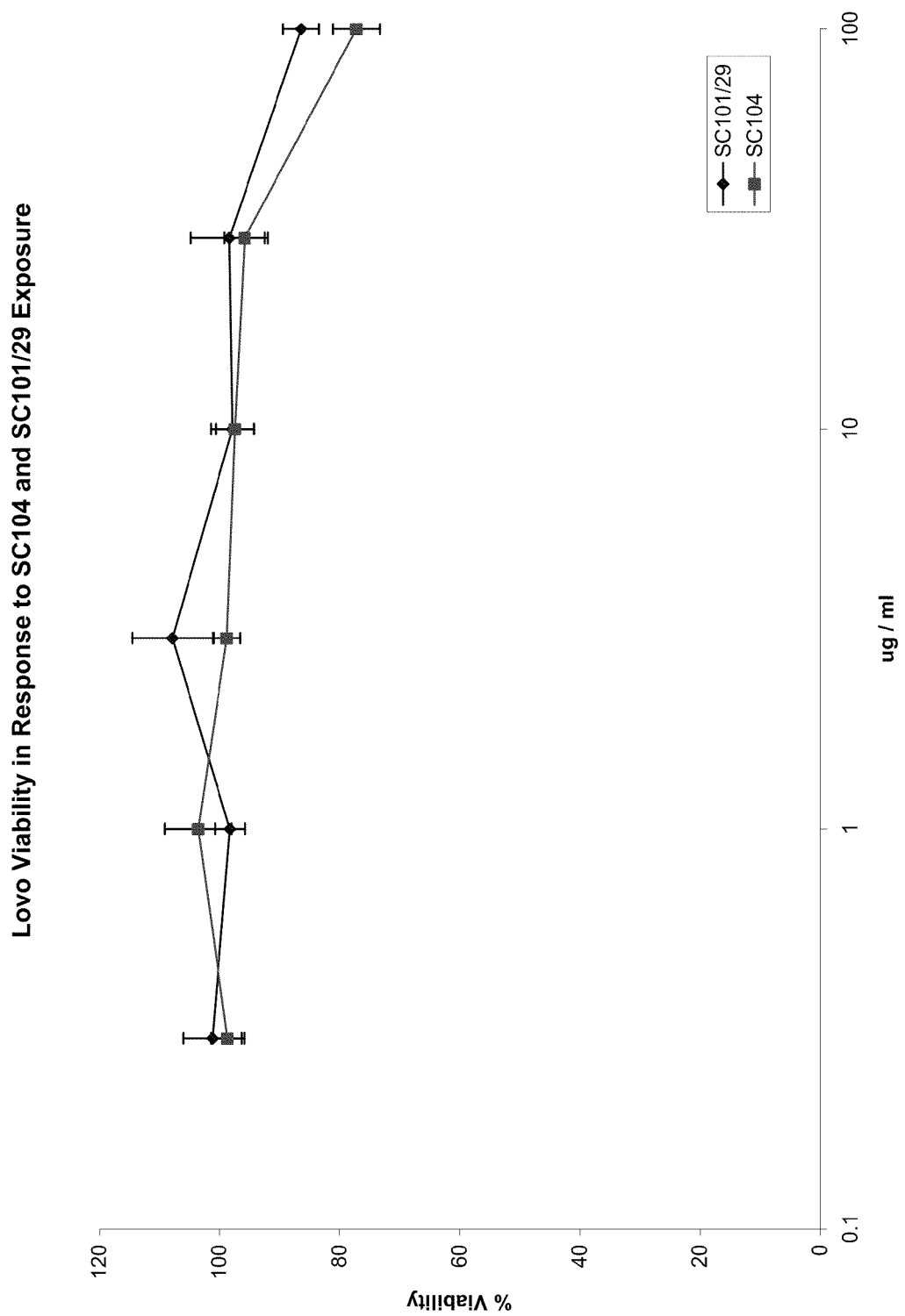

FIG. 20 shows graphs showing the % viability (number of cells exposed to the drug/number of cells exposed to control) if of a range of tumour cell lines (Colo205, C170, HT29 and LoVo). The number of viable cells was determined by MTS and optical density reading at 490 nm.

Figure 21:
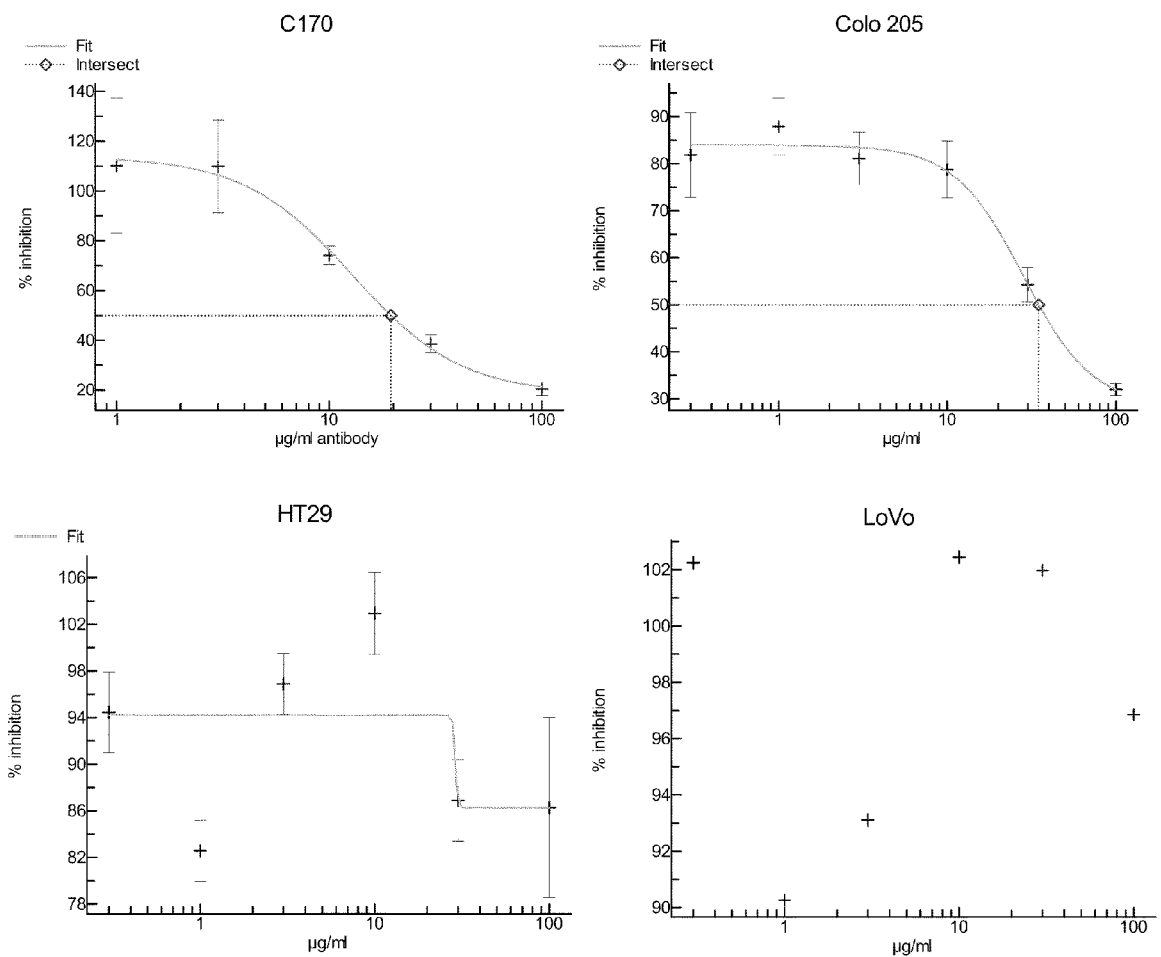

FIG. 21 demonstrates IC$_{50}$ fits for the tumour cell lines, C170, Colo205, HT-29 and LoVo extrapolated from typical cell viability results (% viability=number of cells exposed to the drug/number of cells exposed to control) as determined by MTS and optical density reading at 490 nm.

Figure 22:
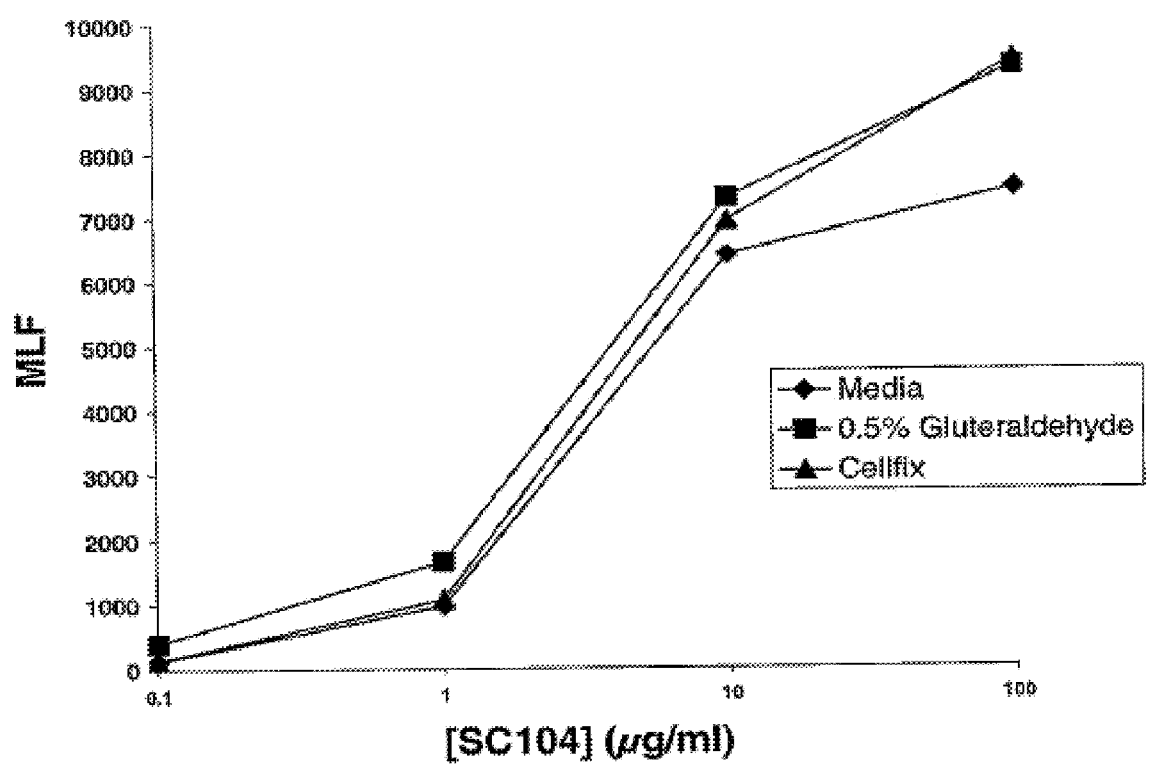

FIG. 22 is a graph to show that the fixation of tumour cells, either by Cellfix or glutaraldehyde does not significantly alter the binding of the antibody to the tumour cell line C170 as compared to those untreated in media alone. Cells were stained by indirect immunofluorescence, analysed by flow cytometry and the results expressed as mean linear fluorescent values.

Figure 23A:
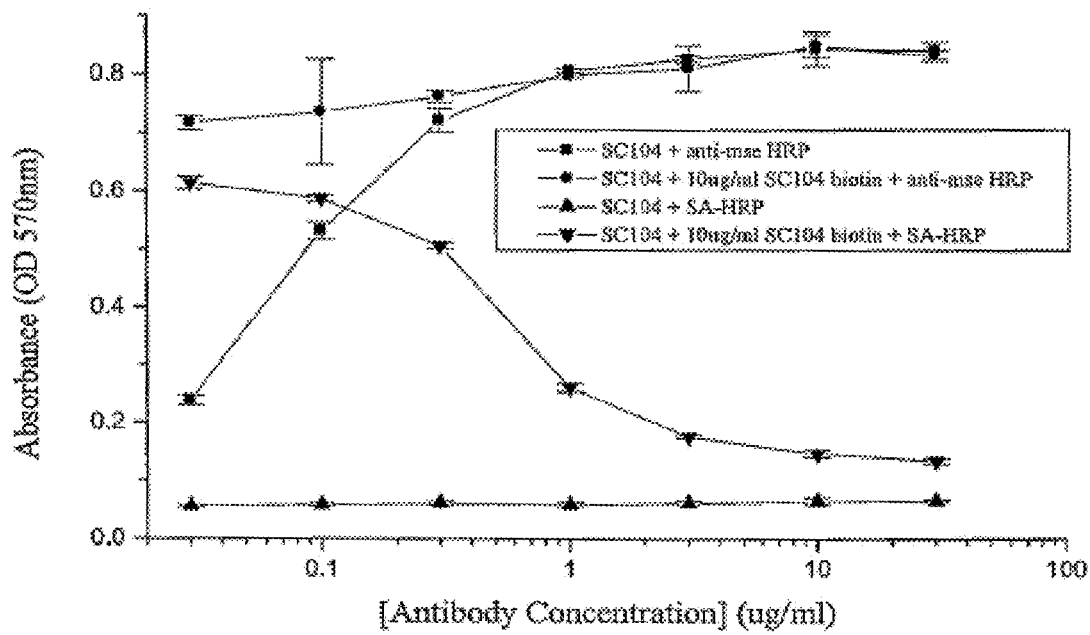
Figure 23B:
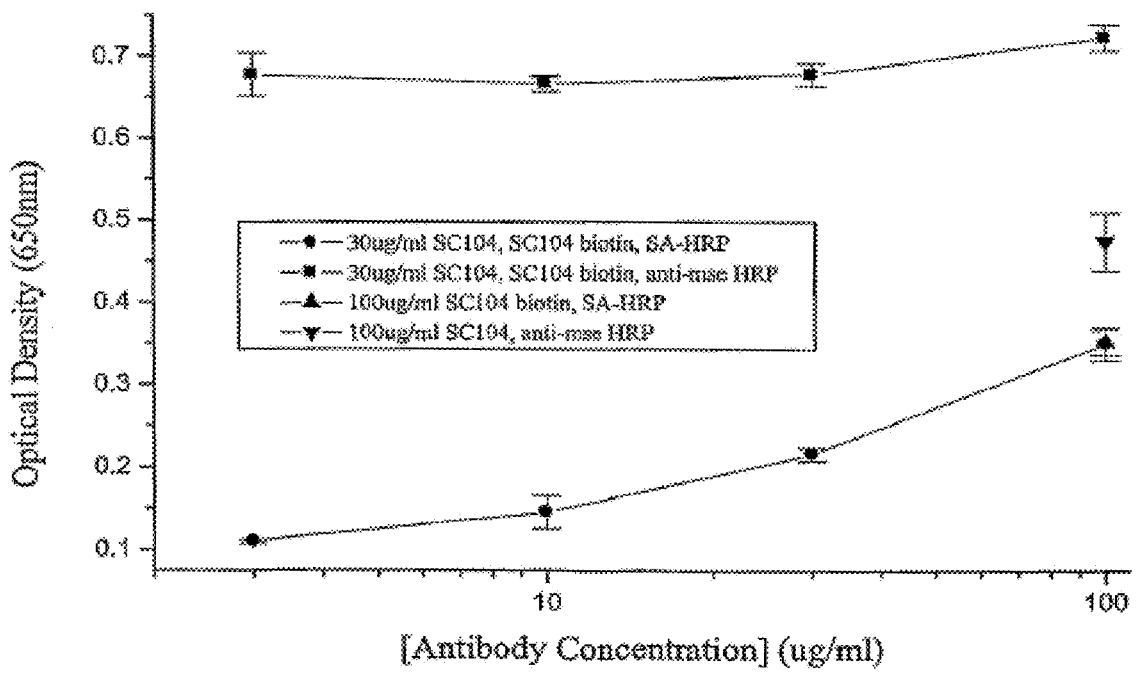

FIG. 23a shows that SC104 does not bind in a homophilic nature in the absence of antigen. Microtitre plates were coated with goat anti-mouse IgG Fc specific antibody prior to adding increasing concentrations of SC104 antibody. Bound SC104 antibody was detected by ELISA with goat anti-mouse horse radish peroxidase and TMB. To determine if SC104 could bind to itself SC104 biotin was added and its binding detected with SA-HRP/TMB. Controls included, SC104 which could not be detected with SA-HRP/TMB but both SC104 and SC104 biotin could be detected with goat anti-mouse HRP. Results are expressed as absorbance at 570 nm. FIG. 23b then shows that SC104 does bind in a homophilic fashion in the presence of C14 antigen. Plates were coated with C14 antigen and SC104 added to each well to the antigen. This was confirmed with goat anti-mouse HRP/TMB. SC104 biotin was then added at increasing concentrations and its binding was detected with SA-HRP/TMB. Results are expressed as absorbance at 650 nm.

Figure 24:
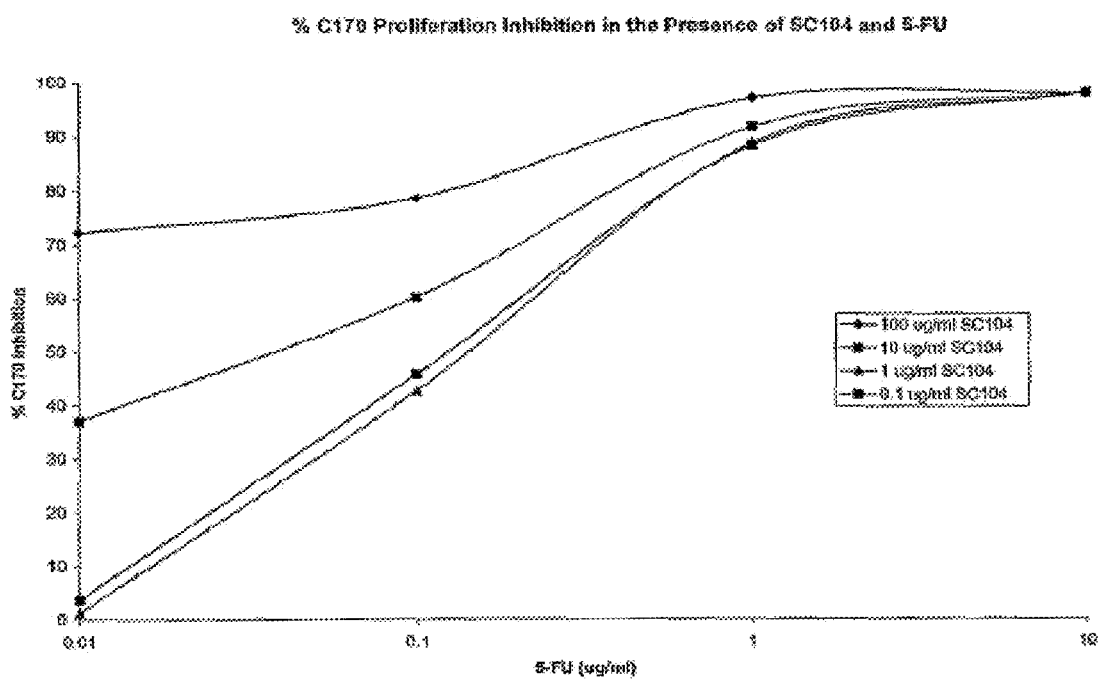

FIG. 24 is a graph demonstrating the effect of 5-Fluorouracil and SC104 antibody on cells. C170 cells were exposed to SC104 or control 791T/36 antibody (not shown) and 5-FU. The number of cells was determined by MTS and optical density reading at 490 nm.

Figure 25:
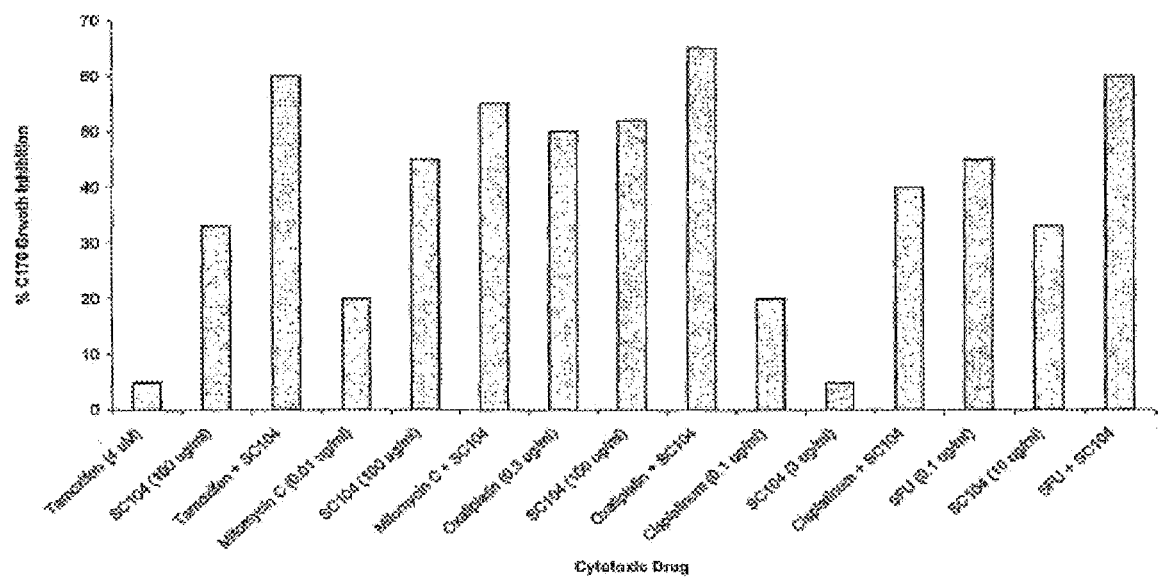

FIG. 25 is a graph demonstrating the effects of 5-FU, Cisplatin, Mitomycin C, Oxaliplatin and Tamoxifen on C170 cells either alone or in combination with SC104 antibody, or with SC104 antibody alone.

FIG. 26 shows graphs demonstrating the effect of SC104, 5-FU/leucovorin and a combination of SC104 and 5FU/leucovorin on the growth of C170 xenografts growing in nude mice. a) Growth of C170 xenografts was measured at days 7, 9, 12, 14 and 16 by measurement of cross-sectional area ($mm^2$) when animals were treated with either SC104 ip (0.2 mg), control antibody ip (0.2 mg) and 5-FU/leucovorin (12.5 mg/Kgiv) or SC104 ip (0.2 mg) and 5-FU/leucovorin (12.5 mg/Kg iv,) on days 1, 3, 5, 7, 21, 22. b) A survival plot demonstrating the effect of SC104, 5-FU/leucovorin or the combination of SC104 and 5-FU on the survival of nude mice expressing C170 xenografts. Animals were treated with either SC104 ip (0.2 mg), control antibody ip (0.2 mg) and 5-FU/leucovorin (12.5 mg/Kgiv) or SC104 ip (0.2 mg) and 5FU/leucovorin (12.5 mg/Kg iv,) on days 1, 3, 5, 7, 21, 22. c) Animals were weighed on days 7, 14, 21, 28 and 36 following treatment with SC104 ip (0.2 mg), control antibody ip (0.2 mg) and 5-FU/leucovorin (12.5 mg/Kgiv) or SC104 ip (0.2 mg) and 5-FU/leucovorin (12.5 mg/Kg iv,) on days 1, 3, 5, 7, 21, 22.

Figure 27:
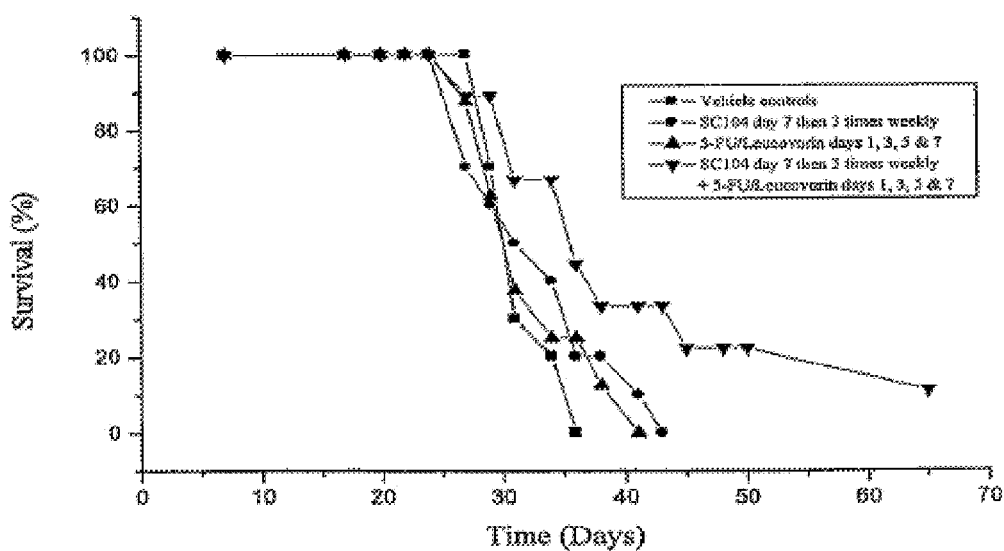

FIG. 27 is a graph demonstrating the effect of SC104, 5 FU/leucovorin and a combination of SC104 and 5FU/leucovorin on the growth of C170 xenografts growing in nude mice. Mice were treated with % FU/leucovorin 25 mg/Kg iv on days 1, 3, 5, 7, 21, 22 and with SC104 antibody (0.2 mg) three times per week staring on day 5. Growth of C170 xenografts was measured at days 7, 9, 12, 14 and 16 by measurement of cross-sectional area ($mm^2$) when animals were treated with either SC104 ip (0.2 mg), control antibody ip (0.2 mg) and 5FU/leucovorin or SC104 ip (0.2 mg) and 5FU/leucovorin. A graph demonstrating the effect of SC101, 5FU/leucovorin or the combination of SC101 and 5FU on the survival of nude mice expressing C170 xenografts.

EXAMPLES

Example 1

Production of SC104 Monoclonal Antibody

Methods

Immunisation: A range of isolated tumour cell lines were used in the immunisation protocol for the production of SC104 following the regime outlined in the Table 1. BALB/c female mice (6-12 weeks old, Bantin and Kingman, Hull) were immunised with 100 µl suspension of C146, C168, C170 and JW cells at 0, 4, 13 and 14 months BALB/c mice respectively. A cell density of $5\times10^6$ cells/ml was used for the first two immunisations, while the density was reduced to $5\times10^5$ cells/ml for the second two immunisations. The cells were suspended in Freund's complete adjuvant in the first instance with the second and subsequent immunisations using Freund's incomplete adjuvant. 5 days after the final immunisation the spleen cells were harvested and fused with PSNS1 cells.

TABLE 1

| Immunisation protocol | | | |
|---|---|---|---|
| Day | Cell Type | Cell Number | Route of administration |
| 0 | C170 | $5 \times 10^6$ | Ip |
| 42 | C146 | $5 \times 10^6$ | Ip |
| 56 | Colo205 | $5 \times 10^5$ | Ip |
| 96 | JW | $5 \times 10^5$ | Ip |

Hybridoma Production

The mouse was sacrificed by cervical dislocation and the spleen removed aseptically. The spleen was transferred to a petri dish containing serum free RPMI (20 ml, 37° C.) and the cells gently released into the medium. The tissue debris was allowed to settle from the cell suspension under gravity for two minutes. The individual splenocyte cells remaining in suspension were then recovered by centrifugation, resuspended in serum free RPMI and counted. The harvested P3NS1 cells were counted and resuspended. The two cell types were mixed in a ratio of 1:10 cells, P3NS1: splenocytes. The cell mixture was recovered as a pellet and loosened by gentle tapping. Warm polyethylene glycol 1500 was added (50% solution commercially available from Sigma chemicals) over 1 minute, followed by incubation at room temperature (1 min). Warm serum free media was then added over a further minute followed by the slow addition of a further 20 ml of serum free medium. The resuspended cells were recovered as a pellet and gently dispersed in warm RPMI1640 containing 15% foetal bovine serum and HAT selection agents. The cell suspension was aliquoted over 96-well plates previously coated with rat peritoneal exudate cells (PECS). The plates were then incubated at 37° C., 5% $CO_2$, 95% air until colonies of surviving hybridoma cells could be observed. The production of colon tumour specific antibody was screened for using C170 cells as the primary layer in a non-competitive sandwich ELISA. Cells from a number of positive wells were pooled and plated out across 96-well plates at cell densities of 5, 2.5, 1 and 0.5 cells/well (100 µl/well). The plates were incubated at 37° C., 5% $CO_2$, 95% air until the media in wells with colonies turned orange.

Screening Procedures

ELISA. Antibody responses in the serum of immunised mice were assayed by titration using a standard non-competitive ELISA procedure. 96-well tissue culture plates were coated with C170 cells at a cell density of $5\times10^5$ cells/ml (100 µl/well) in 10% foetal bovine serum in RPMI 1640. The plates were incubated overnight at 37° C., 5% $CO_2$, 95% air. The cells were then washed twice in phosphate buffered saline (pH7.3, PBS) prior to being fixed with 0.5% glutaraldehyde in PBS (10 min, 25° C., 100 µl/well). Remaining non-specific binding sites were blocked by incubation for 1 hr with 1% bovine serum albumin (fraction V from Sigma Chemicals Ltd.) in PBS. The cells were washed three times with a washing solution consisting of 0.05% Tween 20 in phosphate buffered saline before assaying post-boost serum for binding to C170 cells using a non-competitive sandwich ELISA. The pre-immunisation serum was used as a negative control.

Immunohistochemistry. Binding of hybridoma supernatants to tumour tissues was determined by indirect immunoperoxidase staining of frozen colorectal tumour sections. Tissue sections (5 µm) of cryopreserved tumour were treated with 0.3% $H_2O_2$ in 0.1% $NaN_3$ for 15 min to inhibit endogenous peroxidase. This was followed by incubation at room temperature with 10% human serum and 1% BSA prepared in PBS, for 30 min, and then the hybridoma supernatants were added at saturating levels which gave minimal non specific background staining for a further 30 min. The bound antibody was detected with rabbit anti-mouse Ig conjugated to peroxidase (Dako Ltd., Bucks., UK) and following extensive washing the slides were stained with 0.05% diaminobenzidine and 0.01% $H_2O_2$ in 0.05M Tris-HCl, pH7.6 and counterstained with haematoxylin.

Results

SC104 is a monoclonal antibody (mab) that was raised by immunisation of mice with 4 colorectal cancer cell lines. It was screened by immunohistochemistry against colorectal tumour sections and by ELISA against one of the immunising cell lines. It was cloned three times and was shown to be a mouse IgG1 mab. Table 2 shows that it binds to C170 cells with a higher intensity than a positive control antibody recognising Lewis$^{y/b}$ hapten. It also showed intense staining of colorectal tumours in comparison to either the Lewis$^{y/b}$ antibody or an anti-CEA antibody. It showed similar weak staining of normal colon tissues to an anti-CEA antibody.

TABLE 2

| | Screening of SC104 mab | | |
|---|---|---|---|
| | C170 ELISA | Immunohistochemistry[a] | |
| Antibody | (OD 405 nm) | Colorectal Tumour | Normal colon |
| SC104 | 0.301 | 3+ | + |
| Anti-Lewis$^{y/b}$ | 0.161 | 2+ | Mucin staining only |
| Anti-CEA | 0.001 | 2+ | + |
| No antibody | 0.001 | – | – |

[a] – negative, + minimal, 2+ strong, 3+ very strong

Example 2

Sequence of the SC104 Antibody

Methods

Amplification and sequencing of the heavy and light kappa chain variable regions of the mouse immunoglobulin SC104. Total RNA was isolated from the hybridoma SC104/1E9 after checking previously for antibody production by ELISA.

cDNA synthesised from 5 μg of the total RNA was used as a template for the amplification of the heavy and light chain variable domains of SC104. The following forward oligonucleotides that anneal to the leader sequence and reverse oligonucleotides to the CH1 domain of the constant region of each chain were utilised respectively in the PCR reactions with the high fidelity enzyme pfu turbo (Stratgene).

```
Forward Primers
                                         (SEQ ID NO: 1)
5'-ATG AGA GTG CTG ATT CTT TTG TG-3'
Heavy chain (SEQ ID NO: 2)
5'-ATG GAT TT(A/T) CA(A/G) GTG CAG ATT (A/T)TC AGC TTC-3'
Kappa chain Reverse Primers
                                         (SEQ ID NO: 3)
5'-CCC AAG CTT CCA GGG (A/G)CC A(A/G)(G/T) GGA TA(A/G) ACG G(A/G)T GG-3'
Heavy chain (SEQ ID NO: 4)
5'-CCC AAG CTT ACT GGA TGG TGG GAA GAT GGA-3'
Kappa chain
```

The amplified fragments were cloned into the TA vector pCR2.1 (Invitrogen). Clones containing insert were identified by restriction analysis and confirmed by DNA sequencing with the primers T7 and M13 reverse (Lark Technologies). Sequences were analysed and the following complimentary determining regions (CDR'S) identified for the heavy and light chain of the antibody SC104 (FIGS. 1a, b and c).

To verify that analysis of sequencing and translation was correct for both chains 10 μg of purified and concentrated SC104 antibody was denatured, separated on a 0.75 mm thick 8% SDS-PAGE gel by electrophoresis and transferred onto PVDF by semi dry electroblotting. After staining with Amido black the Kappa (25 KDa) and Heavy (50 KDa) chains were isolated and N terminally sequenced by Edman degradation (Alta Biosciences). Protein sequencing confirmed the analysed DNA and translated sequences for both chains.

Heavy Chain

```
Variable region (55bp-414bp)
CDR1 (130bp-162bp)
  G  Y  S  I  T  S  G  Y  S  W  H         (SEQ ID NO: 5)
GGCTACTCCATCACGAGTGGTTATAGTTGGCAC         (SEQ ID NO: 6)

According to Kabat numbering (145bp-162bp)
  S  G  Y  S  W  H                        (SEQ ID NO: 7)
AGTGGTTATAGTTGGCAC                        (SEQ ID NO: 8)

CDR2 (205bp-252bp)
  H  I  H  F  S  G  R  P  T  Y  N  P  S  L  S  S  (SEQ ID NO: 9)
CACATTCACTTCAGTGGTAGACCTACTTACAATCCATCTCTCAGCAGT  (SEQ ID NO: 10)

CDR3 (349bp-381bp)
  K  G  K  G  S  D  D  G  L  N  Y         (SEQ ID NO: 11)
AAGGGAAAAGGTTCCGACGATGGTTTGAACTAC         (SEQ ID NO: 12)

Signal leader sequence (1bp-54bp)
FR1 (55bp-129bp)
FR2 (163bp-204bp)
FR3 (253bp-348bp)
FR4 (382bp-414bp)
CH1 (415bp onwards)
```

Kappa Light Chain

```
Variable region (67bp-384bp)
CDR1 (136bp-165bp)
   S   A   S   S   S   L   S   Y   I   H      (SEQ ID NO: 13)
AGTGCCAGCTCAAGTTTAAGTTACATACAC                 (SEQ ID NO: 14)

CDR2 (211bp-231bp)
   D   T   S   N   L   A   S                  (SEQ ID NO: 15)
GACACATCCAACCTGGCTTCT                          (SEQ ID NO: 16)

CDR3 (328bp-354bp)
   F   Q   G   S   E   Y   P   L   T          (SEQ ID NO: 17)
TTTCAGGGGAGTGAGTATCCACTCACG                    (SEQ ID NO: 18)

Signal Leader sequence (1bp-66bp)
FR1 (67bp-135bp)
FR2 (166bp-210bp)
FR3 (232bp-327bp)
FR4 (355bp-384bp)
CH1 (385bp onwards)
```

Example 3

Expression of Chimeric SC104 Monoclonal Antibody

To verify expression of functional antibody from the DNA sequences the Afe1 and BsiW1 restriction sites were incorporated into the heavy and light chain variable regions at the end of framework 4 within pCR2.1 by site directed mutagenesis using the designed complimentary oligonucleotides.
Heavy Chain Variable Afe1

```
Forward Primer
                                               (SEQ ID NO: 19)
5'-C TCA GTC ACC GTC TCT AGC GCT AAA ACG ACA CCC

CCA CC-3'

Reverse Primer
                                               (SEQ ID NO: 20)
5'-GG TGG GGG TGT CGT TTT AGC GCT AGA GAC GGT GAC

TGA G-3'
```

Light Chain Variable BsiW1

```
Forward Primer
                                               (SEQ ID NO: 21)
5'-CC AAG CTG GAA ATG ACA CGT ACG GAT GCT GCA

CCA ACT G-3'

Reverse Primer
                                               (SEQ ID NO: 22)
5'-C AGT TGG TGC AGC ATC CGT ACG TGT CAT TTC CAG

CTT GG-3'
```

The murine heavy and light chain variable regions of SC104 were excised from pCR2.1 and cloned into the HindIII/Afe1 and BamHI/BsiW1 sites of the mammalian expression vector pDCORIG IB fused inframe with the human Fc constant region of each chain respectively. This plasmid was identified by restriction analysis and confirmed by DNA sequencing.

CHO-S was stably transfected with 15 µg of the above plasmid and genejuice (Novagen) according to the manufacturer's recommendations. Transfectants were selected in medium containing Zeocin (300 µg/ml) for 14 days. Expression of functional chimeric SC104 antibody secreted from the transfectants was confirmed by binding to the cell surface of the cell line C170 and flow cytometry (FIG. 1d).

In brief after washing in RPMI/10% FCS C170 cells were incubated for 30 minutes at 4° C. with either spent medium containing the chimeric antibody or medium alone. Cells were washed and incubated for a further 30 minutes at 4° C. with a FITC conjugated rabbit anti-human IgG antibody specific for the CH2 domain (DAKO, F0123). Cells were washed again, resuspended and analysed by flow cytometry.

Example 4

Binding Studies Using SC104 Monoclonal Antibody

Experiment 1

Methods
Immunohistochemistry staining of normal and tumour tissues. Human tissues were obtained from an Inveresk approved supplier. Each tissue used was snap frozen in liquid nitrogen and stored at approximately −70° C. (±10° C.). Cryostat sections were cut and placed onto super frost plus slides. All tissue samples were treated with an antigen marker appropriate for each tissue in order to confirm the preservation of antigens in that tissue. The markers used were keratin for epithelial bearing tissues, CD45 for all lymphoid tissues, and desmin for all cardiac and skeletal muscle. Each tissue was examined from three unrelated donors. The method of staining employed was an indirect, 2 or 3-stage method, using secondary and tertiary antibodies together with an avidin-biotin-peroxidase complex. Endogenous peroxidase activity was blocked using hydrogen peroxide. Endogenous biotin was blocked by treating all tissue sections with a sequence of avidin-biotin. When a tertiary antibody was used, all tissue sections were treated with normal swine serum, which inhibits the binding of tertiary antibodies to the tissues. Validation of the immunohistochemical staining method was determined by staining on positive control tissues, the absence on negative controls and the effect of fixation on staining of control tissues. SC104 was tested against 6 donors of colon tumour and one of heart at concentrations of 0 or 50 µg/ml. Tissues were fixed in either acetone or neutral buffered formalin. Two samples of colon tumour stained well enough for use as a positive control and there was no staining in heart. Neutral buffered formalin was found to be the optimum fixative. The lowest concentration of SC104 giving the maximum staining intensity was 1 µg/ml and this concentration was used for subsequent work.

Results
SC104 was screened for binding to a range of frozen tumour and normal tissue sections (Table 3). There was positive staining of the neoplastic epithelium of the colon, endometrial, oesophageal, parotid salivary gland and stomach and less intense staining of small numbers of epithelial cells in three of the six breast tumours. Positive staining was recorded in the epithelium of normal large intestine, parotid salivary gland, tonsil and uterine cervix. Less intense staining was recorded in small numbers of transitional epithelial cells in the urinary bladder, scattered thymic lymphocytes of a single donor, glandular epithelial cells of the skin, epithelial cells of the prostate, breast and fallopian tube, ovarian follicular cells, alveolar lining cells of the lung and small numbers of glial cells from the brain of one donor. Mucus stained positively in the stomach and small intestine. No specific staining was recorded in normal human heart, kidney, placenta or spleen. These results suggest that the antigen can be expressed by a range of epithelial cells but that it is predominantly localised within the gastrointestinal tract. The immunohistochemistry suggested that the antigen was expressed more strongly on colorectal tumours than adjacent normal tissues.

TABLE 3

Immunoreactivity of SC104 antibody with frozen tumour and normal tissue sections

| Tissue | Anti-EGF Mab | SC104 binding | Comments on staining |
|---|---|---|---|
| Tumours | | | |
| Lung | 6/6 | 0 | |
| Oesophageal | 4/4 | 4/4 | |
| Breast | 0 | 3/6 | |
| Renal | ND | 0 | |
| Colon | 3/8 | 8/8 | |
| Ovary | 0 | 0 | |
| Parotid | 0 | 2/2 | |
| Prostate | 0 | 0 | |
| Stomach | 0 | 4/4 | |
| Testes | ND | 0/1 | |
| Endometrial | 1/2 | 2/2 | |
| Normal Tissues | | | |
| Brain | 0 | 1/2 | Small number of scattered glial cells from the brain of one donor |
| Breast | 3/3 | 2/3 | Epithelial cells scattered moderate |
| Fallopian tube | 0 | 2/3 | Epithelial cells scattered moderate |
| Heart | 0 | 0 | |
| Kidney | 0 | 0 | |
| Large intestine | 3/3 | 3/3 | Epithelial cells, mucous, diffuse mild to moderate |
| Lung | 0 | 2/3 | Alveolar lining cells one donor minimal and one donor mild |
| Ovary | 0 | 3/3 | Follicular cells scattered and mild |
| Placenta | 3/3 | 0 | |
| Prostate | 3/3 | 3/3 | Epithelial cells scatted and moderate |
| Parotid salivary gland | 3/3 | 3/3 | Moderate |
| Skin | 3/3 | 2/3 | Diffuse minimal staining |
| Small intestine | 0 | 3/3 | Mucus superficial, diffuse minimal |
| Spleen | 0 | 0 | |
| Stomach | 0 | 2/3 | Mucus superficial, diffuse mild |
| Thymus | 0 | 3/3 | Epithelial cells, Hassall's corpuscle, membrane scattered mild |
| Tonsil | 0 | 3/3 | Keratinised epithelium, membrane, scattered mild to moderate. |
| Urinary Bladder | 2/3 | 2/2 | Epithelial cells transitional epithelium, membrane scattered mild |
| Uterine cervix | 3/3 | 3/3 | Epithelial cells, membrane, diffuse mild to moderate |

Notes:
ND not done.

Experiment 2

Methods
Binding to Tumour Cell Lines by Indirect Immunofluorescence and Flow Cytometric Analysis.

C170, Colo205, MKN45, R1D9, and 791T cells ($10^5$) were resuspended in 50 µl of SC104 mab (0-20 µg/ml) and incubated on ice for 20 min. After washing the samples 3 times in RPMI/10% FCS cells were incubated with FITC labelled rabbit anti-mouse (1/50: Dako Ltd, Bucks, UK) antibody and incubated on ice for 30 minutes prior to analysis on a FACScan (Becton Dickinson, Sunnyvale, Calif.). Results are expressed as mean linear fluorescence (MLF).
Binding to tumour cells by ELISA. 96-well tissue culture plates were coated with cells at a cell density of $5 \times 10^5$ cells/ml (100 µl/well) in 10% foetal bovine serum in RPMI 1640. The plates were incubated overnight at 37° C., 5% $CO_2$, 95% air. The cells were then washed twice in phosphate buffered saline (pH7.3, PBS) prior to being fixed with 0.5% glutaraldehyde in PBS (10 min, 25° C., 100 µl/well). Remaining non-specific binding sites were blocked by incubation for 1 hr with 1% bovine serum albumin (fraction V from Sigma Chemicals Ltd.) in PBS. The cells were washed three times with a washing solution consisting of 0.05% Tween 20 in phosphate buffered saline. Cells were incubated with SC104 (1 µg/ml) for 1 hr at room temperature and then bound antibody detected with goat anti-mouse horse radish peroxidase and ABTS. Results are expressed as absorbance at 405 nm.

Results
Further characterisation of the antigen expression was performed by ELISA on a range of tumour cell lines (FIG. 2a). SC104 antibody predominantly bound to cell lines of the gastrointestinal origin. SC104 bound to C170, Colo205 and R1D9 cells with a MLF of 1500 to 4,000.

Experiment 3

Methods
Primary tumour binding. Tumour specimens were obtained at the time of colorectal cancer resection. Specimens were finely minced and disaggregated with 0.05% collagenase (Type IV, Boehringer Mannheim, Lewes, UK) for 20 min at 37° C. The tumour cell suspension was removed and washed 3 times in Hanks balanced salt solution (Gibco BRL, Paisley, UK). Fresh collagenase was added to the remaining tissue and it was reincubated for a further 20 min. This procedure was repeated twice before combining cells from all dissociations and resuspending them in Dulbecco's medium containing 20% fetal calf serum (Gibco). Cells were incubated for 1 hr at 4° C. with SC104 mab (1 µg). Cells were washed twice and incubated for a further hr with FITC-conjugated rabbit anti-mouse immunoglobulin (Dako Ltd., Bucks., UK). Normal mouse immunoglobulin was used as a negative control and this fluorescence was subtracted from the fluorescence obtained with SC104. The cells were washed 3 times prior to analysis on a FACScan (Becton Dickinson, Sunnyvale, Calif.). Results are expressed as mean linear fluorescence (MLF). Disaggregation of solid tumours yields a mixed population of cells including red blood cells, lymphocytes, stromal cells, macrophages and endothelial cells. The percentage of epithelial cells is measured by staining of cytokeratin mab Cam 5.2. was only 22±13% (range 10-60). However, following forward angle light scatter gating to selectively analyse cells in the malignant cell size range 79±4% (range 69-86) of the cells analysed were epithelial. Furthermore, the variation between tumours was considerably reduced. The percentage of leukocytes as measured by staining with the anti-CD45 mab F-10-89 in the total nucleate population was 74±16 (range 40-90). This was considerably reduced to 5.5±5% (range 1-20) following FACS IV gating for malignant size. The percentage of stromal cells in the population of cells analysed in the malignant size range was 3.5±3% (range 1-13).

Results
SC104 was also shown to bind strongly to >80% of freshly disaggregated colorectal tumour cells with a mean antigen density of $4 \times 10^5$ antigens per cell (range $1.5$-$10 \times 10^6$ antigen per cell; FIG. 3).

Experiment 4

Method

Tumour and normal membrane extract binding. Extranuclear extractions of colorectal and normal colonic membranes were produced and binding of SC104 was assayed by ELISA.

Results

To further quantify the differential staining obtained by immunohistochemistry, extranuclear membrane preparations of primary colorectal tumours and normal colon from the resection margin were produced. ELISA staining of these membranes with SC104 revealed weak staining of the normal colon whereas moderate to strong staining of the tumour membranes were observed with the mean T:N ratio being 6:1 (Table 4).

TABLE 4

Relative binding of SC104 to tumour and normal membrane extracts

Binding of SC104 mab to extranuclear membranes

| Patient | Colorectal Tumour | Normal colon | T:N ratio |
|---|---|---|---|
| 1 | 0.001 | 0.001 | — |
| 2 | 0.437 | 0.068 | 6.6:1 |
| 3 | 0.221 | 0.217 | 1:1 |
| 4 | 0.278 | 0.042 | 7:1 |
| 5 | 0.196 | 0.066 | 3:1 |
| 6 | 0.281 | 0.035 | 8:1 |
| 7 | 0.102 | 0.139 | 1:1 |

Experiment 5

Methods

Binding to purified antigen preparations. The C14 antigen (90 KDa glycoprotein purified from saliva by affinity chromatography on C14 monoclonal), CEA (180 KDa glycoprotein purified from colorectal tumour live metastases by affinity chromatography with 365 mab) and glycolipid extract (glycolipid extracted in 3:1 methanol chloroform w/v from colorectal tumours) were dried onto microtitre plates by overnight incubation at 37° C. Binding of SC104 mab was assayed by ELISA as described above.

The Lewis$^{y}$ hapten and the type I and type II H blood group antigen (Sigma, Poole, Dorset) were dried microtitre plates by overnight incubation at 37° C. Binding of SC104 mab was assayed by ELISA as described above.

Results

To try and identify the nature of the antigen recognised by SC104 antibody, it was used to stain three different antigen preparations (FIG. 4). The first was CEA as this is a well known and immunogenic antigen expressed by colorectal tumours. No significant staining of CEA was observed although the anti-CEA antibody showed good reactivity confirming the presence of functional antigen. The second preparation was a Lewis$^{y/b}$ expressing glycoprotein extracted from saliva. This antigen is a 90 KDa glycoprotein that carries a wide range of carbohydrate residues. Both the anti-Lewis$^{y/b}$ antibody and SC104 antibody bound to this glycoprotein whereas the anti-CEA antibody failed to bind. A similar result was obtained when a methanol/chloroform tumour glycolipid extract was assayed. These results suggested that SC104 was recognising a carbohydrate residue expressed on both glycoproteins and glycolipids and that it may be recognising Lewis$^{y/b}$. To verify if SC104 was not binding to a blood group antigen it was screened for binding to Lewis$^{y}$, H type I and type II blood group haptens by ELISA (Table 5). The anti-H antibody bound strongly to all three haptens and the Lewis$^{y/b}$ antibody to the Lewis$^{y}$ hapten but SC104 failed to react with any of these haptens.

TABLE 5

SC104 binding to blood group antigens

| Antibody | Binding of antibodies to blood group antigens as measured by ELISA (OD 405 nm) | | |
|---|---|---|---|
| | Lewis$^{y}$ | H blood group Type I | H blood group Type II |
| SC104 | 0.057 | 0.087 | 0.076 |
| Anti-H | 2.058 | 2.174 | 1.331 |
| Anti-Lewis$^{y/b}$ | 0.662 | 0.129 | .097 |

Example 5

Identification of Tumour Glycolipid Recognised by SC104 Monoclonal Antibody Experiment 1

Optimisation of Lipid Extraction and Immunostaining Protocols

Methods

Lipid extraction from C170 tumour cells. A pellet of C170 cells (1 ml packed cell volume) was obtained by trypsinisation of a static adherent tissue culture. The pellet was washed in PBS and the excess buffer removed by aspiration following centrifugation, then stored at −80° C. The pellet was extracted with chloroform:methanol (3:1, v/v, 19 ml). The resultant emulsion was centrifuged at 8,000 rpm in a 50 ml solvent resistant (Tefzel) centrifuge tube for 15 min at 4° C. The supernatant was dried down using a rotary evaporator at 30° C. and resuspended in a small volume (~1 ml) chloroform:methanol:0.5% $CaCl_2$(aq) (50:40:10).

HPTLC analysis of lipid extracts The sample was multiply spotted onto a Merck HPTLC plate and developed in chloroform:methanol:0.5% $CaCl_2$(aq) (50:40:10) as standard. The plates were dried and then placed in an iodine vapour tank. Bands were marked in pencil and the iodine allowed to evaporate off the plate over night. The plates were then immunostained in order to localise the antigen.

Immunostaining of developed HPTLC plates. For SC104 immunostaining, the plates were immersed in polyisobutyl methylmethacrylate (0.1% w/v solution) hexane:chloroform (9:1) for 15 seconds then allowed to dry. The plates were then blocked in 3% BSA in PBS for 1 hr at room temperature, followed by incubation in either test antibody solution (10 μg/ml) or BSA solution, for 1 hr at room temperature. The plates were then washed three times in PBS/Tween-20 (0.1%), before being incubated in rabbit anti-mouse HRP conjugate from Dako (1/250 in PBS) for 1 hr at room temperature. The plates were then washed three times in PBS/Tween −20(0.1%) and once in 10 mM Tris, 100 mM NaCl pH 7.0, 0.1% Tween and developed in Sigma-FAST BCIP/NBT reagent.

Chemical staining of developed HPTLC plates. Orcinol staining was employed to detect the presence of carbohydrate moieties. Developed HPTLC plates were allowed to dry before spraying with orcinol reagent until fully coated. The plates were dried in a stream of hot air and incubated at 100° C. for 15 minutes. Ninhydrin staining was used to detect molecules containing free amino groups. Developed HPTLC plate were first allowed to dry and then dipped in ninhydrin solution (0.25% ninhydrin w/v in acetone) until fully wetted. The plate was then allowed to develop at room temperature for several hours.

Results

The antigen was found to be successfully extracted in 3:1 chloroform:methanol mix, with no change in the number of bands detected compared to the original 2:1 solvent extraction. However, increasing the solvent to 4:1 chloroform: methanol appeared to reduce the number of bands detected by HPTLC and consequently was not employed for extraction purposes. Early immunostaining experiments also employed a 60 second incubation of the HPTLC plate in 0.1% w/v polyisobutyl methacrylate in hexane; however, it was found that it was necessary to reduce this to 15 seconds to give reproducible detection of the antigen. Finally it was found necessary to incorporate a phosphate free wash of the HPTLC plates prior to incubation with the phosphatase substrate to ensure maximum sensitivity.

SDS-PAGE and Western blotting experiments have previously shown that SC104 antigen could be detected in the whole cell extract, cell lysate and the insoluble pellet produced during the preparation of cell membrane. The antigen was however not detected in the cell membrane preparation itself. In addition, HPTLC separation and immunostaining of the insoluble pellet produced in the membrane preparation was also able to detect the antigen. This suggests that the antigen is lipid or a very hydrophobic protein.

Experiment 2

Analysis of Antigen Containing Fraction by Silica Column Chromatography

Methods

Silica column fractionation of lipid extract. A gravity column (150 mm i.d.) was packed with a silica slurry in chloroform:methanol:0.5% $CaCl_2$(aq) (50:40:10). The C170 extract, re-dissolved in ~1 ml chloroform:methanol:0.5% $CaCl_2$(aq) (50:40:10) was loaded onto the column and eluted using the same solvent conditions. Fractions were collected and analysed by HPTLC. SC104 immunostaining was employed to locate the antigen and chemical staining methods were used to further characterise the fraction.

Ceramide glycanase digestion of antigen. Ceramide glycanase digestion was used to release oligosaccharides from glycolipid molecules. Antigen solution in 50 mM sodium acetate, pH 5.0, 0.1% w/v sodium cholate was mixed with ceramide glycanase solution (1 μl for 50 μl antigen) and incubated at 37° C. for 3 hrs. The de-glycosylated lipid was separated from the released oligosaccharides by mixing with 250 μl chloroform:methanol (2:1) followed by brief centrifugation. The upper aqueous phase was separated from the lower organic phase and the two dried down separately.

Results

Small scale fractionation of C170 lipid extract (obtained from ~0.5 ml packed cell volume) was demonstrated on a ~10 ml bed volume silica column using 50:40:10 chloroform: methanol:$CaCl_2$ (0.5% w/v in aqueous solution) as the mobile phase. However, in order to allow antigen characterisation it was necessary to scale this method up. This was shown to be possible using ~10 ml packed cell volume to obtain the lipid extract and increasing the column volume to ~36 ml.

Whole lipid extract was loaded onto the scaled up column, fractions collected and the antigen-containing fraction detected by immunostaining (FIG. 5). An antigen with $R_F$ of 0.53 was detected. HPTLC and chemical staining was then used to further characterise this fraction. Orcinol staining of the HPTLC plate was used to detect the carbohydrate moiety of glycolipids. This revealed three bands with $R_F$ values between 0.50 and 0.61 and seemed to correspond to the initial $R_F$ value of the antigen. However, immunostaining repeated concurrently with orcinol staining revealed an unusual shift in the $R_F$ of the antigen, with 3 bands detected between $R_F$ 0.36 and 0.39 (FIG. 6). This may suggest that the bands detected by orcinol staining do not correspond to the antigen but represent glycolipid contaminants.

In order to ascertain if this antigen was a protein, the fraction was analysed by SDS-PAGE and Western blotting. Silver staining of the gel did reveal very low levels of protein contamination; however Western blotting failed to specifically detect any antigen in the preparation suggesting that the antigen itself is not a protein.

An aliquot of the antigen-containing fraction was digested with ceramide glycanase to remove the carbohydrates. The glycans were separated from the lipid portion using 2:1 chloroform:methanol; with the free glycans predicted to partition with the methanol and the de-glycosylated lipids partitioning with the chloroform. Immunostaining and chemical staining techniques were then performed on HPTLC plates of intact glycolipid and de-glycosylated lipid. Immunostaining revealed the presence of antigen ($R_F$ 0.38-0.46) with the intact glycolipid and not the de-glycosylated lipid (FIG. 7). However, later experiments demonstrated that the partitioning of undigested antigen is highly variable, with the antigen sometimes being detected in either the aqueous, organic or both phases. Thus, the failure to detect antigen in a ceramide glycanase treated organic fraction is inconclusive. It may be due to partitioning of the antigen into the aqueous phase, rather than ceramide glycanase removal of the antigen.

In order to confirm the above experiment it was repeated with both the organic and the aqueous phase being analysed following digestion. Analysis of the samples by HPTLC and iodine staining demonstrated a loss of SC104 binding in both fractions following the removal of oligosaccharides (FIG. 8). This indicates that SC104 recognises an intact glycolipid and that this recognition is lost following oligosaccharide removal.

Phospholipids such as phosphatidylethanolamine, phosphatidyl serine and the related lyso groups have free amino groups that can be detected by ninhydrin staining HPTLC and ninhydrin staining of both the intact glycolipid and the ceramide glycanase treated fraction revealed the presence of phospholipids with $R_F$ values between 0.51 and 0.54. However, this may be a contaminant that co-migrates with the antigen, particularly as the literature suggests that co-elution of phospholipids and glycolipids is a common problem when employing a single silica column purification method. This indicates that such a method may be insufficient to resolve the antigen from the whole extract with sufficient purity to facilitate characterisation.

Experiment 3

Fractionation of Whole Lipid Extract into Lipid Sub-groups and Localisation of Antigen Methods Lipid was extracted from ~2 ml packed cell volume C170 cells as described above. Following evaporation the extract was resuspended in ~1 ml chloroform. A 10 ml bed volume silica column (150 mm i.d.) was prepared in 100% chloroform. The sample was added to the column and the column washed under gravity in the following solvents: 10 column volumes chloroform, to elute simple lipids; 40 column volumes acetone, to elute neutral glycolipids; 10 column volumes methanol to elute gangliosides and phospholipids. The fractions were collected and dried down via rotary evaporation and stored at 4° C. prior to analysis.

Neuraminidase digestion of antigen. Antigen solution (5 µl) was combined with 5 µl 10× buffer solution, provided with the neuraminidase, and 10 µl neuraminidase solution. The final volume was brought up to 50 µl, mixed and incubated at 37° C. for 1 hr.

Chemical de-sialylation by acid hydrolysis. Antigen solution in 0.05 M sulphuric acid was heated at 80° C. for 2 hrs. The sample was then allowed to cool and stored at 4° C. prior to analysis.

Results

In order to remove glycolipids from phospholipids, a 10 ml silica column was equilibrated with chloroform. Whole C170 lipid extract was obtained from ~2 ml packed cell volume. This was applied to the column and the column washed with chloroform, to elute the simple lipids; acetone, to elute glycolipids; and finally methanol to elute phospholipids.

HPTLC separation and immunostaining detected at least three antigen bands in the whole extract and phospholipid fraction ($R_F$ 0.54, 0.51 and 0.41) along with a single band in the simple lipid fraction ($R_F$ 0.51; FIG. 9). However, no antigen was detected in the glycolipid fraction. Ninhydrin staining revealed the presence of phospholipid in the whole extract and phospholipid fraction only. However, orcinol staining demonstrated that glycolipids were present in both the glycolipid and phospholipid fractions. Significantly, two distinct bands were observed in the phospholipid fraction ($R_F$ 0.54 and 0.51) that appear to co-migrate with the antigen, again indicating that the antigen may carry carbohydrate moieties.

Further reading indicated that although the above method can be used to separate neutral glycolipids from phospholipids, sialylated glycolipids co-elute with phospholipids. This, along with the co-migration of the antigen and orcinol positive bands provided some evidence that the antigen may be a sialylated glycolipid; while the absence of antigen in the neutral glycolipid fraction suggests that the glycolipid must be sialylated in order to be recognised by SC104.

Further evidence that the antigen is a sialylated glycolipid and not a phospholipid was obtained by separating whole lipid extract using 2D HPTLC and analysing the plates via immunostaining and chemical staining. In the first dimension the HPTLC plate was developed in the standard 50:40:10 chloroform:methanol:$CaCl_2$ solvent mixture. The plate was then allowed to dry, rotated 90° and developed in chloroform: acetone:methanol:acetic acid:water 10:4:2:2:1. Immunostaining revealed that very little migration of the antigen occurred in the second dimension (FIG. 10). This again demonstrated that the antigen is not a neutral glycolipid, since neutral glycolipids migrate in acetone. Orcinol staining of carbohydrates again showed a band that co-migrated with the antigen in both dimensions, while ninhydrin staining of free amino groups demonstrated a compound that co-migrated in the first dimension but which was then separated from the antigen in the second dimension.

Neuraminidase digestion was used to detect the effect of sialic acid removal on antibody recognition. Immunostaining of HPTLC separated phospholipid/ganglioside sample before and after neuraminidase treatment provided two clusters of bands; with a more polar cluster at $R_F$ 0.46 and a less polar at $R_F$ 0.62 (FIG. 11). Although the same bands were detected before and after neuraminidase treatment there was a shift in the intensity of the staining profile. Neuraminidase treatment produced more intense staining at the $R_F$ 0.46 cluster and a decrease in intensity at the $R_F$ 0.62 cluster when compared to the untreated control. This suggests that although sialic acid removal was only partial, since the conditions had not been optimised, removal of sialic acids from the more polar $R_F$ 0.62 cluster led to formation of a less polar cluster of molecules, which are still detected by the antibody. As the least polar bands detected after partial neuraminidase digestion co-migrated with the least polar bands in the untreated ganglioside/phospholipid fraction it is assumed that this cluster must itself correspond with a sialylated form, probably monosialylated, while the more polar cluster corresponds to a disialylated form.

Silica column chromatography was then employed to fractionate differentially sialylated glycolipids. A sample of lipid extract was loaded onto the column and fractions were eluted to obtain simple lipid (chloroform); asialylated glycolipids and phospholipids (chloroform:methanol:acetone:acetic acid:water 52:8:8:18:4, followed by chloroform:methanol 4:1); monosialylated glycolipids (chloroform:methanol 2:3); disialylated glycolipids (chloroform:methanol:water 65:25:4) and finally polysialylated glycolipids (chloroform:methanol:water 60:35:8). The fractions were then dried down and analysed by HPTLC followed by immunostaining and chemical staining (FIG. 12).

Orcinol and ninhydrin staining showed phospholipids and glycolipids were both present in the sialylated glycolipid fractions. However the antigen again appears to co-migrate with the only orcinol positive glycolipids and not the ninhydrin positive phospholipids.

HPTLC and immunostaining of these samples revealed three clusters of antigen in the whole extract ($R_F$ ~0.49, ~0.38 and ~0.24), with the most polar of these showing only very faint staining. No antigen was observed in the simple lipid fraction or the phospholipid/neutral glycolipid fraction, but antigen was detected in the sialylated fractions. This confirms that the antigen is a sialylated glycolipid and not a phospholipid. Two of the clusters of bands were detected in the monosialylated fraction ($R_F$ ~0.49 and $R_F$ ~0.38). In the disialylated fraction faint staining is visible for the most ($R_F$ ~0.24) and least ($R_F$ ~0.49) polar clusters, with the most intense staining detected for the middle cluster ($R_F$ ~0.38). In the polysialylated fraction two clusters are visible ($R_F$ ~0.38 and $R_F$ ~0.24). This suggests that the least polar cluster is monosialylated, the middle cluster represents disialylated structures and the most polar cluster has three or possibly four sialic acids.

Acid hydrolysis was then used to chemically de-sialylate the antigen. This method is more aggressive than enzymatic procedures and is more likely to result in complete removal of sialic acids. HPTLC and SC104 immunostaining demonstrated that chemical removal of sialic acids resulted in the complete loss of SC104 binding, providing further evidence that sialylation of the antigen is necessary for antibody binding.

SC104 therefore appears to bind to a mono, di and even polysialylated glycolipid. However it does not bind to an asialo form. This indicates that the antigen must be monosialylated however the presence of further sialic acids does not impinge on the binding of SC104. The increased intensity of staining for the disialylated form also suggests that despite only requiring the presence of one sialic acid, the antigen is most commonly found bearing two sialic acids. However, it is currently unclear if this is dependent upon the age and culture conditions of the C170 cells prior to harvesting.

Experiment 4

Comparison of Antigen to Commercially Available Lipid Standards

Methods

The SC104 antigen has been compared to a number of commercially available lipid standards. Examples of each standard were spotted onto HPTLC plates and developed in 50:40:10 chloroform:methanol:$CaCl_2$ (0.5% w/v). Plates were also spotted with partially purified SC104 antigen. Migration of each standard was detected by iodine vapour staining and the location of each marked on the plate. Plates were then probed with SC104. It was observed that none of the standards were recognised by SC104, suggesting that none of the standards represent the antigen.

Results

The $R_F$ values obtained for the standards are shown in Table 6 below. These values are also compared with the range of $R_F$ values obtained for the variably sialylated SC104 antigen, listed in order of increasing polarity and degree of sialylation.

TABLE 6

| Standard | Structure | $R_F$ | SC104 $R_F$ |
|---|---|---|---|
| Lactosyl ceramide | Glc-β1, 1-Cer | 0.79 | |
| Globotriaosyl ceramide (Gb3) | Gal-α1, 4Gal-β1, 4Glc-β1, 1-Cer | 0.71 | |
| Globotetraosyl ceramide (Globoside) | GalNAc-β1, 3Gal-α1, 4Gal-β1, 4Glc-β1, 1-Cer | 0.62 | |
| Globopentaosyl ceramide (Forrsman) | GalNAc-α1, 3GalNAc-β1, 3Gal-α1, 4Gal-β1, 4Glc-β1, 1-Cer | 0.56 | |
| GM3 | NeuAc-Galβ1, 4-Glc-β1, 1-Cer | 0.53 | 0.53<br>0.49 |
| AGM1 | Galβ1, 3-GalNAc-β1, 4-Gal β1, 4Glc-β1, 1-Cer | 0.48 | |
| GM1 | Galβ1, 3-GalNAc-β1, 4-(NeuAc)Gal β1, 4Glc-β1, 1-Cer | 0.39 | 0.39<br>0.36 |
| GD3 | NeuAc-NeuAc-Gal β1, 4Glc-β1, 1-Cer | 0.33 | <0.24 |
| GD1a | NeuAc-Galβ1, 3-GalNAc-β1, 4-(NeuAc)Gal β1, 4Glc-β1, 1-Cer | 0.22 | |
| GD1b | Galβ1, 3-GalNAc-β1, 4-(NeuAc-NeuAc)Gal β1, 4Glc-β1, 1-Cer | 0.16 | |
| GT1b | NeuAc-Galβ1, 3-GalNAc-β1, 4-(NeuAc-NeuAc)Gal β1, 4Glc-β1, 1-Cer | 0.08 | |

It can be seen that the least polar SC104 antigen co-migrates with GM3, while the most polar molecules migrate with $R_F$ values similar to GD1a and GD1b. However, in all cases the standards are themselves not recognised.

The migration of the antigen with $R_F$ values that are comparable to many of the standard gangliosides suggests that, along with the requirement for sialylation, the antigen has a short neutral oligosaccharide backbone that consists of three or four monosaccharides. It is most probable that this is actually a tetraosyl structure as this would more readily allow multiple sialylation. The least polar antigen that is detected is probably a partial antigen structure, consisting of a shorter oligosaccharide backbone.

Example 6

Identification of Tumour Glycoprotein Recognised by SC104 mab

Experiment 1

Methods

SC104 antigen purification and characterisation. SC104 specific antigen was purified from sputum samples mixed in a 1:1 ratio with 0.1M pH 7.6 Tris 0.5% NP40. Briefly an immuno-affinity was produced cross linking SC104 S136A to Protein A Cl-6B sepharose using Dimethyl pimelimidate.2HCl as the covalent linker Results It is noteworthy that whilst the antigen was seen to cross-react with SC104 (FIG. 13a) it did not cross react with an anti-sialyl Lewis $^a$ or 19/9 antibody.

Experiment 2

Methods

Sequence identification of the SC104 antigen. SC104 specific antigen was purified from sputum as outlined in experiment 1 above and the samples run on a 10% SDS-PAGE and Silver stained following the suppliers recommendations (Bio-Rad Silver stain kit, catalogue number 1610443). The band of interest was subsequently subjected to MALDI analysis.

Results

A band for the SC104 antigen at between 50-75 kDa was identified on a Silver stained gel (FIG. 14). The MALDI sequence analysis suggested several possible hits including:

P04839 GP91-PHOX) (GP91-1) (Heme binding membrane glycoprotein)

Q99741 Cell division control protein 6 homolog (CDC6-related protein)

Q14451 Growth factor receptor-bound protein 7 (GRB7 adapter protein)

P14618 Pyruvate kinase, isozymes M1/M2 (EC 2.7.1.40) (Pyruvate kinase muscle isozyme)

O96013 Serine/threonine-protein kinase PAK 4 (EC 2.7.1.37) (p21-activated kinase 4)

P01833 (Polymeric Ig receptor)

As SC104 recognises a carbohydrate, these results suggest that the sialyltetraosyl sugar can also be expressed on these glycoproteins.

Experiment 3

Methods

Competition assays using the immuno-purified antigen using the SC104 protein A sepharose column. The SC104 purified fraction was used as a competitor for SC104 binding to C170 cells using experiments based upon the ELISA technique (FIG. 15). Microtitre plates were coated with $5\times10^4$/well of C170s, the cells fixed and blocked prior to being incubated with solutions of biotinylated antibody (0.1

μg/well) mixed with increasing ratio of antigen. Bound SC104 biotinylated antibody was detected by SA-HRP and TMB. Results are expressed as absorbance at 650 nm.

Results

The immuno-purified SC104 antigen using the protein A Cl-6B sepharose immuno-affinity column has demonstrated its ability to specifically inhibit the binding of the antibody to its target.

Example 7

SC104 Directly Induces Tumour Cell Killing

Experiment 1

Methods

Annexin/PI. Tumour cells ($1 \times 10^5$ aliquots) in suspension incubated with SC104 antibody (1 μg/ml) or appropriate controls for 4 hr at room temperature could then also be stained with FITC labelled annexin and propidium iodide (Sigma, Poole, Dorset) and then analysed by dual colour flow cytometry.

Results

This study has shown strong staining of freshly disaggregated colorectal tumours. However during these studies it was observed that SC104 antibody appeared to accelerate tumour cell death. A similar phenomenon was observed when tumour cell lines which normally grew as adherent monolayers were placed in suspension and stained with SC104 antibodies for flow cytometric analysis. To determine if the antibody was inducing apoptosis or necrosis, cells exposed to SC104 antibody were counterstained with annexin and propidium iodide (FIG. 16). Less than 25% of the cells stained with the control antibody showed staining with either annexin or propidium iodide. In contrast cells exposed to concentration greater than 10 μg/ml SC104 showed strong staining with 30% of cells staining with annexin, 75% with PI and 65% with both. Cells stained with annexin alone are described as in early stages of apoptosis whereas cells stained with both annexin and PI are in late stage apoptosis/necrosis.

Experiment 2

Methods

Pan caspase activation. $2 \times 10^5$ colorectal C170 cells were exposed to 30 μg/ml of SC104 for up to 6 hrs and pan caspase FITC-FMK-vad (caspACE FITC-vad-FMK, Promega, catalogue number G7462) employed to establish caspase activation. The cells were analysed by flow cytometry. Controls included a negative control murine antibody and a Fas antibody at 100 ng/ml.

Results

The results of the assay demonstrate that SC104 activates pan caspases after 5 hrs (FIG. 17).

Experiment 3

Methods

Caspase 6 activation by SC104 mab. $2 \times 10^5$ colorectal C170 cells were exposed to 1-100 μg/ml of SC104 for 6 hrs and cell lysates generated. The lysates were subsequently run a 12% SDS-PAGE, Western blotted and probed with a caspase 6 specific antibody (Cleaved caspase 6 antibody, Cell Signalling Technology (NEB), catalogue number 9761). Cells exposed to SC101 were included as a negative control.

Results

Development of the Western blot (FIG. 18) clearly demonstrates that there is activation of caspase 6 in those C170 cells exposed to 10, and more intensely at 100 μg/ml of SC104 mab. Those cells subjected to treatment with the SC101 mab showed no such activation of caspase 6.

Experiment 4

Methods

SC104 inhibition of cell death using the z-FMK-vad caspase inhibitor. $2 \times 10^5$ C170 cells were subjected to 3 μg/ml of SC104 and half were also incubated with 3 μM z-FMK-vad inhibitor (Promega, catalogue number G7232) and incubated overnight. The following day cell viability was assayed using annexin V FITC and propidium iodide.

Results

There was a 23% increase in viable cells in the presence of the inhibitor (FIG. 19), providing a strong indication that SC104 kills colorectal cells by a 'classic' apoptotic pathway.

Experiment 5

Methods

Inhibition of cell growth. $1 \times 10^3$ colorectal C170, C168, C146, CaCO2, Colo205, LoVo and HT29 cells were aliquoted into individual wells of a flat bottomed 96-well plate and left to adhere overnight at 37° C. The following day the cells were treated with: 10, 3, 1, 0.3 and 0 μg/ml of SC104 mab. As a negative control 791T/36 at concentrations 100, 30, 10, 3 and 0 μg/ml, was titrated against each concentration of drug used. Triplicate wells were used. Cells were left for 5 days at 37° C. prior to the addition of MTS reagent to each well and optical density reading at 490 nm.

Results

The effect of SC104 on adherent cell proliferation was measured in an MTS assay. At concentrations in excess of 10 μg/ml SC104, but not control antibody, inhibited growth of the colorectal tumour cell line C170 and Colo205 but not HT29 or LoVo. (FIG. 20). FIG. 21 demonstrates $IC_{50}$ fits for tumour cell lines C170, Colo205, HT29 and LoVo. Similar results were obtained with other breast and colorectal tumour cell lines (Table 7). These results suggested that SC104 was inhibiting tumour cell proliferation by inducing apoptosis at high doses. However cells in suspension that had lost their cell/cell contact were sensitised to rapid cell death at lower antibody concentrations.

TABLE 7

SC104 inhibits cell growth

| | % inhibition of cell growth as measured by MTS staining | |
|---|---|---|
| Cell line | SC104 (30 μg/ml) | 791T/36 (30 μg/ml) |
| C170 | 70 | 10 |
| C146 | 65 | 6 |
| C168 | 55 | 3 |
| CaCO2 | 20 | 2 |
| Colo205 | 55 | 5 |
| HT-29 | 5 | 5 |

Experiment 3

Homophilic Binding

Methods

FACS on fresh and fixed cells. C170 cells ($10^5$) either fresh or fixed with 0.5% glutaraldehyde for 1 hr were resuspended in 100 µl of SC104 mab (0-100 µg/ml) and incubated on ice for 1 hr. After washing the samples 3 times in RPMI/10% FCS cells were incubated with FITC labelled rabbit anti-mouse (1/80: Dako Ltd, Bucks, UK) antibody and incubated on ice for 30 minutes prior to analysing by FACS as described above.

ELISA for homophilic binding. Flat flexi 96 well ELISA plates were coated with anti-mouse IgG Fc specific antibody or were coated with 3 µg/ml (100 µl/well) of C14 antigen in PBS and dried down overnight. Plates were washed 3 times with PBS prior to blocking with PBS/1% BSA for 1 hr at room temperature. SC104 antibody (0-100 µg/ml) was added on ice for 1 hr. After washing the plate 3 times in PBS/0.05% tween-20, biotinylated SC104 was added and incubated on ice for 30 minutes. Following a further 3 washes in PBS 0.05% tween-20 anti-mouse SA-HRP (1/1000; Dako, High Wycombe, UK) or goat anti-mouse Fc (1/1000: Dako, High Wycombe, UK) was added as appropriate and left on ice for 30 min. Plates were washed 5 times in PBS/0.05% tween-20 before adding 100 µl/well of TMB substrate and reading at 570 nm.

Results

The number of SC104 haptens at the surface of a C170 tumour cells is approximately $4 \times 10^5$ sites per cell. However this number of antigens would easily be saturated at 1 µg/ml of SC104. It was therefore difficult to explain why a 10 fold excess of antibody was required for cell killing. It could be that upon antibody binding more sites are revealed. Antibody saturation curves were therefore generated on fresh and fixed cells. The antigen was not saturated even at SC104 concentration of 100 µg/ml and curves were similar on fresh and fixed cells making it unlikely that further antigen was being revealed (FIG. 22). These results are similar to previously reported data on R24 a mouse mab recognising GD3 ganglioside. This antibody shows non-saturable antibody binding and in a series of elegant experiments was shown to be a homophilic binding antibody with the capacity to bind to both antigen and itself (results not shown). SC104 was therefore screened for the ability to bind to itself by coating an ELISA plate with unlabelled SC104 and measuring the binding of SC104 biotin HRP-avidin. SC104 did not bind to itself (FIG. 23) however when purified glycoprotein expressing SC104 haptens was used to coat the plates SC104 bound stoichiometrically until 10 µg/ml and then bound exponentially beyond this concentration (FIG. 23). These results suggest that at low antibody concentrations the antibody binds to antigen but at high concentrations antibody bound to antigen can also bind further antibody. This can dramatically increase the functional avidity of antibodies leading to lattices of antibodies building up on cells with high density antigen. This lattice formation could result in multiple signals resulting in apoptosis at high antibody concentrations.

Experiment 4

In Vitro Inhibition of Cell Growth in Combination with Cytotoxic Drugs $1 \times 10^3$ colorectal C170 cells were aliquoted into individual wells of a flat bottomed 96-well plate and left to adhere overnight at 37° C. The following day the cells were treated with cisplatin, mitomycin C, oxaliplatin and tamoxifen at final concentrations of 10, 3, 1, 0.3, 0.1 and 0 µM. Against each concentration of drug the following concentrations of SC104 were titrated: 10, 3, 1, 0.3 and 0 µg/ml. As a negative control 791T/36 at concentrations 100, 30, 10, 3 and 0 µg/ml, was titrated against each concentration of drug used. Duplicate wells were used. Cells were left for 5 days at 37° C. prior to the addition of MTS reagent to each well and optical density reading at 490 nm.

Results

The ability of SC104 to show additive killing with chemotherapeutic agents was screened in vitro by MTS assays. All drugs were titrated between (0.1-10 µg/ml) in the presence of either SC104 or control antibody (0.3-100 µg/ml). FIG. 24 shows a representative experiment for cells treated with a combination of SC104 and 5-FU. FIG. 25 summarises the results showing that SC104 shows additive killing with cisplatin, mitomycin C, 5-FU and tamoxifen. No additive effect was seen with oxaliplatin.

Experiment 5

In Vivo Inhibition of Tumour Cell Growth in Combination with Cytotoxic Drugs Methods Prevention model. The colorectal tumour cell line, C170 was maintained in serial passage in nude mice. For therapy the mice were sacrificed and the tumours excised. The tumour was finely minced and 3 mm$^2$ pieces were implanted, under anaesthetic, subcutaneously into 30 male mice which had been randomly allocated to 4 experimental groups.

Mice were explanted with 3 mm$^3$ pieces of C170 xenografts. Groups of mice were treated with 5-FU/leucovorin (12.5 mg/Kg) by intravenous infusion on days 1, 3, 5, 7 and 28. On the same days mice were also injected intraperitoneally with 0.2 mg of SC104 mab. Control mice received either SC104 alone or control mouse IgG antibody with 5-FU/leucovorin. Tumour size was measured by callipers and tumour cross sectional area calculated on days 7, 9, 12, 14 and 16. Animals were weighed to assess the toxicity of treatment. At the termination of the experiment tumours were weighed to assess anti-tumour efficacy.

Therapeutic model. The colorectal tumour cell line, C170 was maintained in serial passage in nude mice. For therapy the mice were sacrificed and the tumours excised. The tumour was finely minced and 3 mm$^2$ pieces were implanted, under anaesthetic, subcutaneously into 30 male mice which had been randomly allocated to 4 experimental groups.

Mice were explanted with 3 mm$^3$ pieces of C170 xenografts. Groups of mice were treated with 5-FU/leucovorin (12.5 mg/Kg) by intravenous infusion on days 3, 5, 7, 21 and 22. On the same days mice were also injected intraperitoneally with 0.2 mg of SC104 mab. Control mice received either SC104 alone or control mouse IgG antibody with 5FU/leucovorin. Tumour size was measured by callipers and tumour cross sectional area calculated on days 12, 16, 19 and 23.

Results

Figure 26A:
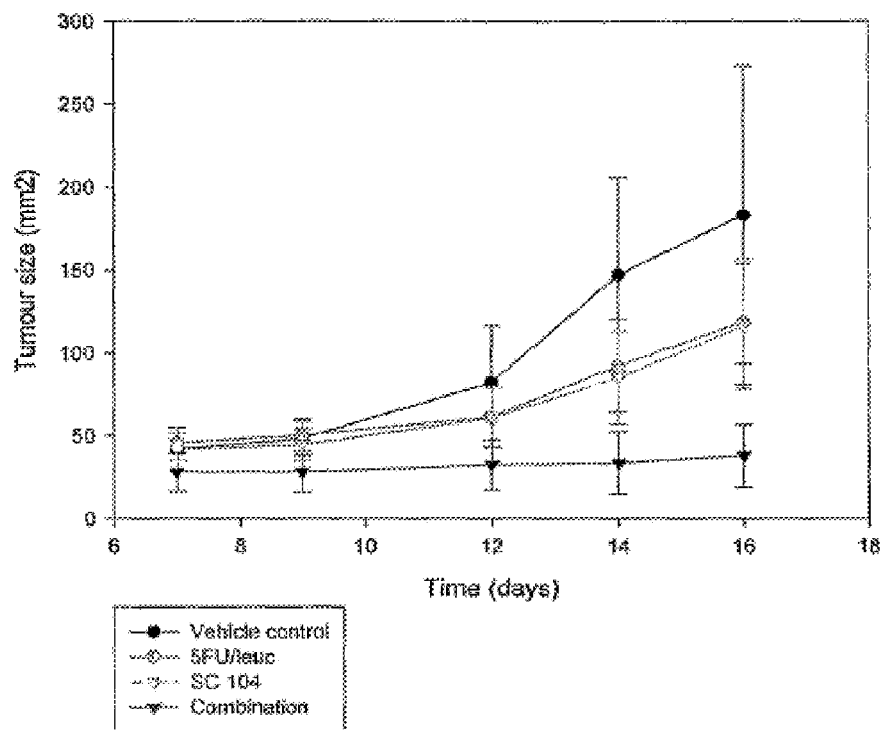

To determine if these effects could be translated to inhibition of tumour growth in vivo. SC104 was administered (200 µg/dose) 3 weekly to mice either transplanted with 3 mm$^2$ extracts of C170 tumours or to C170 tumours that had been allowed to grow for 5 days prior to administration of the antibody. Animals were treated either with SC104 alone, 5-FU/leucovorin at the maximum tolerated dose or a combination of both for 3 weeks. FIG. 26a shows that both SC104 or 5-FU/leucovorin alone resulted in 50% inhibition of tumour growth of freshly explanted tumours. In contrast, the combination of both showed synergistic inhibition of growth. Tumours in all groups showed a temporal increase in tumour growth until day 16 when the staggered termination began. From day 9, the combination treatment group showed significant inhibition of growth when compared with all other treatment groups as follows:

SC104 and 5-FU, day 9; 37% inhibition, p=0.004; day 12; 59% inhibition, p=0.002; day 14; 74% inhibition, p=<0.001; day 16; 76% inhibition, p=<0.001.

5-FU, day 9; 40% inhibition, p=0.004; day 12; 45% inhibition, p=0.004; day 14; 58% inhibition, p=<0.001; day 6; 62% inhibition, p=<0.001.

SC104, day 9; 32% inhibition, p=0.017; day 12; 44% inhibition, p=0.004; day 14; 54% inhibition, p=0.001; day 16; 62% inhibition p=<0.001. All statistics assessed by ANOVA.

Figure 26B:
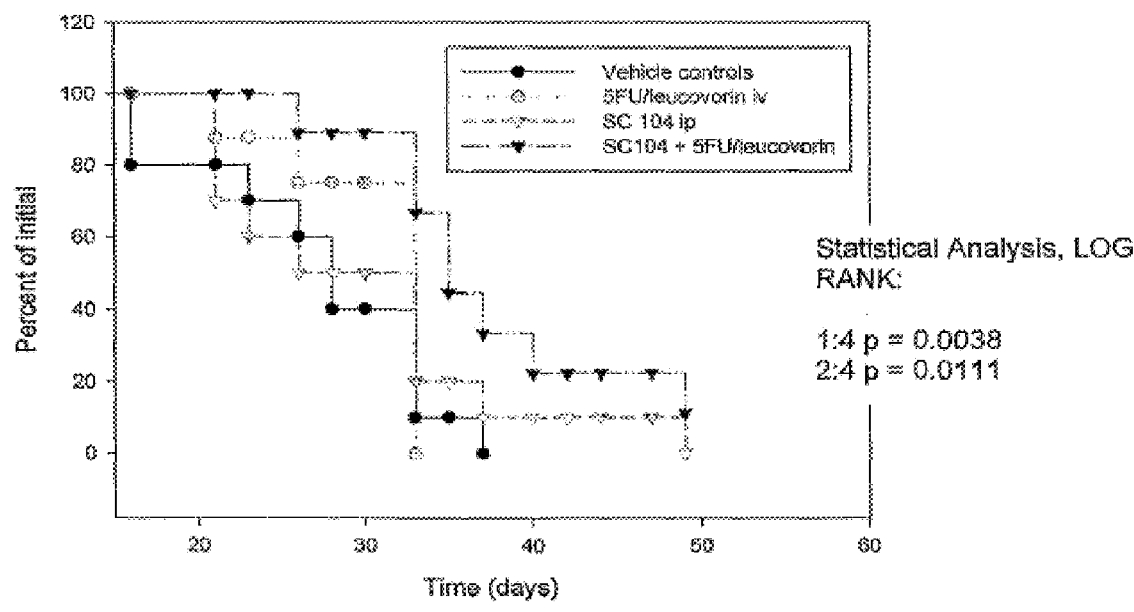

There was no significant difference between the SC104 treated group and that receiving the cytotoxic agent, 5-FU/leucovorin. This correlated into a significant improvement of survival of mice treated with SC104, 5-FU or the combination (FIG. 26b). The combination of SC104 and 5-FU treated group showed enhanced survival compared with both the vehicle control group and the 5-FU treated group as follows:
Combination: vehicle: p=0.0038.
Combination: cytotoxic: agent p=0.0111 (All statistics by Log Rank)

Figure 26C:
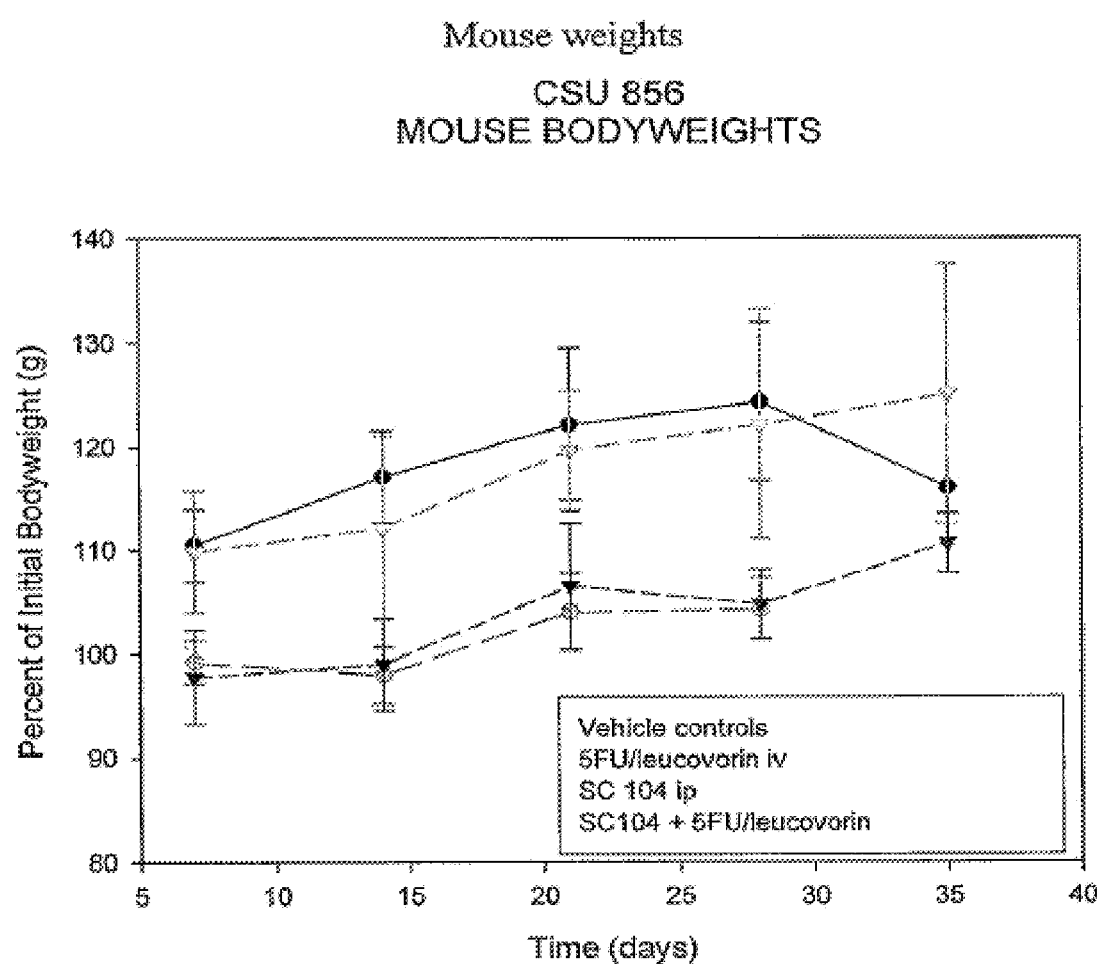

This dose of SC104 was well tolerated with all mice showing no loss of weight or any other gross pathology (FIG. 26c). Finally, when SC104 was administered therapeutically, 7 days after C170 xenograft tumour implantation neither 5FU nor SC104 alone significantly inhibited growth however in combination with 5FU/leucovorin it both significantly inhibited tumour growth and enhanced survival (FIG. 27). SC104 plus 5-FU/leucovorin exhibited a significant reduction in final weight/time and inhibited tumour growth with enhanced survival in the C170 subcutaneous xenograft model.

While this invention has been particularly shown and described with references to preferred embodiments thereof, it will be understood by those skilled in the art that various changes in form and details may be made therein without departing from the scope of the invention encompassed by the appended claims.

What is claimed:

1. An isolated antibody which binds Colo205 and directly induces cell death without the need for immune effector cells, wherein the antibody binding domain of the heavy chain comprises CDR1, CDR2 and CDR3 and wherein the sequence of CDR1 of the antibody binding domain is amino acids 44 to 54 or 49 to 54 of SEQ ID NO: 23 and the sequence of CDR2 of the antibody binding domain is amino acids 69 to 84 of SEQ ID NO: 23 and the sequence of CDR3 of the antibody binding domain is amino acids 117 to 127 of SEQ ID NO: 23 and wherein the antibody binding domain of the light chain comprises CDR1, CDR2 and CDR3 and the sequence of CDR1 of the antibody binding domain is amino acids 46 to 55 of SEQ ID NO: 27 and the sequence of CDR2 of the antibody binding domain is amino acids 71 to 77 of SEQ ID NO: 27 and the sequence of CDR3 of the antibody binding domain is amino acids 110 to 118 of SEQ ID NO: 27.

2. An isolated antibody as claimed in claim 1, wherein CDR1, CDR2 and CDR3 are carried by a human antibody framework.

3. An isolated antibody as claimed in claim 1, further comprising a human constant region.

4. An isolated antibody as claimed in claim 1, wherein the sequence of the heavy chain antibody binding domain is residues 19 to 138 of SEQ ID NO: 23.

5. An isolated antibody as claimed in claim 1, wherein the sequence of the Light chain antibody binding domain is residues 23 to 128 of SEQ ID NO: 27.

6. A pharmaceutical composition comprising an isolated antibody as claimed in claim 1 and a pharmaceutically acceptable excipient, diluent, carrier, buffer or stabilizer.

* * * * *